United States Patent
Zissel et al.

(10) Patent No.: US 10,786,550 B2
(45) Date of Patent: Sep. 29, 2020

(54) BLOCKADE OF CCL18 SIGNALING VIA CCR6 AS A THERAPEUTIC OPTION IN TREATING INTERSTITIAL LUNG DISEASE

(71) Applicant: UNIVERSITÄTSKLINIKUM FREIBURG, Freiburg (DE)

(72) Inventors: Gernot Zissel, Freiburg (DE); Joachim Müller-Quernheim, Kirchzarten (DE); Antje Prasse, Freiburg (DE)

(73) Assignee: Universitatsklinikum Freiburg, Freiburg (DE)

(*) Notice: Subject to any disclaimer, the term of this patent is extended or adjusted under 35 U.S.C. 154(b) by 0 days.

(21) Appl. No.: 15/148,102

(22) Filed: May 6, 2016

(65) Prior Publication Data

US 2016/0354439 A1 Dec. 8, 2016

Related U.S. Application Data

(62) Division of application No. 13/806,997, filed as application No. PCT/EP2011/060641 on Jun. 24, 2011, now abandoned.

(30) Foreign Application Priority Data

| Jun. 28, 2010 | (EP) | ..................... 10167496 |
|---|---|---|
| Jun. 9, 2011 | (EP) | ..................... 11169326 |

(51) Int. Cl.

| A61K 38/16 | (2006.01) |
|---|---|
| A61K 38/17 | (2006.01) |
| G01N 33/68 | (2006.01) |
| G01N 33/574 | (2006.01) |
| A61K 9/00 | (2006.01) |
| C07K 14/715 | (2006.01) |
| A61K 45/06 | (2006.01) |
| C07K 14/00 | (2006.01) |
| C07K 16/24 | (2006.01) |
| C07K 16/28 | (2006.01) |
| C12N 15/113 | (2010.01) |
| C12N 15/115 | (2010.01) |
| A61K 38/00 | (2006.01) |

(52) U.S. Cl.
CPC ........ *A61K 38/1793* (2013.01); *A61K 9/0019* (2013.01); *A61K 38/16* (2013.01); *A61K 45/06* (2013.01); *C07K 14/00* (2013.01); *C07K 14/7158* (2013.01); *C07K 16/24* (2013.01); *C07K 16/2866* (2013.01); *C12N 15/115* (2013.01); *C12N 15/1136* (2013.01); *C12N 15/1138* (2013.01); *G01N 33/57423* (2013.01); *G01N 33/6863* (2013.01); *A61K 38/00* (2013.01); *C12N 2310/11* (2013.01); *C12N 2310/14* (2013.01); *C12N 2310/16* (2013.01); *G01N 2333/521* (2013.01); *G01N 2333/7158* (2013.01); *G01N 2500/02* (2013.01); *G01N 2800/12* (2013.01)

(58) Field of Classification Search
None
See application file for complete search history.

(56) References Cited

U.S. PATENT DOCUMENTS

| 6,713,052 B1 | 3/2004 | White et al. |
|---|---|---|
| 6,998,239 B1 | 2/2006 | Gosling et al. |
| 7,166,702 B1 | 1/2007 | McDonald et al. |
| 2003/0186889 A1 | 10/2003 | Forssmann et al. |

(Continued)

FOREIGN PATENT DOCUMENTS

| EP | 1422239 | 5/2004 |
|---|---|---|
| JP | 2003-530325 | 10/2003 |
| WO | WO-2000055180 | 9/2000 |

(Continued)

OTHER PUBLICATIONS

Ai et al. Molecular characterization of CCR6: Involvement of multiple domains in ligand binding and receptor signaling. J Biomed Sci. Nov.-Dec. 2004;11(6):818-28.*

Allen, S.J., "Chemokine: Receptor Structure, Interactions and Antagonism," Annu. Rev. Immunol. 2007. 25:787-820.

Altschul et al., Basic local alignment search tool. J Mol Biol. Oct. 5, 1990;215(3):403-410.

(Continued)

*Primary Examiner* — Dong Jiang
(74) *Attorney, Agent, or Firm* — Jenkins, Wilson, Taylor & Hunt, P.A.

(57) ABSTRACT

The present invention relates to an isolated soluble CCR6 receptor polypeptide capable of binding to CCL18 and/or CCL20 and to a method for quantifying the concentration of a soluble CCR6 receptor polypeptide in a liquid sample from a subject. The present invention also relates to a method for detecting and/or prognosticating an interstitial lung disease or a cancer in a subject by determining the level of a soluble CCR6 receptor polypeptide in a sample from said subject and further provides a pharmaceutical composition comprising a compound capable of inhibiting the activity and/or the expression of CCL18 or CCL20 for the treatment of said diseases. The present invention further relates to an isolated polypeptide capable of binding to and inhibiting the activity of the chemokine receptor CCR6 and to a method for identifying further inhibitors of CCR6 receptor activity. The present invention also relates to a method for detecting an interstitial lung disease or a cancer in a subject by determining the level of CCR6 gene expression in a sample from said subject and further provides pharmaceutical compositions comprising inhibitors of CCR6 receptor activity and/or expression for the treatment of said diseases.

Figure 1:
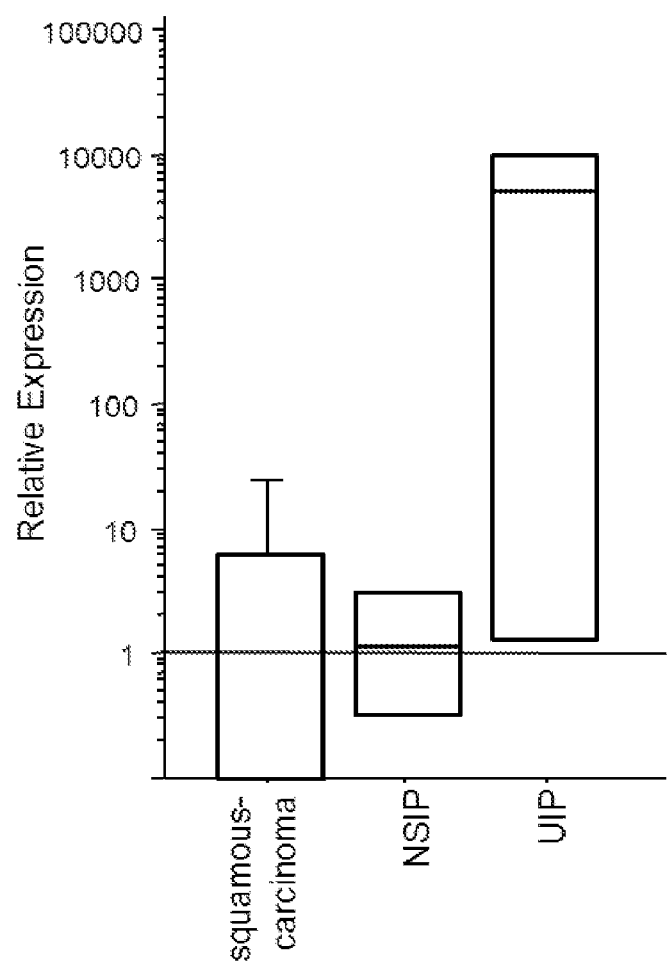

3 Claims, 22 Drawing Sheets
Specification includes a Sequence Listing.

(56) References Cited

U.S. PATENT DOCUMENTS

| | | | |
|---|---|---|---|
| 2004/0156822 | A1 | 8/2004 | White et al. |
| 2004/0161425 | A1 | 8/2004 | Munn et al. |

FOREIGN PATENT DOCUMENTS

| | | |
|---|---|---|
| WO | WO-2001032874 | 5/2001 |
| WO | WO-2001072830 | 2/2005 |
| WO | WO 2005015206 | 2/2005 |
| WO | WO-2005095953 | 10/2005 |
| WO | WO-2008054764 | 5/2008 |

OTHER PUBLICATIONS

American Thoracic Society and European Respiratory Society, American Thoracic Society/European Respiratory Society International Multidisciplinary Consensus Classification of the Idiopathic Interstitial Pneumonias. This Joint Statement of the American Thoracic Society (ATS), and the European Respiratory Society (ERS) was adopted by the ATS Boards of Directors, Jun. 2001 and by the ERS Executive Committee, Jun. 2001. Am J Respir Crit Care Med. Jan. 15, 2002;165(2):277-304.
Christopherson et al., Low-Molecular-Weight Heparins Inhibit CCL21-Induced T Cell Adhesion and Migration. J Pharmacol Exp Ther. Jul. 2002;302(1):290-5.
Extended European Search Report (EESR) issued in European Application No. 10 167 496.8 dated Feb. 2, 2011.
International Preliminary Report on Patentability issued in PCT/EP2011/060641 dated Dec. 28, 2012.
International Search Report and Written Opinion issued in PCT/EP2011/060641 dated Oct. 21, 2011.
Office Action issued in European Application No. 10 167 496.8 dated Aug. 20, 2012.
Partial European Search Report (PESR) issued in European Application No. 10 167 496.8 dated Oct. 15, 2010.
Droemann et al., Human lung cancer cells express functionally active Toll-like receptor 9. Respir Res. Jan. 4, 2005;6:1 (10 pages).
Facco et al., Expression and role of CCR6/CCL20 chemokine axis in pulmonary sarcoidosis. J Leukoc Biol. Oct. 2007;82(4):946-955.
Ghadjar et al., The chemokine CCL20 and its receptor CCR6 in human malignancy with focus on colorectal cancer, Int J Cancer. Aug. 15, 2009; 125(4):741-745.
Goldmann et al., Assessment of Transcriptional Gene Activity in situ by Application of HOPE-Fixed, Paraffin-embedded Tissues. Pathol Res Pract. 2002;198(2):91-95.
Karlin and Altschul, Applications and statistics for multiple high-scoring segments in molecular sequences. Proc Nat Acad Sci USA Jun. 15, 1993;90(12):5873-5877.
Kohler and Milstein, Derivation of specific antibody-producing tissue culture and tumor lines by cell fusion. Eur J Immunol. Jul. 1976;6(7):511-519.
Lin et al., Temporal Proteomics Profiling of Lipids Rafts in CCR6-Activated T Cells Reveals the Integration of Actin Cytoskeleton Dynamics. J Proteome Res. Jan. 2010;9(1):283-297.

Maier, Expressionsanalyse des Chemokinrezeptors CCR6 auf Fiboblasten. Inaugural-Dissertation, Frieburg 2008. Partial English Translation p. 67.
Maier, Expressionsanalyse des Chemokinrezeptors CCR6 auf Fiboblasten. Inaugural-Dissertation, Frieburg 2008:1-79.
Pardo et al., CCL 18/DC-CK-1/PARC up-regulation in hypersensitivity pneumonitis. J Leukoc Biol. Oct. 2001;70(4):610-616.
Pechkovsky et al., Effect of proinflammatory cytokines in interleukin-8 mRNA expression and protein production by isolated human alveolar epithelial cells type II in primary culture. Eur Cytokine Netw. Dec. 2000;11(4):618-625.
Pechkovsky et al., Pattern of NOS2 and NOS3 mRNA expression in human A549 cells and primary cultured AEC II. Am J Physiol Lung Cell Mol Physiol. Apr. 2002;282(4):L684-692.
Perez-Canadillas, J.M. et al., "NMR Solution Structure of Murine CCL20/MIP-3α, a Chemokine That Specifically Chemoattracts Immature Dendritic Cells and Lymphocytes through Its Highly Specific Interaction with the β-Chemokine Receptor CCR6," The Journal of Biological Chemistry, vol. 276, No. 30, Issue of Jul. 27, pp. 28372-2379, 2001.
Prasse et al., CCL18 as an Indicator of Pulmonary Fibrotic Activity in Indiopathic Interstitial Pneumonias and Systemic Sclerosis. Arthritis Rheum. May 2007;56(5):1695-1693.
Prasse et al., Serum CC-Chemokine Ligand 18 Concentration Predicts Outcome in Idiopathic Pulmonary Fibrosis. Am J Respir Crit Care Med. Apr. 15, 2009;179(8): 717-723.
Prasse et al., Th1 cytokine pattern in sarcoidosis is expressed by bronchoalveolar CD4+ and CD8+ T cells. Clin Exp Immunol. Nov. 2000; 122(2):241-248.
Trepel et al., In vivo phage display and vascular heterogeneity: implications for targeted medicine. Curr Opin Chem Biol. Jun. 2002;6(3):399-404.
Ziegenhagen et al., Serum Level of Interleukin 8 is Elevated in Idiopathic Pulmonary Fibrosis and Indicates Disease Activity. Am J Respir Crit Care Med. Mar. 1998;157(3 Pt 1):762-768.
Zissel, Inhibition der CCL 18-induzierten Zellaktivierung durch ein CCL 18-Inhibitor Peptid. Universitats Klinikum Freiburg Pneumologie Feb. 11, 2010:1 page.
Zissel, Inhibition of the CCL 18-induced cell activation by a CCL 18 inhibitor peptide. University Medical Center Freiburg, Division Pneumology—project description English translation Feb. 11, 2010: 1 page.
Mendez-Enriquez et al., "CDIP-2, a synthetic peptide derived from chemokine (C-C motif) ligand 13 (CCL13), ameliorates allergic airway inflammation", Clinical and Experimental Immunology, vol. 152, No. 2, May 31, 2008, pp. 1-7.
Zissel, G. "Soluble CCR6 Diminishes Bioavailability of CCL18 in Serum" (unpublished), pp. 1-9 (2017).
Monteclaro and Charo, J. Biol. Chem., vol. 271, pp. 19084-19092 (1996).
Skelton et al., Structure, vol. 7, pp. 157-168 (1999).
Thiele and Rosenkilde, "Interaction of chemokines with their receptors—from initial chemokine binding to receptor activating steps," Curr. Med. Chem., vol. 21, pp. 3594-3614 (2014).

\* cited by examiner

Figure 3
Figure 4
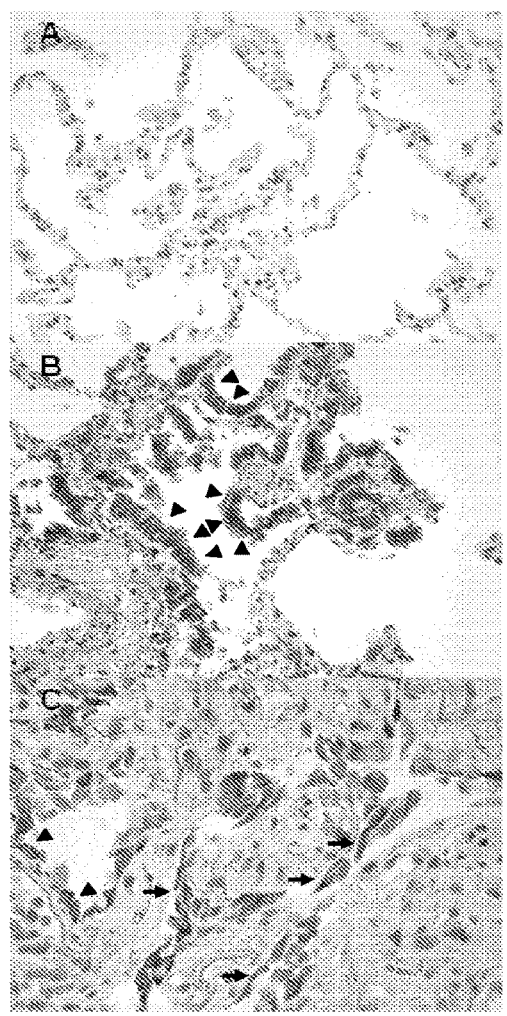
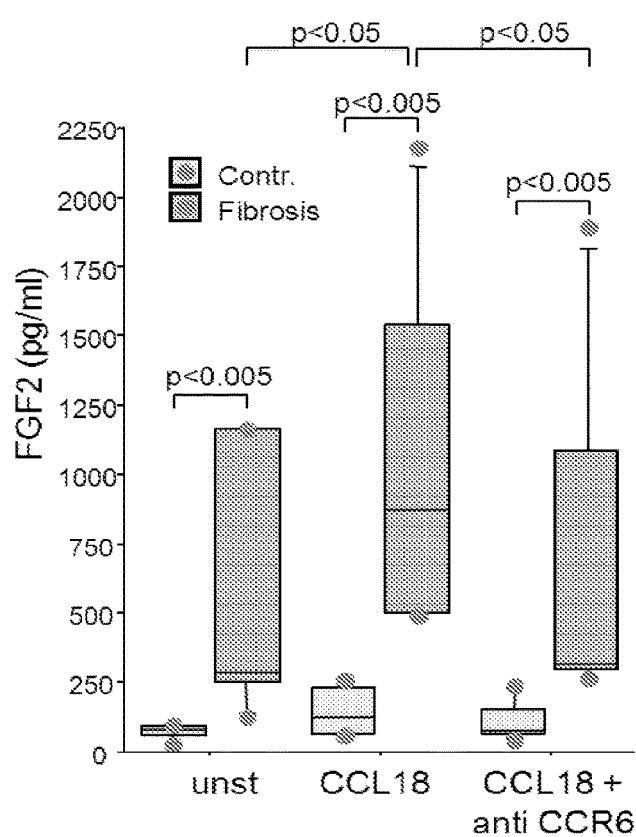

Figure 16
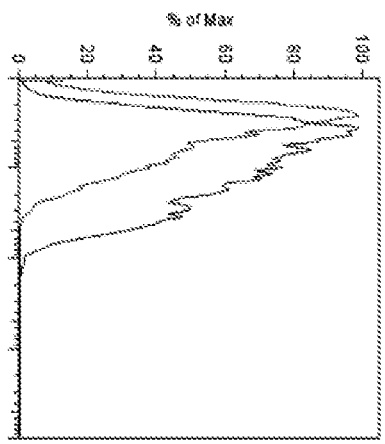
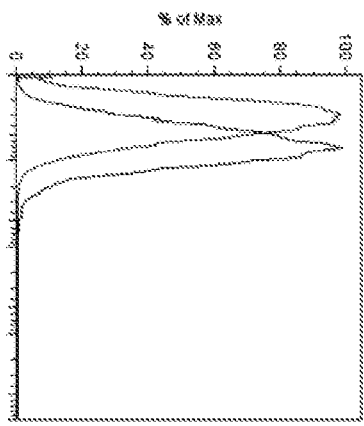
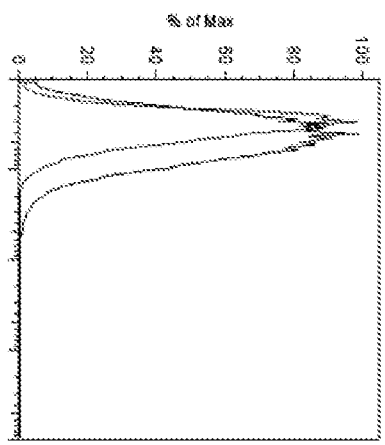
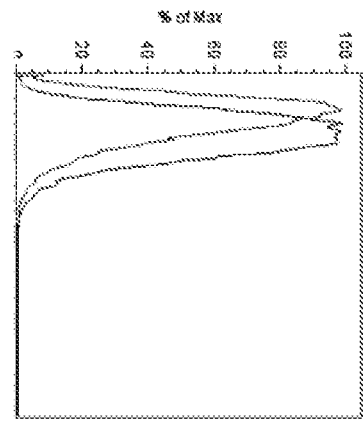
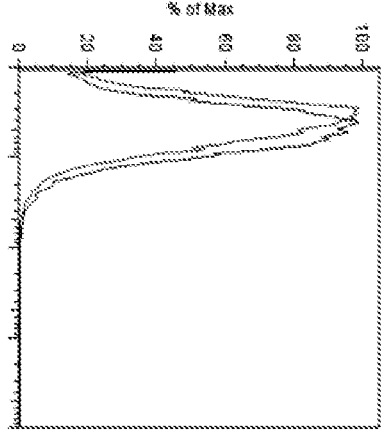
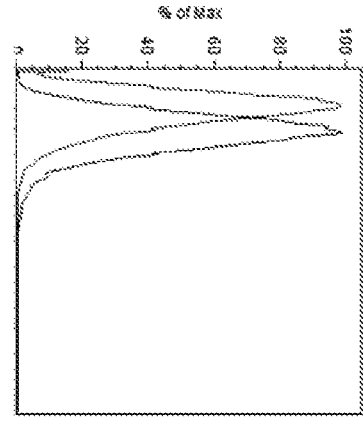

Figure 17

| Gene | accession number | forward primer | reversed primer |
|---|---|---|---|
| GAPDH | NM_002046.3 | CACCAGGGCTGCTTTTAACT (SEQ ID NO.: 10) | GATCTCGCTCCTGGAAGATG (SEQ ID NO.: 11) |
| CCR6 | NM_004367.5 NM_031409.3 | GCACAAAATGATGGCAGTGG (SEQ ID NO.: 12) | CCGAAGCACTTCCAGGTTGT (SEQ ID NO.: 13) |
| collagen type I | NM_000088.3 | CCCTGTCTGCTTCCTGTAAACT (SEQ ID NO.: 14) | CATGTTCGGTTGGTCAAAGATA (SEQ ID NO.: 15) |
| αSMA | NM_001141945.1 | CATCATGCGTCTGGATCTGG (SEQ ID NO.: 16) | GGACAATCTCACGCTCAGCA (SEQ ID NO.: 17) |

Figure 33

| SEQ ID NO.: 1 | MSGESMNFSDVFDSSEDYFVSVNTSYYSVDSEMLLCSLQEVRQFSRLF |
|---|---|
| SEQ ID NO.: 2 | SHATGAWVFSNATCKLLKG |
| SEQ ID NO.: 3 | CCR6 sequence according to NCBI accession number NM_004367.5 |
| SEQ ID NO.: 4 | CCR6 sequence according to NCBI accession number NM_031409.3 |
| SEQ ID NO.: 5 | CCL18 sequence according to NCBI accession number NM_002988.2 |
| SEQ ID NO.: 6 | CCL20 sequence according to NCBI accession number NM_004591.2 |
| SEQ ID NO.: 7 | CCL20 sequence according to NCBI accession number NM_001130046.1 |
| SEQ ID NO.: 8 | ATGAGCGGGGAATCAATGAATTTCAGCGATGTTTTCGACTCCAGTGAAGATTATTTTGTGTCAGTCAATACTTCATATTACTCAGTTGATTCTGAGATGTTACTGTGCTCCTTGCAGGAGGTCAGGCAGTTCTCCAGGCTATTT |
| SEQ ID NO.: 9 | EDCCLVYTSWQIHPKFIVDYSETSPQCPK (PS-AU-1015) |
| SEQ ID NO.: 18 | AQVGTNKELCCLVYTSWQIPQKFIVDYSETSPQCPKPGVILLTKRGRQICADPNKKWVQKYISDLKLNA |
| SEQ ID NO.: 19 | ASNFDCCLGYTDRILHPKFIVGFTRQLANEGCDINAIIFHTKKKLSVCANPKQTWVKYIVRLLSKKVKNM |
| SEQ ID NO.: 20 | MRTSYLLLFTLCLLLSEMASGGNFLTGLGHRSDHYNCVSSGGQCLYSACPIFTKIQGTCYRGKAKCCK |
| SEQ ID NO.: 21 | MRVLYLLFSLFIFLMPLPGVFGGIGDPVTCLKSGAICHPVFCPRRYKQIGTCGLPGTKCCKKP |
| SEQ ID NO.:22 | ELCCLVYTSWQIPQKFIVDYSETSPQCPK |
| SEQ ID NO.:23 | FDCCLGYTDRILHPKFIVGFTRQLANEGCDI |
| SEQ ID NO.:24 | GAGGACTGCTGCCTCGTCTATACCTCCTGGCAGATTCACCCAAAGTTCATAGTTGACTATTCTGAAACCAGCCCCCAGTGCCCCAAG |

Figure 33 Continued

| SEQ ID NO.:25 | GAGCTCTGCTGCCTCGTCTATACCTCCTGGCAGATTCCACA<br><br>AAAGTTCATAGTTGACTATTCTGAAACCAGCCCCAGTGCCCCAAG |
|---|---|
| SEQ ID NO.:26 | TTTGACTGCTGTCTTGGATACACAGACCGTATTCTTCATCCTAAATTT<br>ATTGTGGGCTTCACACGGCAGCTGGCCAATGAAGGCTGTGACATC |
| SEQ ID NO.:27 | MSGESMNFSDVFDSSEDYFVSVNTSYYSVDSEMLLCSLQEVRQFSRLFV PIAYSLICVFGLLGNILVVITFAFYKKARSMTDVYLLNMAIADILFVLTLP FWAVSHATGAWVFSNATCKLLKGIYAINFNCGMLLLTCISMDRYIAIVQ ATKSFRLRSRTLPRSKIICLVVWGLSVIISSSTFVFNQKYNTQGSDVCEPK YQTVSEPIRWKLLMLGLELLFGFFIPLMFMIFCYTFIVKTLVQAQNSKRH KAIRVIIAVVLVFLACQIPHNMVLLVTAANLGKMNRSCQSEKLIGYTKT VTEVLAFLHCCLNPVLYAFIGQKFRNYFLKILKDLWCVRRKYKSSGFSC AGRYSENISRQTSETADNDNASSFTM |

BLOCKADE OF CCL18 SIGNALING VIA CCR6 AS A THERAPEUTIC OPTION IN TREATING INTERSTITIAL LUNG DISEASE

FIELD OF THE INVENTION

The present invention relates to an isolated soluble CCR6 receptor polypeptide capable of binding to CCL18 and/or CCL20 and to a method for quantifying the concentration of a soluble CCR6 receptor polypeptide in a liquid sample from a subject. The present invention also relates to a method for detecting and/or prognosticating an interstitial lung disease or a cancer in a subject by determining the level of a soluble CCR6 receptor polypeptide in a sample from said subject and further provides a pharmaceutical composition comprising a compound capable of inhibiting the activity and/or the expression of CCL18 or CCL20 for the treatment of said diseases. The present invention further relates to an isolated polypeptide capable of binding to and inhibiting the activity of the chemokine receptor CCR6 and to a method for identifying further inhibitors of CCR6 receptor activity. The present invention also relates to a method for detecting an interstitial lung disease or a cancer in a subject by determining the level of CCR6 gene expression in a sample from said subject and further provides pharmaceutical compositions comprising inhibitors of CCR6 receptor activity and/or expression for the treatment of said diseases.

BACKGROUND OF THE INVENTION

Interstitial lung diseases are a heterogeneous group of disorders accompanied by various degrees of inflammation and fibrosis resulting in the damage of the lung parenchyma. Recently, the subgroup of idiopathic interstitial pneumonias has been classified into seven different syndromes. The most frequent of these conditions are idiopathic pulmonary fibrosis (IPF), non-specific interstitial pneumonia (NSIP) and cryptogenic organizing pneumonia (COP). The aetiology of said diseases has remained elusive and the molecular mechanisms driving their pathogenesis are poorly understood. However, the final pathway of fibroblast proliferation and extracellular matrix release represents a common pathway of fibrosing lung diseases of known and unknown etiology including collagen-vascular and systemic inflammatory diseases with pulmonary manifestations leading to fibrosis (e.g. rheumatoid arthritis, systemic sclerosis, scleroderma, hypersensitivity pneumonitis, some forms of drug induced alveolitis).

IPF is a distinctive type of chronic fibrosing interstitial pneumonia of unknown cause. When lung tissue from patients suffering from IPF is examined, it shows a characteristic set of histologic/pathologic features known as usual interstitial pneumonia (UIP). NSIP in contrast refers to cases of interstitial pneumonia in which a distinct pattern of more homogenous inflammation and fibrosis different from UIP can be identified.

IPF is slightly more common in males than in females and usually occurs in patients of 50 years of age or older.

Cytological examination of bronchoalveolar lavage fluid (BAL) is a common method in diagnosing and monitoring interstitial lung diseases, such as e.g. IPF. Bronchoalveolar lavage fluid from patients suffering from IPF, is characterized by significantly higher total cell and macrophage number, increased lymphocyte, neutrophile and eosinophile percentage as compared with bronchoalveolar lavage fluid from healthy controls.

Further common symptoms of IPF are shortness of breath, especially during or after physical activity, and a dry cough. Said symptoms often don't appear until the disease is advanced, and irreversible lung damage has already occurred.

The prognosis of IPF is rather poor with an average survival time of 3 years from the time of diagnosis.

At present no effective treatments and no cure for pulmonary fibrosis are available. Often treatment is limited to treating the inflammatory response that occurs in the lungs. Standard therapy includes anti-inflammatory and cytotoxic drugs like steroids and cyclophosphamides or azathioprine, however, these therapies are only of some value in e.g. NSIP (which also has a better prognosis than IPF) or desquamative interstitial pneumonia (DIP). IPF, however, is refractory to most of these therapeutic options. Experimental therapy studies using IFNγ, Bosentan® (endothelin antagonist), Aviptadil® (vasoactive intestinal peptide, VIP) or the tyrosine kinase inhibitor Imatinib® did also not reveal any profound beneficial effect of these drugs.

The development of novel therapies for the treatment of the various forms of pulmonary fibrosis, especially of IPF, therefore remains an essential task. There is a need for new cellular targets as well as therapeutic molecules which can efficiently impinge on these targets.

Chemokines are a family of chemoattractant, proinflammatory cytokines which are essential for homeostasis and activation of the immune system. They direct migration of immune cells into sites of inflammation and infection. Chemokines bind to specific cell surface receptors belonging to the family of seven-transmembrane domain, G protein-coupled receptors.

CCL18, also known as pulmonary and activation-regulated chemokine (PARC), alternative macrophage activation-associated CC chemokine 1 (AMAC-1), macrophage inflammatory protein-4 (MIP-4) and dendritic cell-derived chemokine1 (DCCK1), is a chemokine that is mainly expressed by a broad range of monocytes/macrophages and dendritic cells. It is constitutively expressed at high levels in human lung. CCL18 attracts T cells, immature dendritic cells, and induces collagen synthesis by fibroblasts. Furthermore, there are hints that CCL18 might also induce the chemotaxis of B cells.

CCL18 levels are enhanced in various disease states, such as e.g. inflammatory disorders of the skin, lung and joints. It has also been found that CCL18 is released in elevated levels by alveolar macrophages from patients suffering from pulmonary fibrosis and the serum levels of this chemokine is a prognostic marker in fibrotic diseases.

Moreover, it could be demonstrated that CCL18 induces the differentiation of fibroblasts into myo-fibroblasts and induces the expression of collagen and α-smooth-muscle-actin. Due to its known collagen inducing properties, high levels of CCL18 might directly be linked to the increased matrix deposition in pulmonary fibrosis.

However, exact analysis of signaling events and possible therapeutic interventions in CCL18 signalling is hampered by the fact that its receptor is not known.

Soluble receptors have recently been introduced into clinical medicine as a novel form of therapy. Most soluble receptors compete with their membrane-bound counterparts for their ligands and thus act as competitive antagonists. Soluble receptors provide the advantage that they are highly specific, bind their targets with high affinity, and are less likely to induce an immune response that might attenuate their actions. Furthermore, they have the potential to act at a distance, such that they may be administered far from the site of action. In view of theses advantages, soluble receptors hold significant potential for therapeutic use.

Cancer is a class of diseases in which a group of cells display uncontrolled growth, invasion and sometimes metastasis. These three malignant properties of cancers differentiate them from benign tumors, which are self-limited and do not invade or metastasize.

Cancer is a major health problem causing about 13% of all deaths worldwide.

According to the American Cancer Society, 7.6 million people died from cancer in the world during 2007. Deaths from cancer are projected to continue rising, with an estimated 12 million deaths in 2030.

The development of novel therapies to combat cancer therefore remains an essential task.

Lung cancer is the leading cause of cancer-related mortality and is one of the most important malignant neoplasms because of its high prevalence and increasing incidence. Nearly 80% of all lung cancers are histological defined as non-small cell lung cancer (NSCLC). Despite of advantages in new technologies and developing of new drugs contributing to a much earlier diagnosis and a more sufficient treatment, NSCLC remains a life threatening disease. The overall 5-year survival time for NSCLC patients is still low and even in the early stages of the disease the relapse rate is relatively high. The poor prognosis is due to the highly aggressive behavior of the tumor as demonstrated by a fast tumor growth and an early metastasis. Although the exact mechanism of carcinogenesis and metastasis in NSCLC are still unknown, the microenvironment of the tumor seems to play a key role in the development of malignant diseases and the dissemination of tumor cells.

NSCLC is a term describing several forms of tumors. 25-40% of the NSCLC are adenocarcinoma. This type of tumors develops from mucus producing cells and is located mainly in the periphery of the lung. The second frequent histological type of tumor is the squamous cell carcinoma which develops from squamous cells covering the surface of the alveoli and bronchioles.

The microenvironment of solid tumors is a complex mixture of cellular and non cellular factors. Especially the immune cells located in the surrounding of the tumor and the chemokine-crosstalk promote the growth of tumor cells and their spreading. Tumor associated macrophages (TAM) are one of the most important subgroup of immune cells in the tumor microenvironment and represent up to 50% of the tumor mass. Some studies demonstrate a significant correlation between the number of TAMs and a poor prognosis in malignant diseases.

OBJECTIVE AND SUMMARY OF THE INVENTION

It is one objective of the present invention to provide an isolated soluble CCR6 receptor polypeptide capable of binding to CCL18 and/or CCL20.

It is a further object of the invention to provide a method for quantifying the concentration of a soluble CCR6 receptor polypeptide in a liquid sample from a subject as well as a diagnostic in vitro method that can be used for detecting and/or prognosticating an interstitial lung disease or a cancer in a subject.

It is another objective of the present invention to provide an inhibitor of CCR6 receptor activity. It is a further object of the invention to provide a method for identifying inhibitors of CCR6 receptor activity.

Another object of the present invention is to provide pharmaceutical compositions comprising compounds suitable for the treatment of an interstitial lung disease and/or cancer, wherein said interstitial lung disease is preferably idiopathic pulmonary fibrosis (IPF) and wherein said cancer is preferably an adenocarcinoma, most preferably an adenocarcinoma of the lung.

These and other objectives as they will become apparent from the ensuing description and claims are attained by the subject matter of the independent claims. Some of the preferred embodiments are defined by the dependent claims.

In a first aspect the present invention provides an isolated soluble CCR6 receptor polypeptide comprising or consisting of an amino acid sequence selected from the group consisting of:
  (a) an amino acid sequence which exhibits at least 80% identity to the sequence according to SEQ ID NO.: 1; and
  (b) a fragment of the amino acid sequence according to (a);
wherein said isolated soluble CCR6 receptor polypeptide is capable of binding to CCL18 and/or CCL20.

In another aspect the present invention relates to a method for quantifying the concentration of a soluble CCR6 receptor polypeptide in a liquid sample from a subject, wherein the method comprises the steps of:
  (a) immobilizing a capture molecule specific for soluble CCR6 receptor on a solid support;
  (b) adding the liquid sample from the subject;
  (c) optionally adding a ligand of soluble CCR6 receptor, wherein said ligand is a polypeptide comprising or consisting of an amino acid sequence which exhibits at least 80% identity to the sequence according to SEQ ID NO.: 18, SEQ ID NO.: 19, SEQ ID NO.: 20 or SEQ ID NO.: 21;
  (d) adding a detecting agent specific for the ligand according to (c), wherein said detecting agent comprises a detectable label;
  (e) quantifying the signal from the detecting agent according to (d).

In yet another aspect the present invention relates to a method for detecting and/or prognosticating an interstitial lung disease or cancer in a subject, wherein the method comprises the step of determining the level of soluble CCR6 receptor polypeptide in a sample from said subject.

In a further aspect the present invention provides a pharmaceutical composition comprising a compound capable of inhibiting the activity and/or the expression of CCL18 or CCL20.

In another aspect the present invention relates to the isolated soluble CCR6 receptor polypeptide according to the invention for use in therapy.

In a further aspect the present invention relates to the isolated soluble CCR6 receptor polypeptide according to the invention or a pharmaceutical composition according to the invention for use in the treatment or prevention of an interstitial lung disease and/or cancer.

In yet another aspect the present invention relates to a detecting agent specific for the isolated soluble CCR6 receptor polypeptide according to the invention for use in detecting an interstitial lung disease or cancer in a sample from a subject.

In a further aspect the present invention provides an isolated polypeptide comprising or consisting of an amino acid sequence selected from the group consisting of:

(a) an amino acid sequence which exhibits at least 80% identity to the sequence according to SEQ ID NO.: 9, 22 or 23; and
(b) a fragment of the amino acid sequence according to (a);

wherein said isolated polypeptide is capable of binding to and inhibiting the activity of the CCR6 receptor.

In another aspect the present invention relates to an isolated polynucleotide encoding a polypeptide according to the invention.

In yet another aspect the present invention relates to a method for identifying a compound capable of inhibiting the activity of the CCR 6 receptor, wherein the method comprises the steps of:
(a) contacting a CCR 6 receptor with a test compound;
(b) adding a CCR6 receptor agonist, wherein said agonist is a polypeptide comprising or consisting of an amino acid sequence which exhibits at least 80% identity to the sequence according to SEQ ID NO.:5 or SEQ ID NO.:18;
(c) determining the activity of said CCR6 receptor; and
(d) selecting said test compound as the compound capable of inhibiting the activity of the CCR 6 receptor if the CCR6 receptor activity determined in (c) is lower than the CCR 6 receptor activity determined in a control.

In a further aspect the present invention relates to a method for detecting an interstitial lung disease or cancer in a subject comprising the step of determining the level of CCR6 gene expression in a sample from said subject.

In another aspect the present invention provides a pharmaceutical composition comprising a compound capable of inhibiting the activity and/or the expression of the CCR6 receptor.

In yet another aspect the present invention relates to a pharmaceutical composition according to the invention for use in the treatment or prevention of an interstitial lung disease and/or cancer.

In a further aspect the present invention also relates to the use of a compound capable of inhibiting the activity and/or expression of the CCR6 receptor or a pharmaceutical composition according to the invention for the manufacture of a medicament for the treatment or prevention of an interstitial lung disease and/or cancer.

FIGURE LEGENDS

FIG. 1 CCR6 mRNA expression by different fibroblast lines from patients suffering from squamous carcinoma (n=3), NSIP (n=2) and UIP (n=3). CCR6 expression was normalized using the housekeeping gene Glycerinaldehyd-3-phosphat-dehydrogenase (GAPdH).

Figure 2:
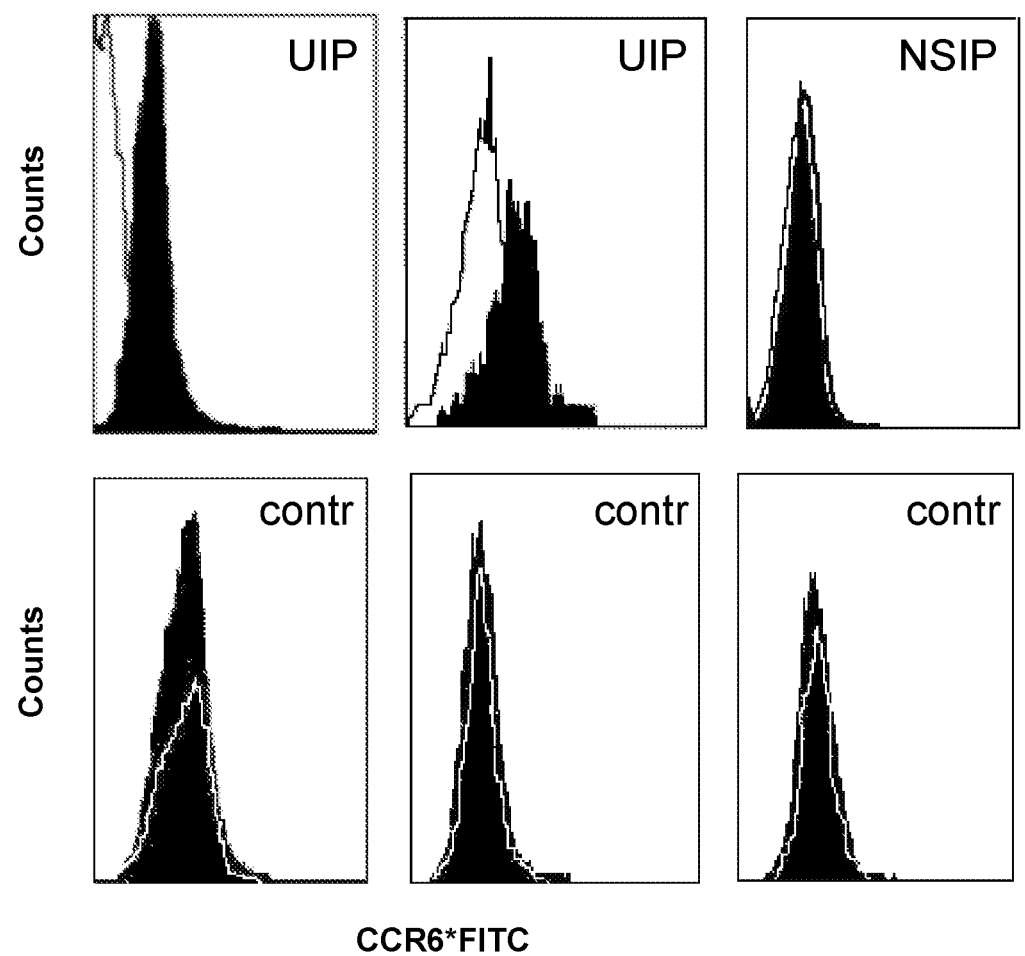

FIG. 2 Analysis of CCR6 expression by different fibroblast lines from patients suffering from UIP (upper panel, left and mid), NSIP (upper panel right), and squamous carcinoma (SQ CA; lower panel).

FIG. 3 CCR6 is not expressed in control lung (A), however, in fibrotic lungs expression of CCR6 can be found at the apical surface of alveolar epithelial cells (B and C, arrow heads) and on fibroblasts (C, arrows) (magnification: A: ×100, B: ×200, C: ×400).

FIG. 4 Unstimulated (unst.) FGF2 release is increased in fibroblasts from fibrotic lungs (grey, n=6 (UIP n=3, sarcoidosis n=1, NSIP n=1, undefined n=1)) compared with fibroblasts from non-fibrotic lungs (light grey, "Contr.", n=6). CCL18 induces a significant up-regulation of FGF2 release in fibroblasts from fibrotic lungs but only marginal in fibroblasts from non-fibrotic lungs. Blockade of CCR6 with a blocking antibody inhibits the CCL18 induced up-regulation of FGF2 release. Again, this effect is only seen in fibroblasts from fibrotic lungs.

Figure 5:
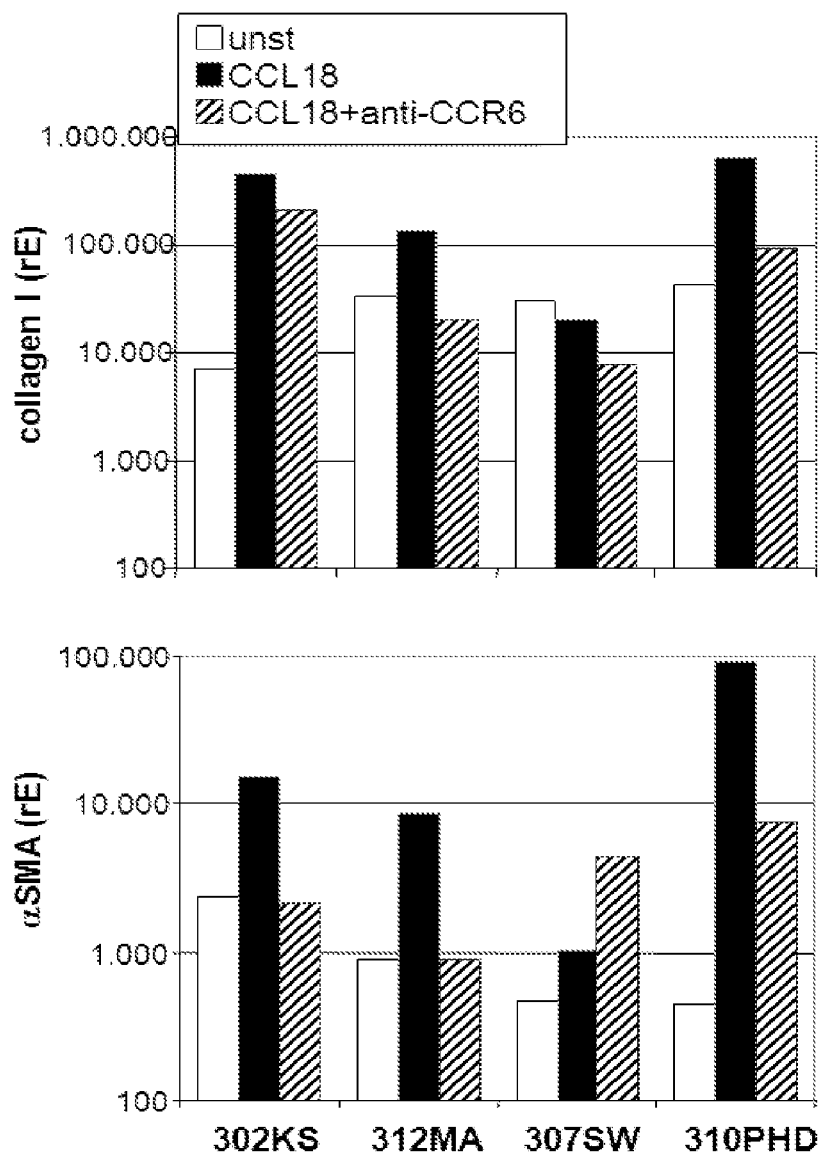

FIG. 5 CCL18 induced collagen I mRNA expression in three out of four (upper panel) and alpha-smooth muscle actin (αSMA) mRNA expression in all investigated human lung fibroblast cell lines (lower panel) (ordinate indicates line names). Collagen I mRNA expression and alpha-smooth muscle actin (αSMA) mRNA expression is blocked by anti-CCR6 (rE=relative Expression).

Figure 6:
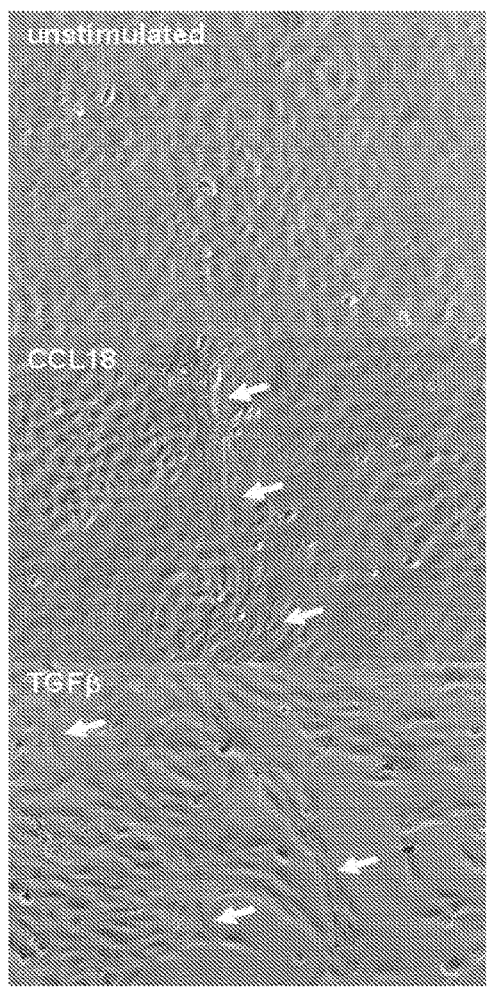

FIG. 6 The transformed rat alveolar epithelial cell line RLE-6TN undergoes epithelial-mesenchymal transition (EMT) after stimulation with TGFβ or CCL18. Arrows indicate fibroblast like cells. Culture period=6 days.

Figure 7:
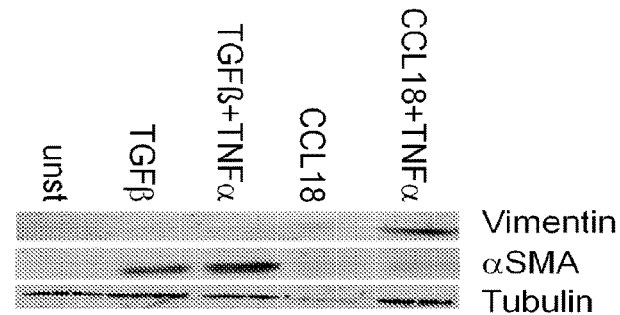

FIG. 7 Western Blot analysis of the expression of vimentin and αSMA cultured for 6 days either un-stimulated or in the presence of TGFβ, TGFβ+TNFα, CCL18, or CCL18+TNFα.

Figure 8:
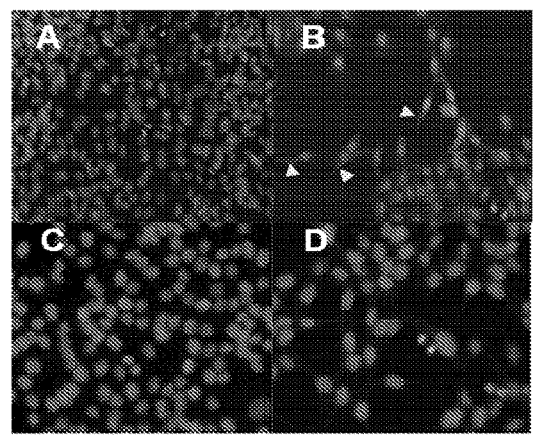

FIG. 8 Immuno-reactivity for αSMA was assessed by immuno-fluorescence on day 6. RLE-6TN cells were left unstimulated (A) or stimulated with (B) TGFβ+TNFα, (C) CCL18 (D), or CCL18+TNFα. Nuclei are stained by DAPI. αSMA is only visible in panel B uncovering the typical shape of fibroblasts (arrow heads). In contrast, in panel C and D only nuclei are evident.

Figure 9:
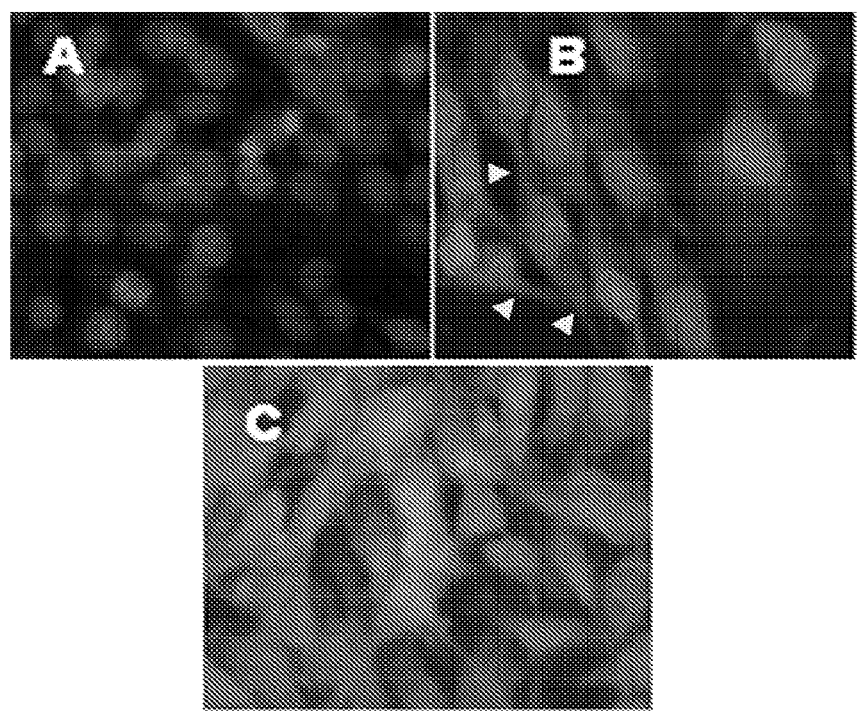

FIG. 9 Immuno-reactivity of CD90 was assessed by immuno-fluorescence on day 6. RLE-6TN cells were left unstimulated (A) or stimulated with TGFβ+TNFα (B), CCL18 (C). Nuclei are stained by ToPro3. Unstimulated cells do not express CD90 and only the nuclei are visible. In contrast, both TGFβ+TNFα and CCL18 stimulated cells express CD90 as demonstrated by the uncovering of the cell shape.

Figure 10:
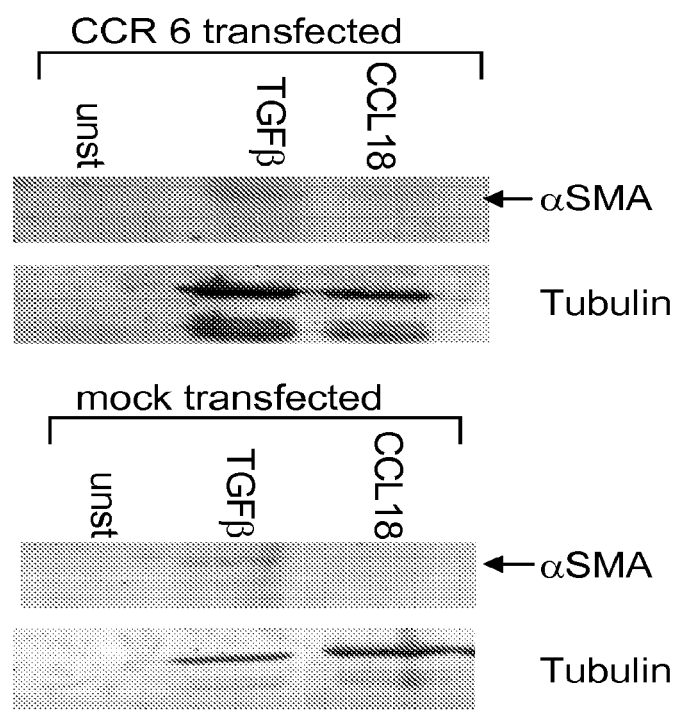

FIG. 10 CCL18 induced expression of αSMA is found in CCR6 transfected RLE-6TN but not in mock-transfected cells. In contrast, TGFβ induce αSMA expression in both cell lines.

Figure 11:
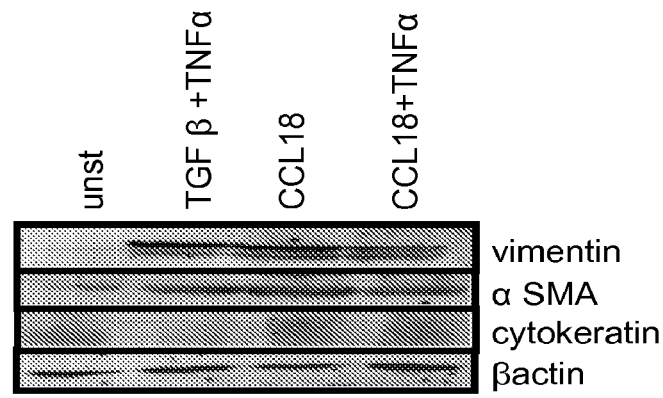

FIG. 11 human primary AECII were stimulated 12 days with TGFβ+TNFα or CCL18 in absence or presence of TNFα. Total cell lysate was separated by 10% SDS-PAGE and analyzed by Western blot. Non-stimulated cells only marginally express α-smooth muscle actin (αSMA) and no vimentin. Stimulation with TGFβ+TNFα and CCL18 alone or in combination with TNFα strongly up-regulates both molecules. Interestingly, cytokeratin is down-regulated by TGFβ+TNFα but preserved by CCL18 alone or in combination with TNFα.

Figure 12:
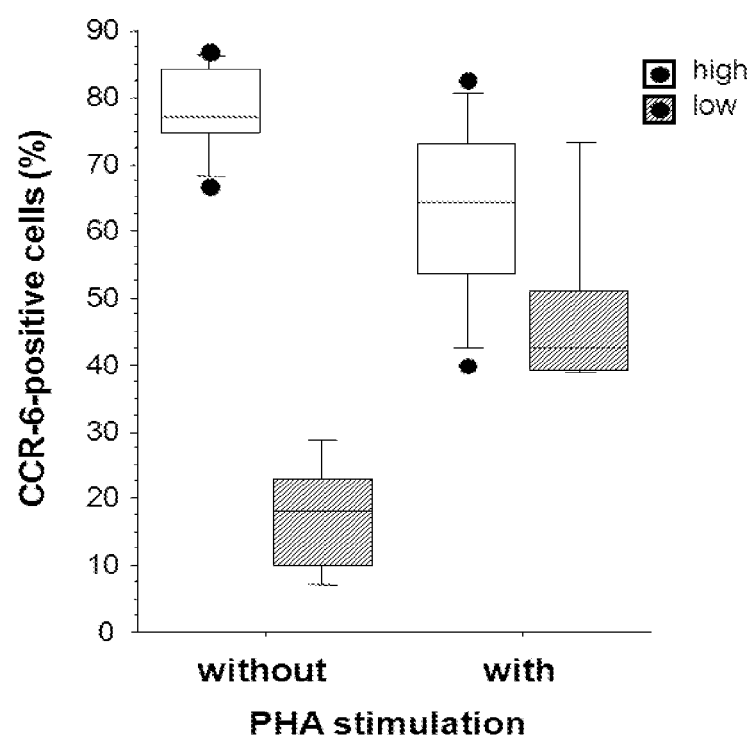

FIG. 12 Expression of CCR6 by peripheral blood mononuclear cells after 7 days of culture in the presence or absence of phytohemagglutinin (PHA; 5 µg/ml). Cell preparations were grouped in "high" or "low" CCR6 expressing preparations according to their initial CCR6 expression. After the culture period, non-stimulated preparations did not change CCR6 expression pattern.

In contrast, stimulation with PHA reduced CCR6 expression in the high expression group but increased expression in the low expression group.

Figure 13:
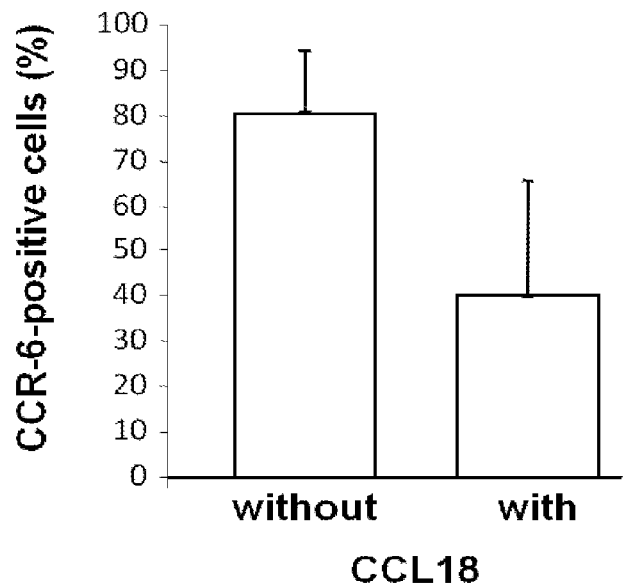

FIG. 13 Down-regulation of CCR6 receptor after 20 minutes incubation with CCL18 (10 ng/ml). Incubation with CCL18 leads to a marked down-regulation of the CCR6 surface expression. This effect is caused by receptor internalization after ligand-receptor interaction.

Figure 14:
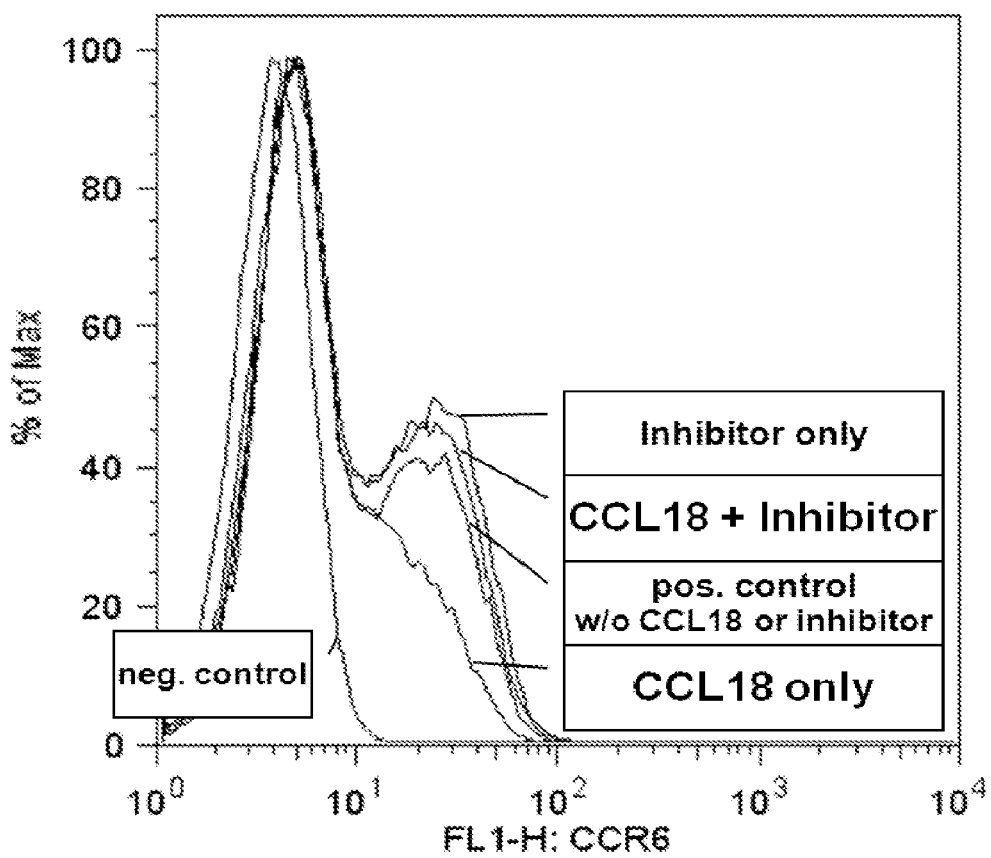

FIG. 14 FACS analysis of CCL18 induced down-regulation of CCR6 expression on human lymphocytes and its inhibition by the inhibitor PS-AU-1015 (polypeptide according to SEQ ID NO:9). A subpopulation of freshly isolated human lymphocytes express the chemokine receptor CCR6 visible as a lower peak right hand side of the main peak (pos. control). Incubation with CCL18 (10 ng/ml) for 20 minutes diminishes the peak markedly (CCL18 only). Upon incubation of the cells with CCL18 (10 ng/ml) in the presence of the inhibitor PS-AU-1015 (SEQ ID NO: 9; 100 ng/ml) this down-regulation does not occur (CCL18+inhibitor). Inhibitor only exhibits no effect.

Figure 15:
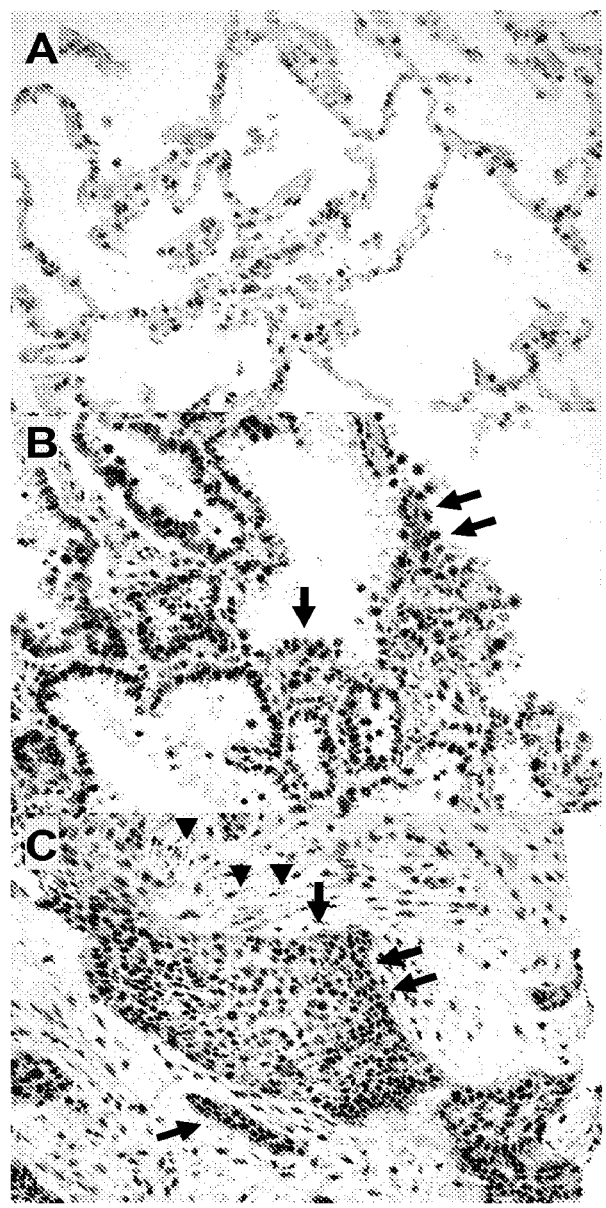

FIG. 15 CCR6 staining in lung sections from control lung (A) and two adenocarcinoma lungs (B, C). No staining is visible in the control lung whereas tumour cells are positive for CCR6 (red colour, arrows).

FIG. 16 Expression of CCR6 on the surface of lung adenocarcinoma cells (upper panel) and pleural mesothelioma cells (lower panel). Left peak indicates isotype control, right peak indicates CCR6 expression. Two out of three adenocarcinoma cell lines and all pleural mesothelioma cell lines exhibit marked CCR6 expression.

FIG. 17 Listing of primers used for PCR.

Figure 18:
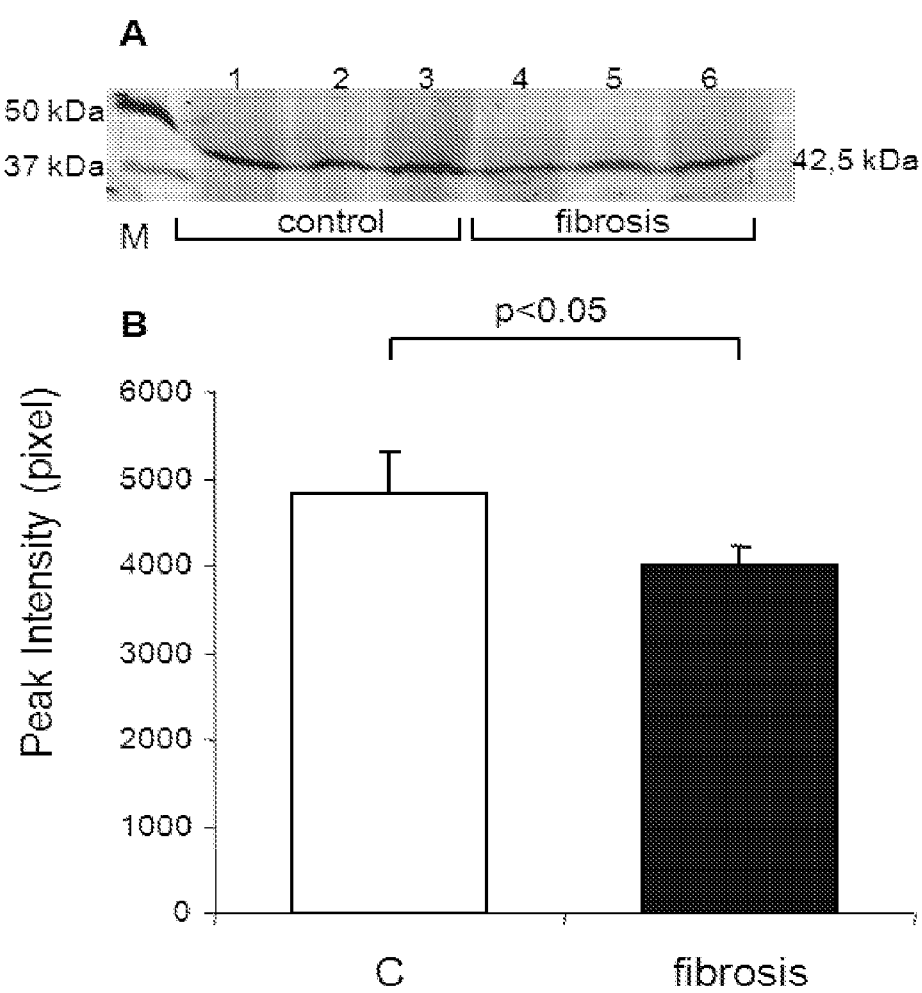

FIG. 18 Western blot analysis of sera from healthy volunteers serving as controls (n=3; lanes 1-3) and fibrosis (UIP) patients (n=3; lanes 4-6) (A). Molecular sizes are given at the border of the graphic. (C=control; M=protein marker). Densitometric analysis of the western blots (B).

Figure 19:
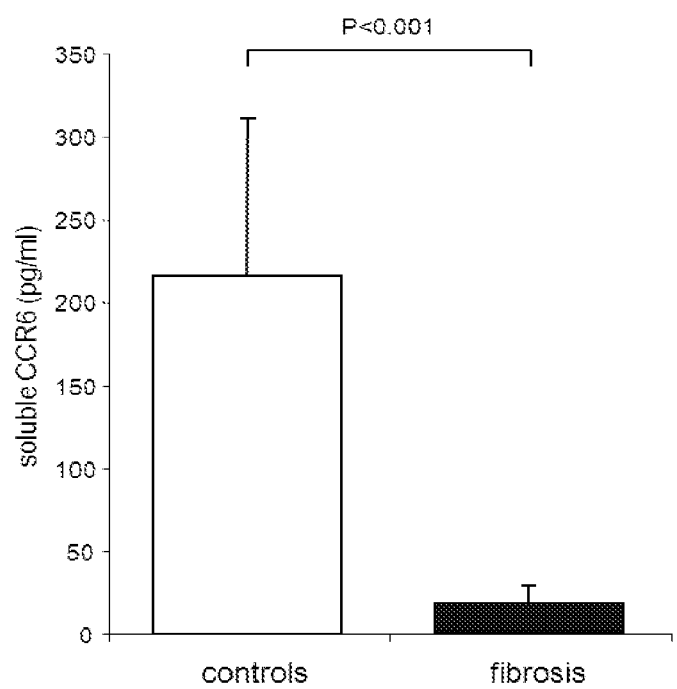

FIG. 19 Analysis of control sera from healthy volunteers (n=9) and fibrosis patients (UIP, n=19).

Figure 20:
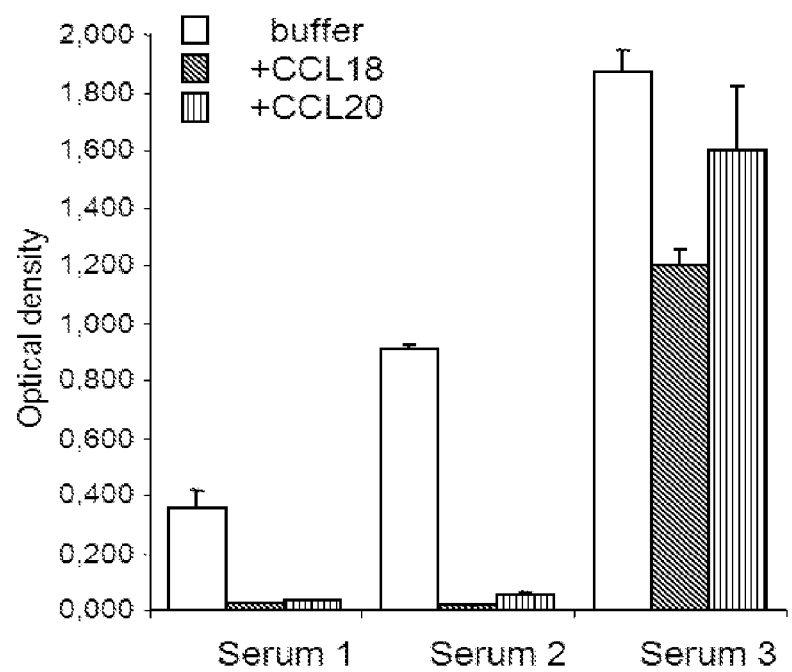

FIG. 20 Blocking of soluble CCR6 (sCCR6) detection by ELISA using the CCR6 ligands CCL18 and CCL20 (100 ng/ml each) for 1 h. Low and median concentrations are totally blocked whereas high concentration is reduced by one third. Serum 1, 2 and 3 are sera from healthy volunteers.

Figure 21:
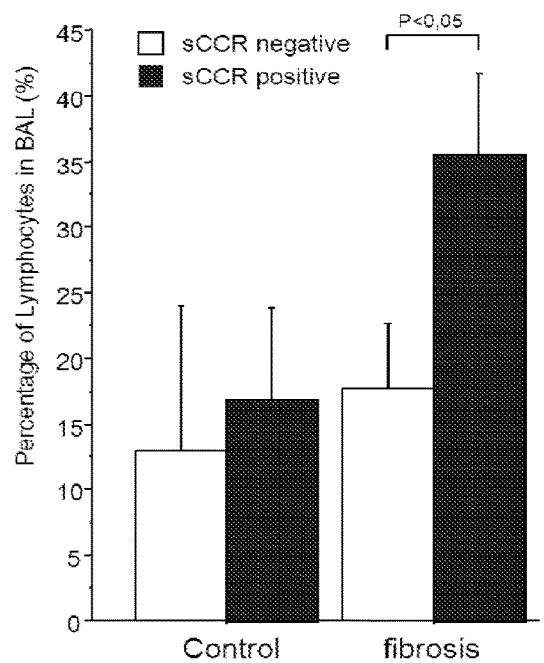

FIG. 21 Percentage of lymphocytes in BAL from sCCR6 positive and sCCR6 negative controls and (UIP) patients. The percentage of lymphocytes is significantly increased in serum sCCR6 positive patients. This effect is less pronounced in controls (not significant).

Figure 22:
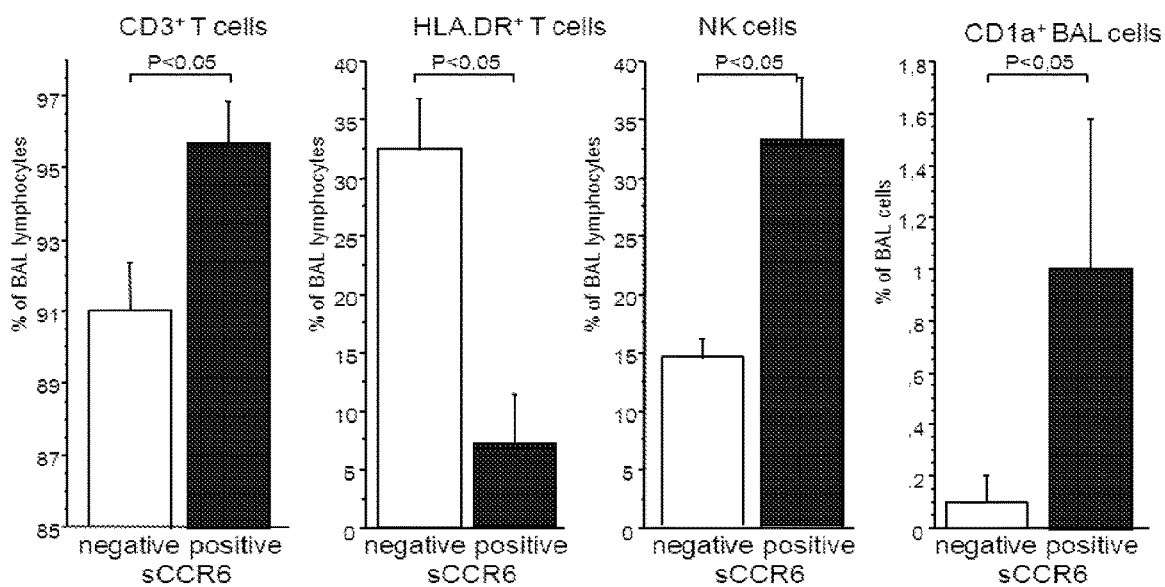

FIG. 22 Percentage of CD3+ and HLA-DR+ lymphocytes, NK-cells and CD1a+ dendritic cells in BAL from sCCR6 positive and sCCR6 negative (UIP) patients.

Figure 23:
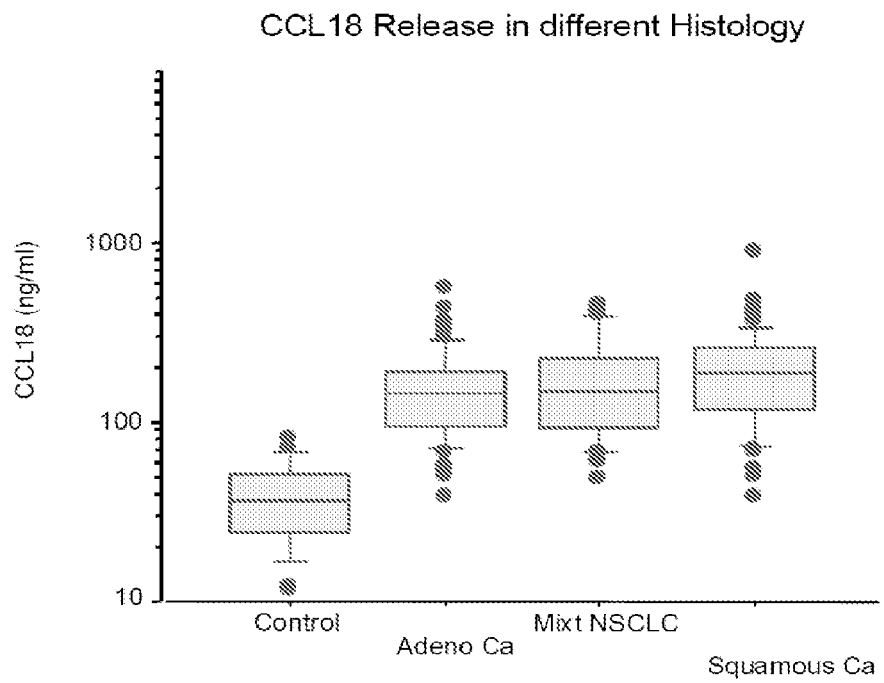

FIG. 23 All patient groups disclosed a significantly increased CCL18 serum level compared with controls.

Figure 24:
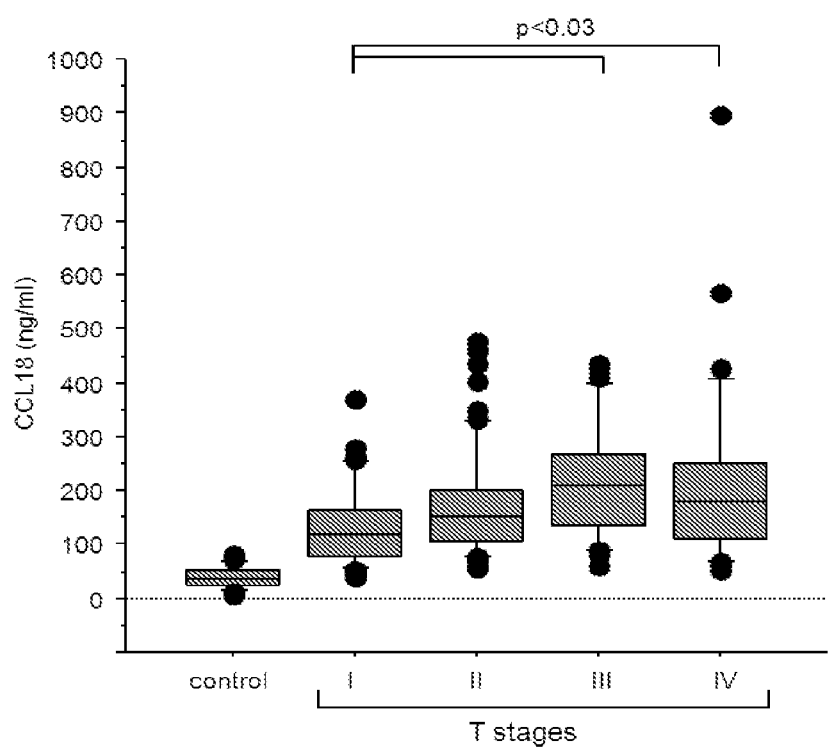

FIG. 24 Mean CCL18 levels of all T stages was significantly increased compared with controls (p<0.0002). In addition, there was a significant difference between patient groups with lowest versus the two highest T-stages.

Figure 25:
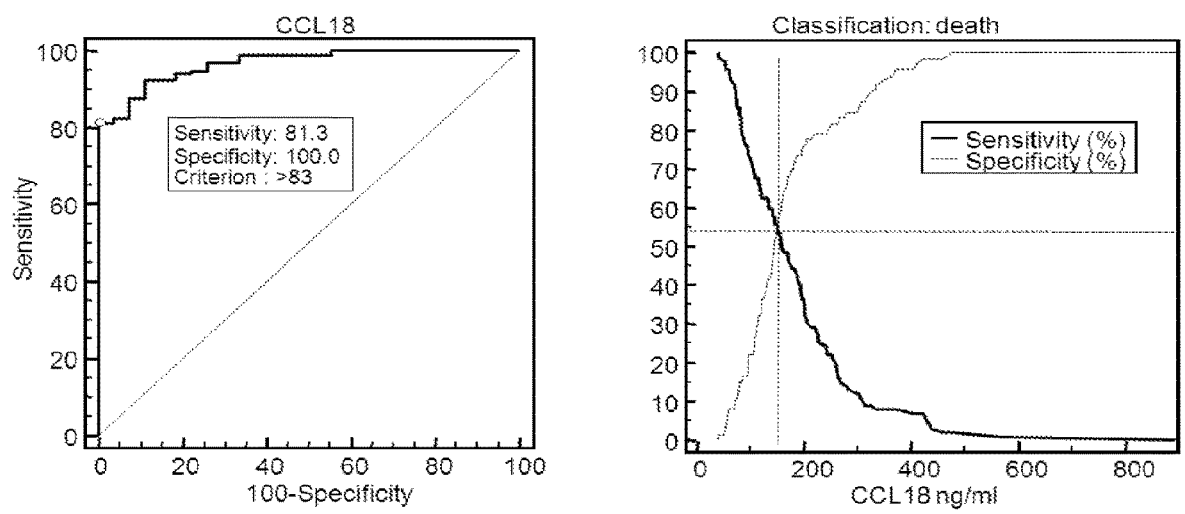

FIG. 25 Determination of cut off points using receiver/operator curve (ROC, left) and plots versus criterion value (right). ROC analysis revealed a cut off point of 83 ng/ml to differentiate between controls and tumor patients. The criterion plot revealed a cut off point of 160 ng/ml for the criterion death within the observation period.

Figure 26:
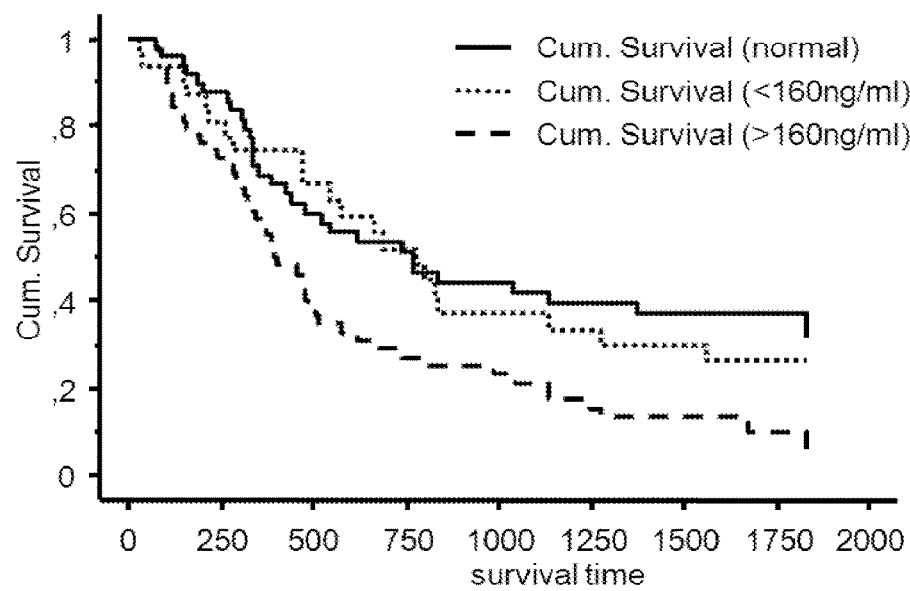

FIG. 26 Kaplan-Meier-Analysis of survival time of patients with NSCLC in relation to the CCL18 serum level.

Figure 27:
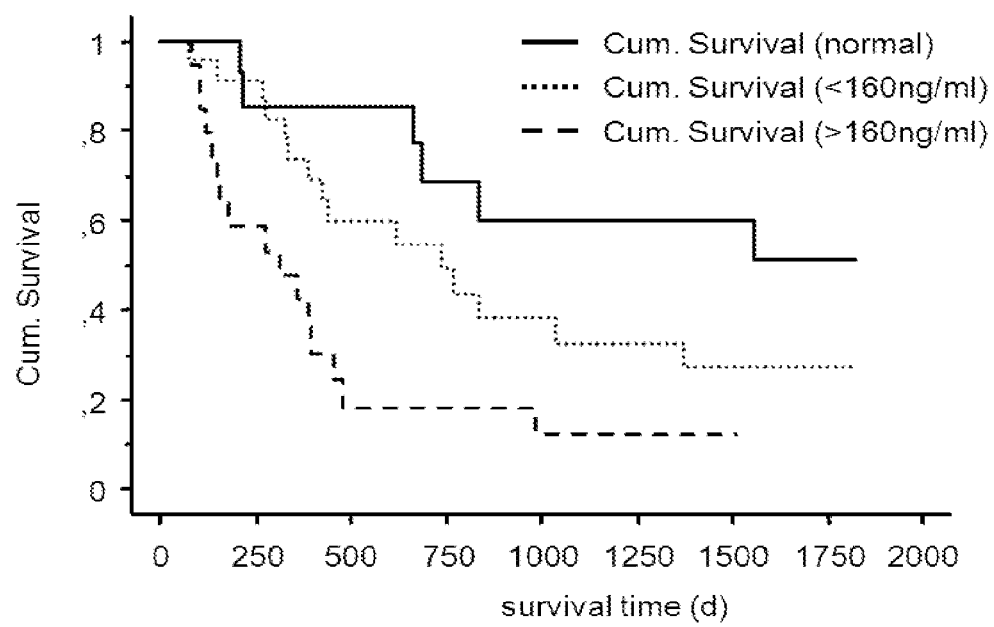

FIG. 27 Kaplan-Meier-Analysis of survival time of patients suffering from adenocarcinoma in relation to the CCL18 serum level.

Figure 28:
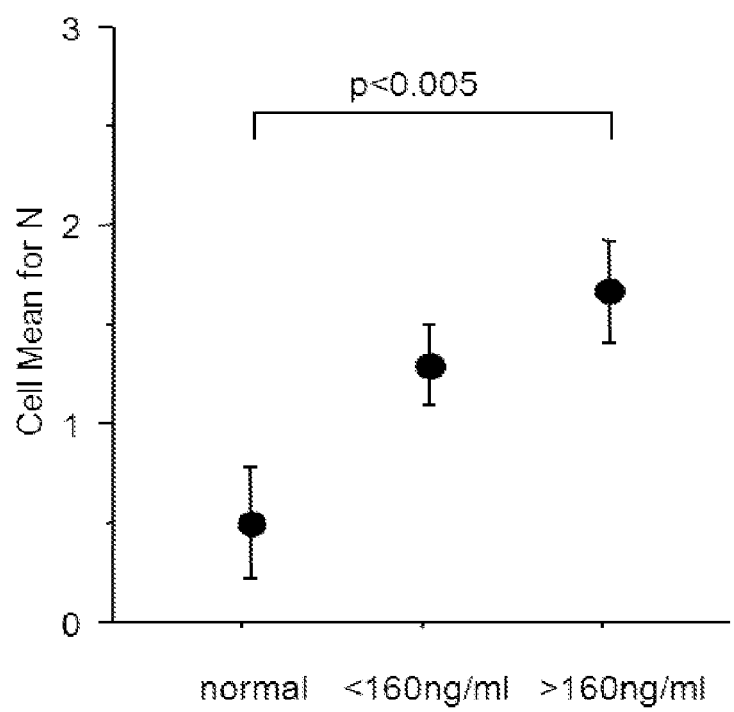

FIG. 28 In the subgroup of adenocarcinoma patients the mean N-stages in the group with the highest serum CCL18 levels are significantly higher as compared with the subgroup with normal serum CCL18 levels.

Figure 29:
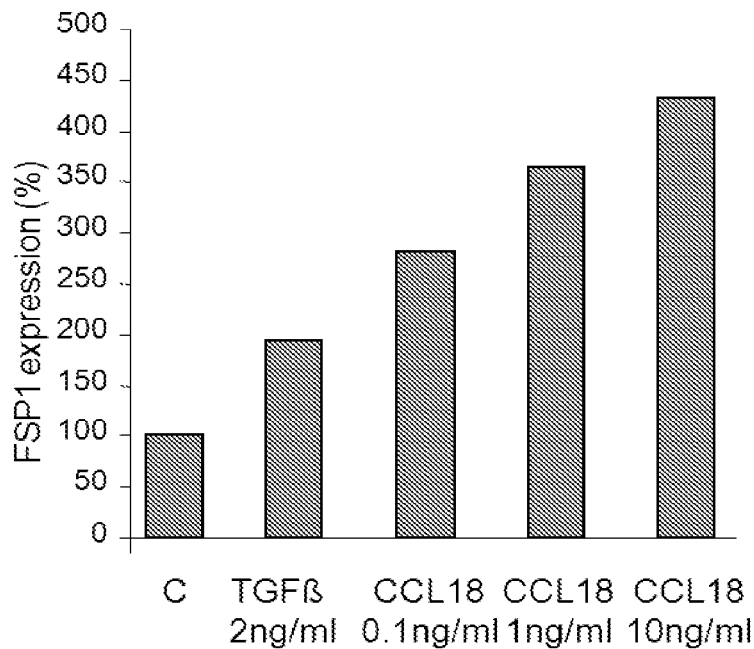

FIG. 29 CCL18 induces an up-regulation of FSP1 expression in adenocarcinoma cells (A549). TGFb was used at 2 ng/ml. The expression was determined by qPCR after 72 h of culture. (C=non-stimulated cells).

Figure 30:
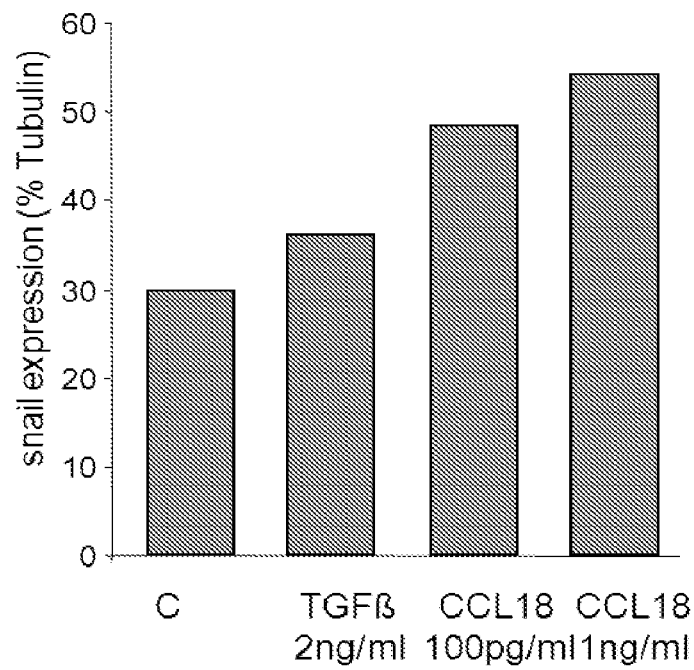

FIG. 30 CCL18 induces snail expression in adenocarcinoma cells (A549). TGFb was used at 2 ng/ml. The expression was determined by western blot after 72 h of culture. (C=non-stimulated cells).

Figure 31:
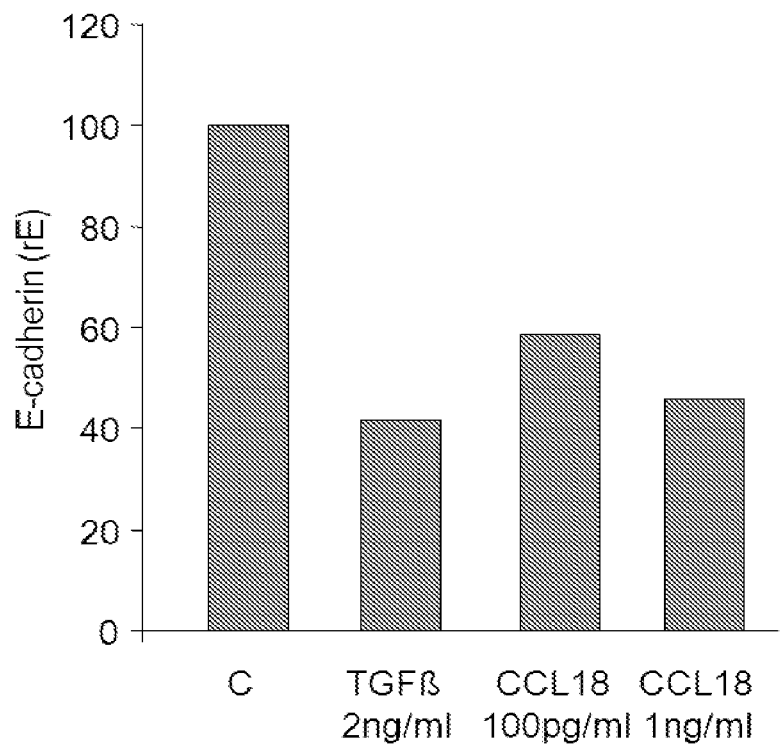

FIG. 31 CCL18 induces the down-regulation of E-cadherin expression in adenocarcinoma cells (A549). TGFb was used at 2 ng/ml. The expression was determined qPCR after 72 h of culture. (C=non-stimulated cells).

Figure 32:
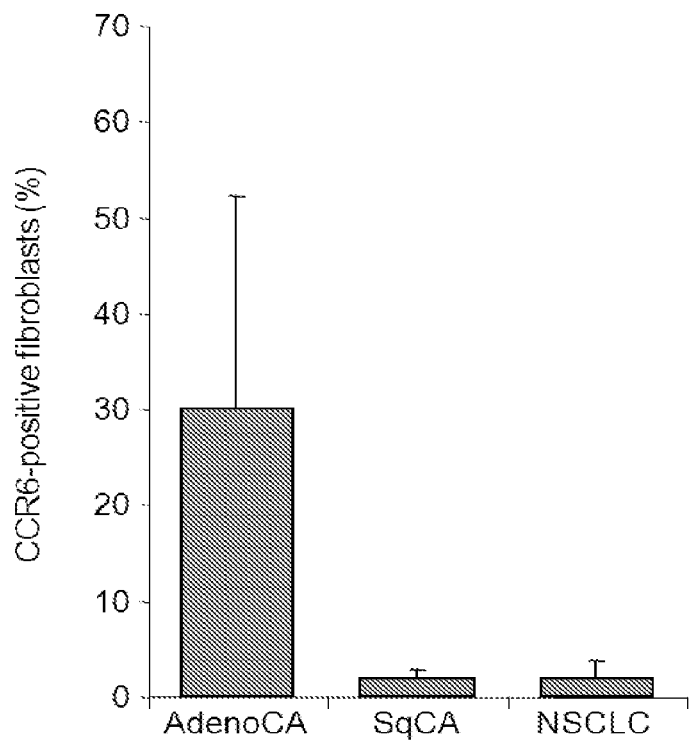

FIG. 32 Percentage of CCR6 positive fibroblast within fibroblast lines derived from lungs of patients suffering from different tumours.

FIG. 33 Sequence listing SEQ ID NO: 1 to 9 and SEQ ID NO: 18-27.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Although several documents are cited throughout the text of this specification, which are incorporated by reference in their entirety, nothing herein is to be construed as an admission that the invention is not entitled to antedate such disclosure by virtue of prior invention.

The following definitions are introduced. As used in this specification and in the intended claims, the singular forms of "a" and "an" also include the respective plurals unless the context clearly dictates otherwise.

It is to be understood that the term "comprise", and variations such as "comprises" and "comprising" is not limiting. For the purpose of the present invention the term "consisting of" is considered to be a preferred embodiment of the term "comprising".

If hereinafter a group is defined to comprise at least a certain number of embodiments, this is meant to also encompass a group which preferably consists of these embodiments only.

The terms "about" and "approximately" in the context of the present invention denote an interval of accuracy that a person skilled in the art will understand to still ensure the technical effect of the feature in question. The term typically encompasses a deviation from the indicated numerical value of ±10% and preferably of ±5%.

üThe determination of percent identity between two sequences is preferably accomplished using the mathematical algorithm of Karlin and Altschul (1993) Proc. Natl. Acad. Sci USA 90: 5873-5877. Such an algorithm is e.g. incorporated into the BLASTn and BLASTp programs of Altschul et al. (1990) J. MoI. Biol. 215: 403-410 available at NCBI (http://www.ncbi.nlm.nih.gov/blast/Blast.cgi).

The determination of percent identity is preferably performed with the standard parameters of the BLASTn and BLASTp programs.

BLAST polynucleotide searches are preferably performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters, the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "Mask lower case letters" box may not be ticked.

BLAST protein searches are preferably performed with the BLASTp program.

For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

The percent identity is determined over the entire length of the respective reference sequence, i.e. over the entire length of the sequence according to the SEQ ID NO or SEQ ID NOs recited in the respective context. For example, an amino acid sequence which exhibits at least 80% identity to the sequence according to SEQ ID NO.:1 exhibits at least 80% identity to SEQ ID NO.:1 over the entire length of SEQ ID NO.:1. In another example, a sequence which exhibits at least 80% identity to the sequence according to SEQ ID NO.:8 exhibits at least 80% identity to SEQ ID NO.:8 over the entire length of SEQ ID NO.:8.

The term "subject" as used herein refers to a human or an animal, preferably a mammal such as e.g. non-human primates, mice, rats, rabbits, guinea pigs, dogs, cats, cattle, horses, sheep, pigs, goats and the like. Preferably a "subject" in the context of the present invention is a human.

The terms "chemokine receptor CCR6" or "CCR6 receptor", "Chemokine ligand 18" or "CCL18" and "Chemokine ligand 20" or "CCL20" mentioned in the context of the present invention are well known in the art. Therefore, the average skilled person can easily retrieve the polynucleotide and amino acid sequences of CCR6 receptor, CCL18 and CCL20 and orthologous and splice isoforms thereof from any suitable public database such as e.g. the NCBI database (http://www.ncbi.nlm.nih.gov/pubmed/). The terms "CCR6 receptor" and "CCR6" are used interchangeably herein.

"CCR6 receptor", "CCL18" and "CCL20" as mentioned in the context of the present invention are preferably mammalian CCR6 receptor, CCL18 and CCL20, most preferably human CCR6 receptor and human CCL18 or human CCL20. Human CCR6 receptor can e.g. be found in the NCBI database under accession number NM_004367.5 (transcript variant 1; SEQ ID NO.:3) or NM_031409.3 (transcript variant 2; SEQ ID NO.:4). Human CCL18 can e.g. be found in the NCBI database under accession number NM_002988.2 (SEQ ID NO.:5). Human CCL20 can e.g. be found in the NCBI database under accession number NM_004591.2 (transcript variant 1; SEQ ID NO.:6) or NM_001130046.1 (transcript variant 2; SEQ ID NO.:7).

CCR6 is sometimes also referred to as CD196. CCL18 is sometimes also referred to as pulmonary and activation-regulated chemokine (PARC), alternative macrophage activation-associated CC chemokine 1 (AMAC-1), macrophage inflammatory protein-4 (MIP-4) or dendritic cell-derived chemokine1 (DCCK1).

The terms "IPF" (idiopathic pulmonary fibrosis) and "UIP" (usual interstitial pneumonia) are used synonymously herein.

The inventors of the present invention surprisingly found that CCL18 is a ligand/an agonist of CCR6 receptor, a member of the seven-transmembrane G-protein-coupled chemokine receptor family. The inventors further surprisingly found that a soluble CCR6 receptor polypeptide can be found in serum from healthy human volunteers but can only be detected in reduced amounts or not at all in serum from human patients suffering from IPF. The inventors also found that an isolated soluble CCR6 receptor polypeptide can be used in therapy, in particular for the therapy of an interstitial lung disease or cancer. The inventors further surprisingly found that inhibitors of CCR6 receptor activity can be used for the therapy of an interstitial lung disease or cancer.

Therefore, in one aspect the present invention relates to an isolated soluble CCR6 receptor polypeptide comprising or consisting of an amino acid sequence selected from the group consisting of:
(a) an amino acid sequence which exhibits at least 80% identity to the sequence according to SEQ ID NO.: 1; and
(b) a fragment of the amino acid sequence according to (a);
wherein said isolated soluble CCR6 receptor polypeptide is capable of binding to CCL18 and/or CCL20.

In a preferred embodiment, the isolated soluble CCR6 receptor polypeptide according to the invention further comprises an amino acid sequence, which exhibits at least 80%, 85%, 90%, 95% or 98% identity to the sequence according to SEQ ID NO.: 2 or a fragment thereof. In a particularly preferred embodiment the isolated soluble CCR6 receptor polypeptide according to the invention further comprises an amino acid sequence, which exhibits at least 95% identity to the sequence according to SEQ ID NO.: 2 or a fragment thereof. In another particularly preferred embodiment the isolated soluble CCR6 receptor polypeptide according to the invention further comprises the amino acid sequence according to SEQ ID NO.: 2 or a fragment thereof. In another preferred embodiment, the isolated soluble CCR6 receptor polypeptide according to the invention comprises or consists of an amino acid sequence which exhibits at least 80% identity to the sequence according to SEQ ID NO.: 1 or a fragment thereof and an amino acid sequence which exhibits at least 80% identity to the sequence according to SEQ ID NO.: 2 or a fragment thereof. In yet another preferred embodiment, the isolated soluble CCR6 receptor polypeptide according to the invention comprises or consists of an amino acid sequence which exhibits at least 90% identity to the sequence according to SEQ ID NO.: 1 or a fragment thereof and an amino acid sequence which exhibits at least 90% identity to the sequence according to SEQ ID NO.: 2 or a fragment thereof. In still another preferred embodiment the isolated soluble CCR6 receptor polypeptide according to the invention comprises or consists of an amino acid sequence which exhibits at least 95% identity to the sequence according to SEQ ID NO.: 1 or a fragment thereof and an amino acid sequence which exhibits at least 95% identity to the sequence according to SEQ ID NO.: 2 or a fragment thereof.

In yet another preferred embodiment the isolated soluble CCR6 receptor polypeptide according to the invention comprises or consists of an amino acid sequence according to SEQ ID NO.: 1 or a fragment thereof and an amino acid sequence according to SEQ ID NO.: 2 or a fragment thereof.

Preferably, CCL18 and/or CCL20 are human CCL18 and/or human CCL20. Most preferably said CCL18 is a polypeptide according to SEQ ID NO.: 18 and said CCL20 is a polypeptide according to SEQ ID NO.: 19.

The term "isolated" in the context of the present invention indicates that a polypeptide or polynucleotide has been removed from its natural environment and/or is presented in a form in which it is not found in nature. An "isolated" polypeptide or an "isolated" polynucleotide may also be a polypeptide or polynucleotide that has been generated in vitro.

The term "isolated soluble CCR6 receptor polypeptide" as used herein is meant to distinguish the isolated soluble CCR6 receptor polypeptide according to the invention from membrane-bound receptor polypeptides, such as e.g. membrane-bound CCR6 receptor. For example, in the context of the present invention any naturally occurring soluble CCR6 receptor polypeptide that under endogenous conditions is solved in a body fluid of a subject (such as e.g. serum, plasma, bronchoalveolar lavage fluid, pleural effusion, sputum, saliva or urine) and is not embedded in or attached to a cellular membrane is considered to be "soluble".

Thus, in one example, the isolated soluble CCR6 receptor polypeptide according to the invention may be a naturally occurring soluble CCR6 receptor polypeptide that has been isolated from a sample from a subject.

In another example, an isolated soluble CCR6 receptor polypeptide according to the invention may also be a recombinant polypeptide that has been generated in vitro and that is substantially soluble in aqueous solutions, such as e.g. physiological aqueous solutions, preferably in serum, plasma, bronchoalveolar lavage fluid, pleural effusion, sputum, saliva or urine. Most preferably in serum.

In a preferred embodiment, the isolated soluble CCR6 receptor polypeptide according to the invention is at least 50%, preferably at least 60%, more preferably at least 70%, more preferably at least 75%, more preferably at least 80%, more preferably at least 85% or most preferably at least 90% soluble in an aqueous solution, preferably in serum, plasma, bronchoalveolar lavage fluid, pleural effusion, sputum, saliva or urine. In a particularly preferred embodiment, the isolated soluble CCR6 receptor polypeptide according to the invention is at least 75% soluble in an aqueous solution, preferably in serum, plasma, bronchoalveolar lavage fluid, pleural effusion, sputum, saliva or urine. In order to determine percent solubility of an isolated soluble CCR6 polypeptide according to the invention, the skilled person may e.g. centrifuge a sample containing said polypeptide and subsequently measure the amount of the polypeptide in the supernatant and the total amount of the polypeptide in the sample. The percent solubility may then be calculated as percent of amount of polypeptide in the supernatant to total amount of polypeptide in the sample before centrifugation.

In a preferred embodiment, solubility of the isolated soluble CCR6 receptor polypeptide according to the invention in the aforementioned aqueous solutions does not require the addition of detergents. In another preferred embodiment, the isolated soluble CCR6 receptor polypeptide according to the invention does not comprise a transmembrane domain.

In one preferred embodiment the amino acid sequence according to (a) exhibits at least 85%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.: 1.

In a particularly preferred embodiment the amino acid sequence according to (a) exhibits 90%, 95% or 100% identity to the sequence according to SEQ ID NO.:1.

In another particularly preferred embodiment the amino acid sequence according to (a) is the sequence according to SEQ ID NO.:1. If the isolated soluble CCR6 receptor polypeptide according to the invention consists of an amino acid sequence according to SEQ ID NO.:1, the isolated soluble CCR6 receptor polypeptide according to the invention preferably has a length of 48 amino acids.

In another preferred embodiment in the amino acid sequence according to (a) not more than 1, 2, 3, 4, 5, 6, 7, 8, 9 or 10 amino acids of the sequence according to SEQ ID NO:1 are changed (i.e. deleted, inserted, modified and/or substituted by other amino acids).

A substitution in an amino acid sequence according to the invention may be a conservative or a non-conservative substitution, preferably a conservative substitution. In some embodiments, a substitution also includes the exchange of a naturally occurring amino acid with a non-natural amino acid. A conservative substitution comprises the substitution of an amino acid with another amino acid having a chemical property similar to the amino acid that is substituted. Preferably, the conservative substitution is a substitution selected from the group consisting of:
(i) a substitution of a basic amino acid with another, different basic amino acid;
(ii) a substitution of an acidic amino acid with another, different acidic amino acid;
(iii) a substitution of an aromatic amino acid with another, different aromatic amino acid;
(iv) a substitution of a non-polar, aliphatic amino acid with another, different non-polar, aliphatic amino acid; and
(v) a substitution of a polar, uncharged amino acid with another, different polar, uncharged amino acid.

A basic amino acid is preferably selected from the group consisting of arginine, histidine, and lysine. An acidic amino acid is preferably aspartate or glutamate.

An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of an amino acid with any amino acid that does not fall under the above-outlined conservative substitutions (i) through (v).

Amino acids of the isolated soluble CCR6 polypeptide according to the invention may also be modified, e.g. chemically modified. For example, the side chain or a free amino or carboxy-terminus of an amino acid of the protein may be modified by e.g. glycosylation, amidation, phosphorylation, ubiquitination, etc. In order to increase intracellular stability and/or to reduce a subject's immune response to the isolated soluble CCR6 polypeptide according to the invention, the isolated soluble CCR6 polypeptide according to the invention, may e.g. be modified by acetylation, PEGylation, amidation or D-amino acid incorporation.

In a preferred embodiment the amino acid sequence according to (a) comprises at least 8, at least 9, at least 10, at least 11, at least 12, at least 13, at least 14, at least 15, at least 16, at least 17, at least 18, at least 19, at least 20, at least 25, at least 30, at least 35, at least 40 or at least 45 consecutive amino acids of the sequence according to SEQ ID NO.:1. In a particularly preferred embodiment the amino acid sequence according to (a) comprises at least 8, at least 15, at least 20, at least 30 or at least 40 amino of the sequence according to SEQ ID NO.:1.

In another preferred embodiment the amino acid sequence according to (a) exhibits at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, even more preferably at least 99% or most preferably 100% identity to the sequence according to SEQ ID NO.:1 and comprises at least 8, more preferably at least 12, more preferably at least 15, more preferably at least 20, more preferably at least 25, more preferably at least 30, more preferably at least 35, more preferably at least 40 and most preferably at least 45 consecutive amino acids of the sequence according to SEQ ID NO.:1.

In yet another preferred embodiment the amino acid sequence according to (a) exhibits at least 95% or at least 98% identity to the sequence according to SEQ ID NO.:1 and comprises at least 20, at least 25, at least 30 or at least 40 consecutive amino acids of the sequence according to SEQ ID NO.:1. In a most preferred embodiment the amino acid sequence according to (a) exhibits at least 95% identity to the sequence according to SEQ ID NO.:1 and comprises at least 20 consecutive amino acids of the sequence according to SEQ ID NO.:1 or exhibits at least 98% identity to the sequence according to SEQ ID NO.:1 and comprises at least 25 consecutive amino acids of the sequence according to SEQ ID NO.:1.

In a preferred embodiment, the isolated soluble CCR6 receptor polypeptide according to the invention has a length of less than 3000 amino acids, preferably less than 2000 amino acids, more preferably less than 1000 amino acids, more preferably less than 500 amino acids, more preferably less 300 amino acids, more preferably less than 200 amino acids, more preferably less than 100 amino acids or most preferably less than 80 amino acids.

In a further preferred embodiment the isolated soluble CCR6 receptor polypeptide according to the invention has a length of between at least 8 and at least 3000 amino acids, preferably between at least 8 and at least 2000 amino acids, more preferably between at least 8 and at least 1000 amino acids, more preferably between at least 8 and 500 amino acids, more preferably between at least 8 and 300 amino acids, more preferably between at least 8 and 200 amino acids, and even more preferably between at least 8 and 100 amino acids or between at least 8 and 80 amino acids.

In another preferred embodiment the isolated soluble CCR6 receptor polypeptide according to the invention has a length of between at least 20 and at least 3000 amino acids, preferably between at least 20 and at least 2000 amino acids, more preferably between at least 20 and at least 1000 amino acids, more preferably between at least 20 and 500 amino acids, more preferably between at least 20 and 300 amino acids, more preferably between at least 20 and 200 amino acids, and even more preferably between at least 20 and 100 amino acids or between at least 20 and 80 amino acids. In another preferred embodiment the isolated soluble CCR6 receptor polypeptide according to the invention has a length of between at least 30 and at least 3000 amino acids, preferably between at least 30 and at least 2000 amino acids, more preferably between at least 30 and at least 1000 amino acids, more preferably between at least 30 and 500 amino acids, more preferably between at least 30 and at least 300 amino acids, more preferably between at least 30 and 200 amino acids, and even more preferably between at least 30 and 100 amino acids or between at least 30 and 80 amino acids.

In a further preferred embodiment the isolated soluble CCR6 receptor polypeptide according to the invention has a length of between at least 40 and at least 3000 amino acids, preferably between at least 40 and at least 2000 amino acids, more preferably between at least 40 and at least 1000 amino acids, more preferably between at least 40 and 500 amino acids, more preferably between at least 40 and 300 amino acids, more preferably between at least 40 and 200 amino acids, and even more preferably between at least 40 and 100 amino acids or between at least 40 and 80 amino acids. In yet another preferred embodiment the isolated soluble CCR6 receptor polypeptide according to the invention has a length of between at least 50 and at least 3000 amino acids, preferably between at least 50 and at least 2000 amino acids, more preferably between at least 50 and at least 1000 amino acids, more preferably between at least 50 and 500 amino acids, more preferably between at least 50 and 300 amino acids, more preferably between at least 50 and 200 amino acids, and even more preferably between at least 50 and 100 amino acids or between at least 50 and 80 amino acids. In a particularly preferred embodiment the isolated soluble CCR6 receptor polypeptide according to the invention has a length of between at least 20 and at least 500 amino acids.

In another preferred embodiment, the isolated soluble CCR6 receptor polypeptide according to the invention has a length of at least 8, more preferably at least 10, more preferably at least 20, more preferably at least 30, more preferably at least 40, more preferably at least 45 and even more preferably at least 48 amino acids. In a particularly preferred embodiment, the isolated soluble CCR6 receptor polypeptide according to the invention has a length of at least 30, at least 40 or at least 48 amino acids. In a particularly preferred embodiment the isolated soluble CCR6 receptor polypeptide according to the invention has a length of 48 amino acids.

A fragment is typically a portion of the amino acid sequence it refers to.

In a preferred embodiment the fragment according to (b) is at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 or at least 28 amino acids in length. In a preferred embodiment the fragment according to (b) has a length of at least 10, at least 15 or at least or at least 20 amino acids. In a particularly preferred embodiment the fragment according to (b) has a length of at least 15 amino acids, more preferably at least 20, more preferably at least 30 or most preferably at least 40 amino acids. In a further particularly preferred embodiment the fragment according to (b) has a length of at least 40 amino acids.

Whether an isolated soluble CCR6 receptor polypeptide according to the invention is capable of binding to CCL18 and/or CCL20 may be determined by any suitable method known to the skilled person. For example, the skilled person may determine whether a soluble CCR6 receptor polypeptide according to the invention is capable of binding to CCL18 and/or CCL20 by using a yeast two-hybrid assay or a biochemical assay such as e.g. a pull-down assay, a co-immunoprecipitation assay, an enzyme-linked immunosorbent assay (ELISA), a quantitative radioligand binding assay, a Plasmon resonance assay or any other method known to the skilled person. When using pull-down or Plasmon resonance assays, it is useful to fuse at least one of the proteins to an affinity tag such as HIS-tag, GST-tag or other, as is well known in the art of biochemistry.

In a preferred embodiment, the isolated soluble CCR6 receptor polypeptide according to the invention is capable of inhibiting the activity of CCL18 and/or CCL20.

The term "inhibiting the activity of CCL18 and/or CCL20" as used herein means that the activity of CCL18 and/or CCL20 is downregulated or abolished by the isolated soluble CCR6 receptor polypeptide according to the invention or any other compound capable of inhibiting the activity of CCL18 and/or CCL20 described herein (such as e.g. an antibody specific for CCL18 and/or CCL20).

For example, in one embodiment the isolated soluble CCR6 receptor polypeptide according to the invention or any other compound capable of inhibiting the activity of CCL18 and/or CCL20 described herein upon binding to CCL18 and/or CCL20 may inhibit the interaction of CCL18 and/or CCL20 with membrane-bound CCR6 receptor, such that CCL18 or CCL20 cannot activate said receptor. Thus, an inhibition of CCL18 and/or CCL20 activity may e.g. be due to an inhibition of the interaction of CCL18 and/or CCL20 with membrane-bound CCR6 receptor. In another embodiment, the isolated soluble CCR6 receptor polypeptide according to the invention or any other compound capable of inhibiting the activity of CCL18 and/or CCL20 described herein upon binding to CCL18 and/or CCL20 may inhibit the chemotactic activity of CCL18 and/or CCL20. In a further preferred embodiment, the isolated soluble CCR6 receptor polypeptide according to the invention or any other compound capable of inhibiting the activity of CCL18 and/or CCL20 described herein upon binding to CCL18 and/or CCL20 may inhibit the interaction of CCL18 and/or CCL20 with membrane-bound CCR6 receptor and the chemotactic activity of CCL18 and/or CCL20. The isolated soluble CCR6 receptor polypeptide according to the invention or any other compound capable of inhibiting the activity of CCL18 and/or CCL20 described herein may e.g. inhibit the activity of CCL18 and/or CCL20 by sequestering said proteins and thus reducing their bioavailability.

Whether the isolated soluble CCR6 receptor polypeptide according to the invention or any other compound to be tested is capable of inhibiting the activity of the CCR6 receptor ligands CCL18 and/or CCL20 may e.g. be determined by measuring the activity of membrane-bound CCR6 receptor.

In one example, the skilled person may e.g. determine the ability of the isolated soluble CCR6 receptor polypeptide according to the invention or any other compound to be tested to inhibit CCL18 and/or CCL20 activity by incubating cells expressing membrane-bound CCR6 receptor in the presence of CCL18 or CCL20, and in the presence or absence of the isolated soluble CCR6 receptor polypeptide according to the invention or any other compound to be tested and subsequently lysing the cells and analyzing phosphorylation of ERK, a downstream molecule of CCR6 signaling, by Western blot analysis. In this example a lower level of phosphorylation of ERK in the presence of the isolated soluble CCR6 receptor polypeptide according to the invention or any other compound to be tested versus the level of phosphorylation of ERK in the absence of the isolated soluble CCR6 receptor polypeptide according to the invention or any other compound to be tested indicates that the isolated soluble CCR6 receptor polypeptide according to the invention or the other compound tested is capable of inhibiting the activation of membrane-bound CCR6 receptor by CCL18 and/or CCL20. One method for determining ERK phosphorylation by Western Blot analysis is e.g. described in Lin et al. J Proteome Res. 2010 January; 9(1):283-97. In an analogous example, the phosphorylation of other CCR6 receptor downstream effectors such as e.g. Akt, SAPK/JNK kinases, phosphatidylinositol 3-kinase or phospholipase C may be analysed in order to determine whether the isolated soluble CCR6 receptor polypeptide according to the invention or any other compound to be tested is capable of inhibiting CCL18 and/or CCL20 activity.

Whether the isolated soluble CCR6 polypeptide according to the invention or any other compound to be tested is capable of inhibiting the activity of CCL18 and/or CCL20 may e.g. also be determined by measuring the chemotactic activity of CCL18 and/or CCL20.

The chemotactic activity of CCL18 and/or CCL20 may e.g. be determined by performing chemotaxis assays in the presence or absence of the isolated soluble CCR6 receptor polypeptide according to the invention or any other compound to be tested. The skilled person may e.g. perform a chemotaxis chamber assay. An example of such an essay is e.g. described in Christopherson et al. J Pharmacol Exp Ther. 2002 July; 302(1):290-5. A reduced chemotactic activity of CCL18 and/or CCL20 in the presence of the isolated soluble CCR6 receptor polypeptide according to the invention or other compound to be tested indicates that the isolated soluble CCR6 receptor polypeptide according to the invention or the other compound tested is capable of inhibiting the chemotactic activity of CCL18 and/or CCL20.

Furthermore, whether the isolated soluble CCR6 polypeptide according to the invention or any other compound to be tested is capable of inhibiting the activity of CCL18 may e.g. also be determined by measuring CCL18 stimulated FGF2 release or CCL18 mediated induction of collagen and/or α-SMA in the presence of said isolated soluble CCR6 polypeptide or other compound. In this example an inhibition of CCL18 induced FGF2 upregulation and/or an inhibition of the CCL18 mediated induction of collagen and/or α-SMA expression in the presence of the isolated soluble CCR6 polypeptide or other compound to be tested in comparison to a control, to which the isolated soluble CCR6 polypeptide other compound has not been added, indicates that the isolated soluble CCR6 polypeptide or other compound is capable of inhibiting the activity of CCL18. In addition, in order to determine the ability of the isolated soluble CCR6 polypeptide according to the invention or any other compound to be tested to inhibit the activity of CCL18, the skilled person may also determine whether the induction of Epithelial-Mesenchymal-Transition (EMT) by CCL18 is downregulated or abolished.

Alternatively or additionally any further methods which are suited to determine the activity of CCL18 and/or CCL20 and which are comprised in the art and known to the average skilled person may be used.

The isolated soluble CCR6 receptor polypeptide according to the invention or any other compound which is capable of inhibiting the activity of CCL18 and/or CCL20, may inhibit the activity of CCL18 and/or CCL20 by at least 10%, at least 20%, at least 30%, at least 40%, at least 50%, at least 60%, at least 70%, more preferably at least 80%, at least 90%, at least 91%, at least 92%, at least 93%, at least 94%, at least 95%, at least 96%, at least 97%, at least 98% or at least 99% when compared to a control. In a preferred embodiment, the isolated soluble CCR6 receptor polypeptide according to the invention or any other compound which is capable of inhibiting the activity of CCL18 and/or CCL20 inhibits the activity of CCL18 and/or CCL20 by at least 50%, at least 60% or at least 70%. In another preferred embodiments the isolated soluble CCR6 receptor polypeptide according to the invention or any other compound described herein, which is capable of inhibiting the activity of CCL18 and/or CCL20, may inhibit the activity of CCL18 and/or CCL20 by 100%.

In another preferred embodiment, the isolated soluble CCR6 receptor polypeptide according to the invention does not comprise a transmembrane domain.

The term "transmembrane domain" is used herein according to its conventional and well known meaning in the art. A transmembrane domain may e.g. be a portion of a protein which comprises a high percentage of non-polar, hydrophobic amino acid residues, such as e.g. valine, leucine, isoleucine, tyrosine, phenylalanine or tryptophane, and that provides for partitioning of a protein into a lipid bilayer membrane. The term "high percentage of non-polar, hydrophobic amino acid residues" means that at least 50%, preferably at least 60%, more preferably at least 70%, more preferably at least 80%, more preferably at least 90%, most preferably at least 95% or more of the amino acids of a transmembrane domain are non-polar, hydrophobic amino acid residues.

In another aspect the present invention relates to an isolated polynucleotide encoding the isolated soluble CCR6 receptor polypeptide according to the invention.

In a preferred embodiment, the isolated polynucleotide according to the invention has a length of less than 9000 nucleotides, less than 8000 nucleotides, less than 7000 nucleotides, less than 6000 nucleotides, less than 5000 nucleotides, less than 4000 nucleotides, less than 3000 nucleotides, less than 2000 nucleotides, less than 1000 nucleotides, less than 500 nucleotides or less than 300 nucleotides.

In a further preferred embodiment the isolated polynucleotide according to the invention has a length of between at least 24 and 9000 nucleotides, preferably at least 24 and 8000 nucleotides, more preferably between at least 24 and 7000 nucleotides, more preferably between at least 24 and 6000 nucleotides, more preferably between at least 24 and 5000 nucleotides, more preferably between at least 24 and 4000 nucleotides, more preferably between at least 24 and 3000 nucleotides, more preferably between at least 24 and 2000 nucleotides, more preferably between at least 24 and 1000 nucleotides or even more preferably between at least 24 and 500 nucleotides or even more preferably between at least 24 and 300 nucleotides. In another preferred embodiment the isolated polynucleotide according to the invention has a length of between at least 60 and 9000 nucleotides, preferably at least 60 and 8000 nucleotides, more preferably between at least 60 and 7000 nucleotides, more preferably between at least 60 and 6000 nucleotides, more preferably between at least 60 and 5000 nucleotides, more preferably between at least 60 and 4000 nucleotides, more preferably between at least 60 and 3000 nucleotides, more preferably between at least 60 and 2000 nucleotides, more preferably between at least 60 and 1000 nucleotides or even more preferably between at least 60 and 500 nucleotides or even more preferably between at least 60 and 300 nucleotides. In a further preferred embodiment the isolated polynucleotide according to the invention has a length of between at least 90 and 9000 nucleotides, preferably at least 90 and 8000 nucleotides, more preferably between at least 90 and 7000 nucleotides, more preferably between at least 90 and 6000 nucleotides, more preferably between at least 90 and 5000 nucleotides, more preferably between at least 90 and 4000 nucleotides, more preferably between at least 90 and 3000 nucleotides, more preferably between at least 90 and 2000 nucleotides, more preferably between at least 90 and 1000 nucleotides or even more preferably between at least 90 and 500 nucleotides or even more preferably between at least 90 and 300 nucleotides. In yet another preferred embodiment the isolated polynucleotide according to the invention has a length of between at least 120 and 9000 nucleotides, preferably at least 120 and 8000 nucleotides, more preferably between at least 120 and 7000 nucleotides, more preferably between at least 120 and 6000 nucleotides, more preferably between at least 120 and 5000 nucleotides, more preferably between at least 120 and 4000 nucleotides, more preferably between at least 120 and 3000 nucleotides, more preferably between at least 120 and 2000 nucleotides, more preferably between at least 120 and 1000 nucleotides or even more preferably between at least 120 and 500 nucleotides or even more preferably between at least 120 and 300 nucleotides. In yet another preferred embodiment the isolated polynucleotide according to the invention has a length of between at least 140 and 9000 nucleotides, preferably at least 140 and 8000 nucleotides, more preferably between at least 140 and 7000 nucleotides, more preferably between at least 140 and 6000 nucleotides, more preferably between at least 140 and 5000 nucleotides, more preferably between at least 140 and 4000 nucleotides, more preferably between at least 140 and 3000 nucleotides, more preferably between at least 140 and 2000 nucleotides, more preferably between at least 140 and 1000 nucleotides or even more preferably between at least 140 and 500 nucleotides or even more preferably between at least 140 and 300 nucleotides.

In another preferred embodiment an isolated polynucleotide according to the invention has a length of at least 24 nucleotides, at least 50 nucleotides, at least 60 nucleotides, at least 70 nucleotides, at least 80 nucleotides, at least 90 nucleotides, at least 100 nucleotides, at least 200 nucleotides, at least 500 nucleotides, at least 800 nucleotides, at least 1000 nucleotides, at least 1500 nucleotides, at least 2000 nucleotides, at least 2500 nucleotides, at least 3000 nucleotides or at least 3500 nucleotides. In a particularly preferred embodiment the isolated polynucleotide according to the invention has a length of at least 24, at least 50 nucleotides, at least 60 nucleotides, at least 70 nucleotides, at least 80 nucleotides, at least 90 nucleotides, at least 100 nucleotides, at least 200 nucleotides. In a particularly preferred embodiment an isolated polynucleotide according to the invention has a length of at least 140 nucleotides.

In another particularly preferred embodiment an isolated polynucleotide according to the invention has a length of 144 nucleotides.

It will be apparent to the skilled person that due to the degeneracy of the genetic code a given polypeptide according to the invention may be encoded by different nucleotide sequences.

In a preferred embodiment the isolated polynucleotide according to the invention comprises or consists of a sequence which exhibits at least 80% identity to the sequence according to SEQ ID NO.:8.

In a further preferred embodiment the isolated polynucleotide according to the invention comprises or consists of a sequence which exhibits at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:8. In a particularly preferred embodiment the polynucleotide according to the invention comprises or consists of a sequence which exhibits at least 85%, preferably at least 90%, more preferably at least 95% or even more preferably at least 98% identity to the sequence according to SEQ ID NO.:8.

In a particularly preferred embodiment the isolated polynucleotide according to the invention comprises or consists of a sequence which exhibits 100% identity to the sequence according to SEQ ID NO.:8. In another particularly preferred embodiment the isolated polynucleotide according to the invention comprises or consists of a sequence according to SEQ ID NO.:8.

An isolated polynucleotide according to the invention may be a single or double stranded RNA or DNA molecule.

In some embodiments the isolated polynucleotide according to the invention may be inserted into an expression vector. The expression vector may e.g. be a prokaryotic or eukaryotic expression vector such as e.g. a plasmid, a minichromosome, a cosmid, a bacterial phage, a retroviral vector or any other vector known to the skilled person. The skilled person will be familiar with how to select an appropriate vector according to the specific need.

The present invention thus also relates to an expression vector comprising a polynucleotide according to the invention.

In a further aspect the present invention relates to a method for quantifying the concentration of a soluble CCR6 receptor polypeptide in a liquid sample from a subject, wherein the method comprises the steps of:

(a) immobilizing a capture molecule for said soluble CCR6 receptor polypeptide on a solid support;

(b) adding the liquid sample from the subject;

(c) optionally adding a ligand of said soluble CCR6 receptor polypeptide, wherein said ligand is a polypeptide comprising or consisting of an amino acid sequence which exhibits at least 80% identity to the sequence according to SEQ ID NO.: 18, SEQ ID NO.: 19, SEQ ID NO.: 20 or SEQ ID NO.: 21;

(d) adding a detecting agent specific for a ligand according to (c), wherein the detecting comprises a label;

(e) quantifying the signal from the detecting agent according to (d).

In a preferred embodiment of the aforementioned method, the steps (a), (b), (c), (d), (e) are carried out in that order. The method is preferably performed in vitro.

The term "soluble CCR6 receptor polypeptide" as used herein is meant to refer to a CCR6 receptor polypeptide that is not embedded in or attached to a cellular membrane. A "soluble CCR6 receptor polypeptide" thus has to be distinguished from "membrane-bound CCR6 receptor". For example, in the context of the present invention any naturally occurring soluble CCR6 receptor polypeptide that under endogenous conditions is solved in a body fluid of a subject (such as e.g serum, plasma, bronchoalveolar lavage fluid, pleural effusion, sputum, saliva or urine) and is not embedded in or attached to a cellular membrane is considered to be "soluble".

Thus, in one example, a "soluble CCR6 receptor polypeptide" in the context of the aforementioned method according to the invention may be a naturally occurring soluble CCR6 receptor polypeptide. In one preferred embodiment said naturally occurring soluble CCR6 receptor polypeptide is detectable with an anti-CCR6 antibody directed to the N-terminal extracellular domain of CCR6.

In another preferred embodiment, the naturally occurring soluble CCR6 receptor polypeptide comprises or consists of an amino acid sequence selected from the group consisting of:

(a) an amino acid sequence which exhibits at least 80% identity to the sequence according to SEQ ID NO.: 1; and (b) a fragment of the amino acid sequence according to (a);

wherein said isolated soluble CCR6 receptor polypeptide is capable of binding to CCL18 and/or CCL20.

In one preferred embodiment the amino acid sequence according to (a) exhibits at least 85%, more preferably at least 90%, more preferably at least 95% or even more preferably at least 98% identity to the sequence according to SEQ ID NO.: 1. In a particularly preferred embodiment the amino acid sequence according to (a) exhibits at least 95% identity to the sequence according to SEQ ID NO.: 1. In a most preferred embodiment the amino acid sequence according to (a) exhibits 100% identity to the sequence according to SEQ ID NO.:1.

In another particularly preferred embodiment, the naturally occurring soluble CCR6 receptor polypeptide comprises or consists of an amino acid sequence according to SEQ ID NO.: 1.

In another example, a "soluble CCR6 receptor polypeptide" in the context of the aforementioned method of the invention may also be a recombinant "soluble CCR6 receptor polypeptide" that has been generated in vitro and that is substantially soluble in aqueous solutions, such as e.g. physiological aqueous solutions, preferably in serum, plasma, bronchoalveolar lavage fluid, pleural effusion, sputum, saliva or urine. In one preferred embodiment the soluble CCR6 receptor polypeptide is the isolated soluble CCR6 receptor polypeptide according to the invention.

Preferably, a "soluble CCR6 receptor polypeptide" in the context of the aforementioned method according to the invention is at least 50%, more preferably at least 60%, more preferably at least 70%, more preferably at least 75%, more preferably at least 80%, more preferably at least 85% or most preferably at least 90% soluble in an aqueous solution, preferably in serum, plasma, bronchoalveolar lavage fluid, pleural effusion, sputum, saliva or urine. In a particularly preferred embodiment, a "soluble CCR6 receptor polypeptide" in the context of the aforementioned method according to the invention is at least 75% soluble in an aqueous solution, preferably in serum, plasma, bronchoalveolar lavage fluid, pleural effusion, sputum, saliva or urine. In order to determine percent solubility of a "soluble CCR6 receptor polypeptide", the skilled person may e.g. centrifuge a sample containing soluble CCR6 receptor polypeptide and subsequently measure the amount of said polypeptide in the supernatant and the total amount of said polypeptide in the sample. The percent solubility may then be calculated as percent of amount of the CCR6 receptor polypeptide in the supernatant to total amount of CCR6 receptor polypeptide in the sample before centrifugation.

In one preferred embodiment of the aforementioned method according to the invention, the liquid sample from a subject is selected from the group consisting of serum, plasma, bronchoalveolar lavage fluid, pleural effusion, sputum, saliva and urine. In a particularly preferred embodiment the liquid sample from a subject is serum. Preferably, the sample is separated from the body of the subject it is derived from.

In a preferred embodiment said capture molecule in (a) and/or said detecting agent in (d) is an antibody or an aptamer.

An "aptamer" may be a DNA, RNA or peptide aptamer. A polynucleotide aptamer is preferably between about 10 to about 300 nucleotides in length. Preferably an aptamer is between about 30 to about 100 nucleotides in length. Most preferably an aptamer is between about 10 to 60 nucleotides in length. Aptamers may be prepared by any method known in the art, including e.g. synthetic, recombinant, and purification methods.

Preferably, the antibody is a monoclonal or polyclonal antibody. In some embodiments the antibody may also be selected from antibody variants or fragments such as e.g. single chain antibodies, diabodies, minibodies, single chain Fv fragments (sc(Fv)), sc(Fv)₂ antibodies, Fab fragments or a F(ab')₂ fragments. A capture molecule or a detecting agent is specific for a given compound, such as e.g. a soluble CCR6 receptor polypeptide or a ligand of a soluble CCR6 receptor polypeptide, if it binds said compound with a higher affinity than any other compound in a sample (i.e. a non-target). Preferably, a capture molecule or a detecting agent is specific for a given compound if it binds said compound only and does not bind at all to a non-target. The detecting agent in (d) comprises a label. Any suitable label, which can be attached to the detecting agent may be used. Preferably, the label is detectable or catalyzes an enzymatic reaction the product of which is detectable.

In one preferred embodiment the label is covalently or non-covalently attached to the detecting agent. Examples of labels that may be attached to the detecting agent include e.g. fluorescent dyes such as e.g. Cyanine dyes, e.g. Cyanine 3, Cyanine 5 or Cyanine 7, Alexa Fluor dyes, e.g. Alexa 594, Alexa 488 or Alexa 532, fluorescein family dyes, R-Phycoerythrin, Texas Red, rhodamine and Fluoresceinisothiocyanat (FITC). Detecting agents may also be labeled with enzymes such as e.g. horseradish peroxidase, alkaline phosphatase or beta-lactamase, radioisotopes such as e.g. $^3$H, $^{14}$C, $^{32}$P, $^{33}$P, $^{35}$S or $^{125}$I, metal such as e.g. gold or with biotin. In a particularly preferred embodiment, the label is a fluorescent label. In another embodiment the label may also be a secondary detecting agent comprising a label as described hereinbefore. Preferably a secondary detecting agent is capable of specifically binding to the above described detecting agent. In a particularly preferred embodiment a secondary detecting agent is an antibody.

In one preferred embodiment the detecting agent in (d) is specific for a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18, SEQ ID NO.: 19, SEQ ID NO.: 20 or SEQ ID NO.: 21. In a further preferred embodiment the detecting agent in (d) is specific for a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18. In another preferred embodiment the detecting agent in (d) is specific for a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 19. In still another preferred embodiment the detecting agent in (d) is specific for a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 20. In a further preferred embodiment the detecting agent in (d) is specific for a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 21.

In a most preferred embodiment the detecting agent in (d) is specific for a polypeptide comprising or consisting of an amino acid sequence which exhibits at least 85%, at least 90%, at least 95%, at least 96%, at least 97%, at least 98%, at least 99% identity to the sequence according to SEQ ID NO.: 18.

Preferably said solid support in (a) is a plastic or glass surface. In order to allow immobilization of a capture molecule on the solid support, the solid support may in some embodiments be pre-coated with a reagent selected from the group consisting of carbodiimines, imido- or succinimidylesters, ethanesulfonic acid, glutaraldehyde and polylysine.

In one preferred embodiment the aforementioned method according to the invention is performed in a mictotiter plate.

In another preferred embodiment the ligand according to (c) is a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18, SEQ ID NO.: 19, SEQ ID NO.: 20 or SEQ ID NO.: 21. In a further preferred embodiment the ligand according to (c) is a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18. In another preferred embodiment the ligand according to (c) is a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 19. In yet another preferred embodiment the ligand according to (c) is a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 20. In a further preferred embodiment the ligand according to (c) is a polypeptide comprising or consisting of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 21.

In a particularly preferred embodiment the ligand according to (c) is a polypeptide comprising or consisting of an amino acid sequence which exhibits 95%, at least 98% or 100% identity to the sequence according to SEQ ID NO.: 18, SEQ ID NO.: 19 or SEQ ID NO.: 20 or SEQ ID NO.: 21. In a further particularly preferred the ligand according to (c) is a polypeptide comprising or consisting of an amino acid sequence which exhibits 95%, at least 98% or 100% identity to the sequence according to SEQ ID NO.: 18. In another particularly preferred embodiment the ligand according to (c) is a polypeptide comprising or consisting of an amino acid sequence which exhibits 95%, at least 98% or 100% identity to the sequence according to SEQ ID NO.: 19. In yet another particularly preferred embodiment the ligand according to (c) is a polypeptide comprising or consisting of an amino acid sequence which exhibits 95%, at least 98% or 100% identity to the sequence according to SEQ ID NO.: 20. In still another particularly preferred the ligand according to (c) is a polypeptide comprising or consisting of an amino acid sequence which exhibits 95%, at least 98% or 100% identity to the sequence according to SEQ ID NO.: 21.

In a further particularly preferred embodiment the ligand according to (c) is a polypeptide comprising or consisting of an amino acid sequence which exhibits at least 95% identity to the sequence according to SEQ ID NO.: 18, SEQ ID NO.: 19, SEQ ID NO.: 20 or SEQ ID NO.: 21.

In yet another particularly preferred embodiment the ligand according to (c) is a polypeptide comprising or consisting of an amino acid sequence which exhibits at least 95% identity to the sequence according to SEQ ID NO.: 18. In a most preferred embodiment the ligand according to (c) is a polypeptide comprising or consisting of an amino acid sequence according to SEQ ID NO.: 18.

The aforementioned method according to the invention may be used for quantifying the total amount of soluble CCR6 receptor polypeptide in a liquid sample from a subject or the amount of soluble CCR6 receptor polypeptide bound to CCL18, CCL20 and/or beta defensin in a liquid sample from a subject.

If the total amount of soluble CCR6 receptor polypeptide in the liquid sample is to be quantified, it is preferred that ligand is added in step (c) in order to saturate CCR6 receptor polypeptide present in the sample with ligand. If the amount of soluble CCR6 receptor polypeptide bound to CCL18, CCL20 and/or beta defensin in the liquid sample from the subject is to be quantified, it is preferred that no ligand is added in step (c). The detecting agent in (d) will then only detect ligand-bound soluble CCR6 receptor polypeptides in the liquid sample.

The choice of a suitable method for quantifying the signal from the detecting agent in step (e) will depend on the nature of the label of the detecting agent. Suitable methods for quantifying a signal from a labelled detecting agent are well known in the art.

For example, if the label is an enzyme (such as e.g. alkaline phosphatase), a colorless substrate (such as e.g. p-Nitrophenyl Phosphate) which is converted by the enzyme into a colored product, may be added. Following the addition of said substrate, the amount of colored product generated by the enzyme may e.g. be measured spectrophotometrically.

In another example, if the label is a fluorescent dye, the fluorescent signal may e.g. be quantified by using a laser scanner.

In a further aspect, the present invention also relates to a method for detecting and/or prognosticating an interstitial lung disease or cancer in a subject, wherein the method comprises the step of determining the level of a soluble CCR6 receptor polypeptide in a sample from said subject.

Said method is preferably performed in vitro.

A "soluble CCR6 receptor polypeptide" in the context of the aforementioned method according to the invention is preferably a naturally occurring soluble CCR6 receptor polypeptide.

In one preferred embodiment, the soluble CCR6 receptor polypeptide comprises or consists of an amino acid sequence selected from the group consisting of:
(a) an amino acid sequence which exhibits at least 80% identity to the sequence according to SEQ ID NO.: 1; and
(b) a fragment of the amino acid sequence according to (a);
wherein said isolated soluble CCR6 receptor polypeptide is capable of binding to CCL18 and/or CCL20.

In one preferred embodiment the amino acid sequence according to (a) exhibits at least 85%, more preferably at least 90%, more preferably at least 95% or even more preferably at least 98% identity to the sequence according to SEQ ID NO.: 1. In a particularly preferred embodiment the amino acid sequence according to (a) exhibits at least 95% identity to the sequence according to SEQ ID NO.: 1. In a most preferred embodiment the amino acid sequence according to (a) exhibits 100% identity to the sequence according to SEQ ID NO.:1.

In another particularly preferred embodiment, the soluble CCR6 receptor polypeptide comprises or consists of an amino acid sequence according to SEQ ID NO.: 1.

In a further preferred embodiment the soluble CCR6 receptor polypeptide is ligand-free soluble CCR6 receptor polypeptide. In this context the term "ligand-free" means that the soluble CCR6 receptor polypeptide is not bound to ligand, such as e.g. CCL 18 or CCL20.

In one embodiment, determining the level of soluble CCR6 receptor polypeptide may be achieved by contacting the sample from the subject with a detecting agent specific for CCR6, preferably with a detecting agent specific for soluble CCR6 receptor polypeptide. A detecting agent is specific for CCR6 or soluble CCR6 receptor polypeptide, if it binds CCR6 or soluble CCR6 receptor polypeptide with a higher affinity than any other compound in a sample (i.e. a non-target). Preferably, a detecting agent is specific for CCR6 or soluble CCR6 receptor polypeptide if it binds to CCR6 or soluble CCR6 receptor polypeptide only and does not bind at all to a non-target. In a preferred embodiment a detecting agent specific for soluble CCR6 receptor polypeptide binds to the extracellular domain of CCR6. In a particularly preferred embodiment a detecting agent specific for soluble CCR6 receptor polypeptide binds to the sequence according to SEQ ID NO.: 1.

A preferred detecting agent for detecting soluble CCR6 receptor polypeptide is an antibody or an aptamer. Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments. In one preferred embodiment commercially available antibodies specific for CCR6 or soluble CCR6 receptor polypeptide may be used.

Antibodies described herein may be produced according to any suitable method known to the person skilled in the art. Polyclonal antibodies may e.g. be produced by immunization of animals with the antigen of choice, whereas monoclonal antibodies of defined specificity may e.g. be produced using the hybridoma technology developed by Köhler and Milstein (Köhler and Milstein, 1976, Eur. J. Immunol., 6:511-519).

In a preferred embodiment, a detecting agent as described herein above may comprise a detectable label. Any suitable label, which can be attached to the detecting agent, may be used. In one preferred embodiment the detectable label is covalently or non-covalently attached to the detecting agent. Examples of labels that may be attached to the detecting agent include e.g. fluorescent dyes such as e.g. Cyanine dyes, e.g. Cyanine 3, Cyanine 5 or Cyanine 7, Alexa Fluor dyes, e.g. Alexa 594, Alexa 488 or Alexa 532, fluorescein family dyes, R-Phycoerythrin, Texas Red, rhodamine and Fluoresceinisothiocyanat (FITC). Detecting agents may also be labeled with enzymes such as e.g. horseradish peroxidase, alkaline phosphatase or beta-lactamase, radioisotopes such as e.g. $^{3}H$, $^{14}C$, $^{32}P$, $^{33}P$, $^{35}S$ or $^{125}I$, metal such as e.g. gold or with biotin. In another preferred embodiment the detecting agent may also be detected by a secondary detecting agent comprising a label as described above.

Preferably a secondary detecting agent is capable of specifically binding to the above described detecting agent. In a particularly preferred embodiment a secondary detecting agent is an antibody.

Determining the level of soluble CCR6 receptor polypeptide in a sample from a subject may be accomplished by any method known in the art. In some embodiments the level of soluble CCR 6 receptor polypeptide in a sample from a subject may e.g. be detected using an immunoassay such as, for example, ELISA, Western Blot, immunoprecipitation or radioimmunoassay. The level of soluble CCR 6 receptor polypeptide in a sample from a subject may also be detected by using the above described method for quantifying the amount of a soluble CCR6 receptor polypeptide in a liquid sample from a subject.

The terms "detecting an interstitial lung disease" or "detecting cancer" as used herein means that the presence of an interstitial lung disease or a cancerous disease or disorder may be identified in a subject or in a sample from a subject. Preferably, said subject is previously not known to suffer from an interstitial lung disease or cancer respectively. In one preferred embodiment the subject is suspected to suffer from an interstitial lung disease or cancer.

In order to detect an interstitial lung disease or cancer in a subject, determining the level of soluble CCR6 receptor polypeptide in the sample from the subject may in some embodiments be performed alongside measuring or determining the amount of other compounds or factors indicative of an interstitial lung disease or cancer respectively. For example, known markers for interstitial lung disease, such as e.g. serum markers surfactant protein (SP) A and D, or known cancer markers may be detected in the same sample or in a different sample from the subject. Further suitable markers are known to the skilled person.

In a preferred embodiment the above-described method further comprises the step of comparing the level of soluble CCR6 receptor polypeptide determined in the sample from the subject to the level of soluble CCR6 receptor polypeptide in a control, wherein a lower level of soluble CCR6 receptor polypeptide determined in the sample from the subject in comparison to the control indicates the presence of an interstitial lung disease or a cancer in the subject.

In another preferred embodiment the above-described method further comprises the step of comparing the level of ligand-free soluble CCR6 receptor polypeptide determined in the sample from the subject to the level of ligand-free soluble CCR6 receptor polypeptide in a control, wherein a lower level of ligand-free soluble CCR6 receptor polypeptide determined in the sample from the subject in comparison to the control indicates the presence of an interstitial lung disease or a cancer in the subject. In this context the term "ligand-free" means that the soluble CCR6 receptor polypeptide is not bound to ligand, such as e.g. CCL 18 or CCL20.

In order to determine the amount of total soluble CCR6 receptor polypeptide or the amount of ligand-bound/ligand-free soluble CCR6 receptor polypeptide in a sample from a subject, the skilled person may e.g. use the above described method for quantifying the amount of a soluble CCR6 receptor polypeptide in a liquid sample from a subject.

In one preferred embodiment the control is a sample from a healthy subject. In a preferred embodiment a lower level of soluble CCR6 receptor polypeptide determined in the sample from the subject in comparison to the control indicates the presence of an interstitial lung disease or a cancer in the subject. Preferably, the level of soluble CCR6 receptor polypeptide determined in the sample from the subject is at least 2 fold, preferably at least 3 fold, at least 4 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or at least 10000 fold lower than in the control. Most preferably, the level of soluble CCR6 receptor determined in the sample from the subject is at least 2 fold, at least 3 fold, at least 10 fold, at least 50 fold, at least 100 fold or at least 1000 fold lower than in the control. In one preferred embodiment the soluble CCR6 receptor polypeptide is ligand-free soluble receptor polypeptide.

In another preferred embodiment the control may also be a sample derived from a subject known to suffer from an interstitial lung disease or cancer (control subject), i.e. a subject that has been independently diagnosed with an interstitial lung disease or cancer, wherein the cancer is preferably an adenocarcinoma, most preferably an adenocarcinoma of the lung. In such cases a lower level of soluble CCR6 receptor polypeptide determined in the sample from the subject in comparison to the control indicates a further progression of the interstitial lung disease or the cancer in the subject from which the sample was derived in comparison to the control subject. In one preferred embodiment the soluble CCR6 receptor polypeptide is ligand-free soluble CCR6 receptor polypeptide.

In the context of the present invention, the control is preferably separated from the body of the subject it is derived from.

The term "prognosticating an interstitial lung disease or cancer" as used herein refers to the prediction of the course or outcome of a diagnosed or detected interstitial lung disease or cancer, e.g. during a certain period of time, e.g. during treatment or after treatment. The term may also refer to a determination of chance of survival or recovery from the interstitial lung disease or cancer, as well as to a prediction of the expected survival time of a subject.

For example, the level of soluble CCR6 receptor polypeptide may be determined in a sample from a subject at a given point of time and compared to the respective level of soluble CCR6 receptor polypeptide determined in a sample from the same subject at a later point of time, wherein an increase or decrease in the level of soluble CCR6 receptor polypeptide indicates an improvement or aggravation of the disease condition. Such an approach may e.g. be used during medical treatment of a patient suffering from an interstitial lung disease or cancer.

Thus in one preferred embodiment the aforementioned method according to the invention may also be used to monitor the efficacy of treatment of an interstitial lung disease or cancer in vitro. The efficacy of treatment of an interstitial lung disease or cancer may e.g. be monitored by detecting the level of soluble CCR6 polypeptide in different samples from a subject that were provided over a given period of time while the subject from which the samples were derived was subjected to treatment of an interstitial lung disease or cancer. An increase or decrease in the level of soluble CCR6 polypeptide in samples provided from the subject over a given period of time may then indicate the efficacy of treatment. In one preferred embodiment the soluble CCR6 receptor polypeptide is ligand-free soluble CCR6 receptor polypeptide.

In one preferred embodiment the level of soluble CCR6 receptor polypeptide in the control may be determined in parallel to the level of soluble CCR6 receptor polypeptide in the sample from the subject.

In another preferred embodiment the control may be a predetermined value. Such a value may e.g. be based on the results of previous experiments determining the level of soluble CCR6 receptor polypeptide in one or more samples from a healthy subject or a subject known to suffer from an interstitial lung disease or cancer. In some embodiments a predetermined value may be derivable from a database.

In one preferred embodiment the level of soluble CCR6 receptor polypeptide may be compared to more than one control, e.g. to 2, 3, 4, 5, 6, 7, 8, 9, 10, 20, 30, 40, 50, 60, 70, 80, 90, 100 or more than 100 controls.

Preferably, the sample from the subject used in the methods according to the invention is separated from the body of the subject. The sample is preferably a liquid sample. In a preferred embodiment, the liquid sample is selected from the group consisting of blood, serum, plasma, bronchoalveolar lavage fluid, pleural effusion, sputum, saliva or urine. In a particularly preferred embodiment the sample is serum. Preferably, the sample is cell- and membrane-free. In order to remove cells and cellular membranes from the sample, the skilled person may e.g. centrifuge the sample prior to determining the level of soluble CCR6 receptor polypeptide.

In a further aspect the present invention also relates to a diagnostic kit for detecting an interstitial lung disease or cancer comprising a detecting agent specific for CCR6 or soluble CCR6 receptor polypeptide.

In a preferred embodiment a detecting agent specific for soluble CCR6 receptor polypeptide specifically binds to the extracellular domain of CCR6. In a particularly preferred embodiment a detecting agent specific for soluble CCR6 receptor polypeptide specifically binds to the sequence according to SEQ ID NO.: 1.

In a preferred embodiment, said detecting agent is an antibody or an aptamer.

Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')$_2$ fragments. In one preferred embodiment commercially available antibodies specific for CCR6 or soluble CCR6 receptor polypeptide may be used.

An "aptamer" specific for CCR6 or soluble CCR6 receptor polypeptide may e.g. be a DNA, RNA or peptide aptamer.

A polynucleotide aptamer is preferably between about 10 to about 300 nucleotides in length. Preferably an aptamer is between about 30 to about 100 nucleotides in length. Most preferably an aptamer is between about 10 to 60 nucleotides in length.

Aptamers may be prepared by any known method, including synthetic, recombinant, and purification methods, and may be used alone or in combination with other aptamers specific for CCR6 or soluble CCR6 receptor polypeptide.

In one preferred embodiment the soluble CCR6 receptor polypeptide in the context of the above-described method of the invention is a ligand-free soluble CCR6 receptor polypeptide.

In a preferred embodiment of the above-described method the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans cell histiocytosis/histiocytosis X (HX) or eosinophilic pneumonia).

In another preferred embodiment of the above-described method the interstitial lung disease is an idiopathic interstitial pneumonia.

In a particularly preferred embodiment of the above-described method the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamative interstitial pneumonia, acute interstitial pneumonia and lymphocytic interstitial pneumonia. Most preferably, the interstitial lung disease is idiopathic pulmonary fibrosis.

In a further preferred embodiment of the above-described method the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a particularly preferred embodiment of the above-described method the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma. Most preferably, the cancer is adenocarcinoma, preferably adenocarcinoma of the lung.

The present invention in a further aspect also relates to a pharmaceutical composition comprising a compound capable of inhibiting the activity and/or the expression of CCL18 or CCL20.

A pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures.

In a preferred embodiment a pharmaceutical composition according to the invention is administered parenterally, e.g. in form of solutions for injection or infusion, orally, e.g. in the form of a tablet, pill, lozenge or capsule or via inhalation.

For the production of pills, tablets, sugar-coated tablets and hard gelatin capsules for example, lactose, starch, for example maize starch, or starch derivatives, talc, stearic acid or its salts, etc may be used. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc.

In some embodiments the pharmaceutical compositions also contains additives, such as for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Examples of suitable excipients for the various different forms of pharmaceutical compositions described herein may e.g. be found in the "Handbook of Pharmaceutical Excipients", 2nd Edition, (1994), Edited by A Wade and P J Weller.

In a preferred embodiment the compound capable of inhibiting the activity and/or the expression of CCL18 or CCL20 is selected from the group consisting of the isolated soluble CCR6 receptor polypeptide according to the invention, a small molecule capable of binding to CCL18 or CCL20, an aptamer specific for CCL18 or CCL20, an antibody specific for CCL18 or CCL20, an antisense molecule suitable for reducing or inhibiting the expression of CCL18 or CCL20 and an siRNA molecule suitable for reducing or inhibiting the expression of CCL18 or CCL20.

The term "small molecule" as used herein refers to small organic compounds having low molecular weight.

A small molecule may be a synthetic compound not known to occur in nature or a naturally-occurring compound isolated from or known to occur in natural sources, such as e.g. cells, plants, fungi, animals and the like. A small molecule in the context of the present invention preferably has a molecular weight of less than 5000 Dalton, more preferably of less than 4000 Dalton, more preferably less than 3000 Dalton, more preferably less than 2000 Dalton or even more preferably less than 1000 Dalton. In a particularly preferred embodiment a small molecule in the context of the present invention has a molecular weight of less than 800 Dalton.

In another preferred embodiment a small molecule in the context of the present invention has a molecular weight of 50 to 3000 Dalton, preferably of 100 to 2000 Dalton, more preferably of 100 to 1500 Dalton and even more preferably of 100 to 1000 Dalton. Most preferably a small molecule in the context of the present invention has a molecular weight of 100 to 800 Dalton.

Small molecules capable of binding to CCL18 or to CCL20 may e.g. be identified by screening small compound libraries.

An "aptamer" may be a DNA, RNA or peptide aptamer specific for CCL18 or for CCL20.

A polynucleotide aptamer is preferably between about 10 to about 300 nucleotides in length. Preferably an aptamer is between about 30 to about 100 nucleotides in length. Most preferably an aptamer is between about 10 to 60 nucleotides in length.

Aptamers may be prepared by any known method, including synthetic, recombinant, and purification methods, and may be used alone or in combination with other aptamers specific for CCL18 or for CCL20.

An antibody specific for CCL18 or for CCL20 may be a monoclonal or polyclonal antibody. In some embodiments the antibody may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments, provided that said antibody variants or fragments are specific for CCL18 or for CCL20.

The term "antisense molecule suitable for reducing or inhibiting the expression of CCL18 or CCL20" refers to a polynucleotide which is complementary to CCL18 mRNA or CCL20 mRNA respectively. It is preferred that said antisense molecule is suitable for use in an antisense approach to inhibit translation of CCL18 mRNA or CCL20 mRNA in a cell. Said antisense molecule may be a DNA or RNA molecule and may be single stranded or double stranded. In a preferred embodiment, the antisense molecule is single stranded DNA molecule or a double or single stranded RNA molecule.

An antisense molecule preferably has a length of about 10 to about 500 nucleotides, of about 11 to about 200 nucleotides, of about 12 to about 100 nucleotides, about 13 to about 75 nucleotides or of about 14 to about 50 nucleotides, of about 15 to about 40 nucleotides, of about 16 to about 30 nucleotides or of about 17 to about 25 nucleotides.

An siRNA molecule suitable for reducing or inhibiting the expression of CCL18 or CCL20 may be a single stranded or double stranded siRNA molecule that is capable of hybridizing to CCL18 mRNA or CCL20 mRNA, thereby inducing RNA interference or any other intracellular antisense mechanism that results in reduction or inhibition of the expression of CCL18 protein or CCL20 protein.

Said siRNA molecule may be of any sequence that allows the siRNA molecule to induce RNA interference resulting in reduction or inhibition of the expression of CCL18 protein or CCL20 protein.

Preferably, the siRNA molecule has a length of between 10 and 100, between 12 and 80, between 14 and 60, between 16 and 50, between 17 and 40, more preferably between 18 and 30 nucleotides and most preferably between 18 and 26 nucleotides.

A compound capable of or suitable for reducing or inhibiting the expression of CCL18 or CCL20 may reduce or inhibiting the expression of CCL18 or CCL20 by at least 10%, at least 20%, at least 30%, at least 40%, at least 50%, at least 60%, at least 70%, more preferably at least 80%, at least 90%, at least 91%, at least 92%, at least 93%, at least 94%, at least 95%, at least 96%, at least 97%, at least 98% or at least 99% when compared to a control. In some preferred embodiments a compound capable of or suitable for reducing or inhibiting the expression of CCL18 or CCL20 may reduce or inhibiting the expression of CCL18 or CCL20 by 100%.

In another preferred embodiment, a pharmaceutical composition according to the invention comprises a further active compound suitable for the treatment or prevention of an interstitial lung disease and/or cancer.

Examples of further active compound suitable for the treatment of an interstitial lung disease are e.g. anti-inflammatory drugs such as e.g. prednisone or other corticosteroids, azathioprine, methotrexate, mycophenolate or cyclophosphamide, antioxidants, such as e.g. acetylcysteine antifibrotic agents, such as e.g. bosentan or pirfenidone, minocycline, sildenafil, thalidomide, anti-TNF antibodies, such as e.g. Infliximab; etanercept, interferon gamma, anti-IL-13 antibodies, endothelin inhibitors, Zileuton, anticoagulants, macrolides, phosphodiesterase (PDE) 4 inhibitors, such as e.g. roflumilast, Aviptadil, alpha-melanocyte-stimulating hormone (alpha-MSH), tyrosine kinase inhibitors, such as e.g. imatinib, dasatinib and nilotinib.

The further active compound suitable for the treatment of cancer is preferably a chemotherapeutic agent. Chemotherapeutic agents suitable for the treatment of cancer are well known to the skilled person. Examples of chemotherapeutic agents are e.g. temozolomide, adriamycin, doxorubicin, epirubicin, 5-fluorouracil, cytosine arabinoside ("Ara-C"), cyclophosphamide, thiotepa, busulfan, cytoxin, taxoids, e.g., paclitaxel, toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, melphalan and other related nitrogen mustards and hormonal agents that act to regulate or inhibit hormone action on tumors such as tamoxifen and onapristone.

The pharmaceutical composition according to the invention may comprise one or more than one further active compound suitable for the treatment or prevention of an interstitial lung disease and/or one or more than one further active compound suitable for the treatment or prevention of cancer. In a preferred embodiment the pharmaceutical composition according to the invention comprises 1, 2, 3, 4, 5, 6, 7, 8, 9, 10 or more than 10 further active compounds suitable for the treatment of prevention of an interstitial lung disease and/or 1, 2, 3, 4, 5, 6, 7, 8, 9, 10 or more than 10 further active compound suitable for the treatment of cancer.

In other preferred embodiments one or more separate compositions comprising an active compound suitable for the treatment or prevention of an interstitial lung disease and/or an active compound suitable for the treatment or prevention of cancer may be administered to a subject, preferably a human subject, in combination with a pharmaceutical composition according to the invention comprising a compound capable of inhibiting the activity and/or the expression of CCL18 or CCL20.

In a preferred embodiment, the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In another preferred embodiment the interstitial lung disease is an idiopathic interstitial pneumonia.

In a particularly preferred embodiment the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia. Most preferably, the interstitial lung disease is idiopathic pulmonary fibrosis.

In another preferred embodiment the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a particularly preferred embodiment the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma. Most preferably, the cancer is adenocarcinoma, preferably adenocarcinoma of the lung.

The inventors of the present invention surprisingly found that the isolated soluble CCR6 receptor polypeptide according to the invention is suitable for therapeutic use.

Therefore, in a further aspect the present invention relates to the isolated soluble CCR6 receptor polypeptide according to the invention for use in therapy.

Several diseases have been found to be characterised by elevated serum levels of CCL18 or CCL20, meaning that levels of CCL18 or CCL20 in serum from a patient suffering from the disease are elevated in comparison to the levels of CCL18 or CCL20 in serum from healthy controls.

Thus, the present invention also relates to the isolated soluble CCR6 receptor polypeptide according to the invention or a pharmaceutical composition according to the invention for use in the treatment of prevention of a disease characterised by an elevated serum level of CCL 18 and/or CCL20. The term "an elevated serum level of CCL 18 and/or CCL20" means that the level of CCL18 and/or CCL20 in serum from a patient suffering from the disease is elevated in comparison to the level of CCL18 and/or CCL20 in serum from a healthy control.

In another aspect the present invention also relates to the isolated soluble CCR6 receptor polypeptide according to the invention or a pharmaceutical composition according to the invention for use in the treatment or prevention of a disease selected from the group consisting of an interstitial lung disease, cancer, Gaucher disease, thalassemia, preferably β-thalassemia, rheumatoid arthritis, retroperitoneal fibrosis (Ormond's disease) and/or chronic inflammatory skin disease, preferably atopic dermatitis or bullous pemphigoid.

In a preferred embodiment the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In another preferred embodiment the interstitial lung disease is an idiopathic interstitial pneumonia.

In a particularly preferred embodiment the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia. Most preferably, the interstitial lung disease is idiopathic pulmonary fibrosis.

In a further preferred embodiment the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a particularly preferred embodiment the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma. Most preferably, the cancer is adenocarcinoma, preferably adenocarcinoma of the lung.

In yet another aspect the present invention relates to the isolated soluble CCR6 receptor polypeptide according to the invention or a pharmaceutical composition according to the invention for use in the treatment or prevention of an interstitial lung disease and/or cancer.

As used herein, the term "prevention" and its grammatical equivalents refer to any reduction of a subject's predisposition or risk for developing an interstitial lung disease and/or cancer.

In another aspect the present invention relates to the use of the isolated soluble CCR6 receptor polypeptide according to the invention or a pharmaceutical composition according to the invention for the manufacture of a medicament for the treatment or prevention of an interstitial lung disease and/or cancer.

In another aspect the present invention also relates to a detecting agent specific for the isolated soluble CCR6 receptor polypeptide according to the invention.

In a preferred embodiment the detecting agent is an antibody or an aptamer.

An "aptamer" may be a DNA, RNA or peptide aptamer. A polynucleotide aptamer is preferably between about 10 to about 300 nucleotides in length. Preferably an aptamer is between about 30 to about 100 nucleotides in length. Most preferably an aptamer is between about 10 to 60 nucleotides in length. Aptamers may be prepared by any method known in the art, including e.g. synthetic, recombinant, and purification methods.

Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments. The detecting agent preferably comprises a detectable label. Suitable labels have been described herein above.

A detecting agent is specific for the isolated soluble CCR6 receptor polypeptide according to the invention, if it binds the isolated soluble CCR6 receptor polypeptide according to the invention with a higher affinity than any other compound in a sample (i.e. a non-target). Preferably, a detecting agent is specific for the isolated soluble CCR6 receptor polypeptide according to the invention if it binds the isolated soluble CCR6 receptor polypeptide according to the invention only and does not bind at all to a non-target.

In a preferred embodiment the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In another preferred embodiment the interstitial lung disease is an idiopathic interstitial pneumonia.

In a particularly preferred embodiment the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia. Most preferably, the interstitial lung disease is idiopathic pulmonary fibrosis.

In a further preferred embodiment the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a particularly preferred embodiment the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma. Most preferably, the cancer is adenocarcinoma, preferably adenocarcinoma of the lung.

In a further aspect the present invention also relates to a detecting agent specific for CCR6 receptor or for the isolated soluble CCR6 receptor polypeptide according to the invention for use in detecting an interstitial lung disease or cancer in a sample from a subject.

In a preferred embodiment the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In another preferred embodiment the interstitial lung disease is an idiopathic interstitial pneumonia.

In a particularly preferred embodiment the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia. Most preferably, the interstitial lung disease is idiopathic pulmonary fibrosis.

In a further preferred embodiment the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a particularly preferred embodiment the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma. Most preferably, the cancer is adenocarcinoma, preferably adenocarcinoma of the lung.

In another preferred embodiment the detecting agent is an antibody or an aptamer.

An "aptamer" may be a DNA, RNA or peptide aptamer. A polynucleotide aptamer is preferably between about 10 to about 300 nucleotides in length. Preferably an aptamer is between about 30 to about 100 nucleotides in length. Most preferably an aptamer is between about 10 to 60 nucleotides in length. Aptamers may be prepared by any method known in the art, including e.g. synthetic, recombinant, and purification methods.

Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments. The detecting agent preferably comprises a detectable label. Suitable labels have been described herein above.

A detecting agent is specific for CCR6 receptor or for the isolated soluble CCR6 receptor polypeptide according to the invention, if it binds CCR6 receptor or the isolated soluble CCR6 receptor polypeptide according to the invention with a higher affinity than any other compound in a sample (i.e. a non-target). Preferably, a detecting agent is specific for CCR6 receptor or the isolated soluble CCR6 receptor polypeptide according to the invention if it binds CCR6 receptor or the isolated soluble CCR6 receptor polypeptide according to the invention only and does not bind at all to a non-target.

In this context, the sample from a subject may be a liquid sample or a solid sample. In one preferred embodiment, the sample from a subject is selected from the group consisting of serum, plasma, bronchoalveolar lavage fluid, pleural effusion, sputum, saliva and urine. In a particularly preferred embodiment the liquid sample from a subject is serum. In another preferred embodiment the sample from the subject is a tissue sample, preferably a lung tissue sample. Tissue samples may e.g. be fresh or frozen tissue samples or fixed paraffin embedded samples. In one preferred embodiment the sample may be a biopsy or resection sample. In a further preferred embodiment the sample is a bronchial brushing sample.

In a preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In a particularly preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the interstitial lung disease is an idiopathic interstitial pneumonia.

In a further preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamative interstitial pneumonia, acute interstitial pneumonia and lymphocytic interstitial pneumonia.

In a particularly preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the interstitial lung disease is idiopathic pulmonary fibrosis. For an overview on the classification of interstitial lung diseases the skilled person may e.g. refer to American Thoracic Society/European Respiratory Society International Multidisciplinary Consensus Classification of the Idiopathic Interstitial Pneumonias, American Thoracic Society; European Respiratory Society, Am J Respir Crit Care Med. 2002 Jan. 15; 165(2):277-304. In some embodiments interstitial lung disease may be caused by a condition selected from the group consisting of scleroderma lung disease, sarcoidosis, hypersensitivity pneumonitis, rheumatoid arthritis, lupus erythematosus and asbestosis.

In another preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer.

In a further preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma.

In a particularly preferred embodiment of the method according to the invention, the isolated soluble CCR6 receptor polypeptide according to the invention, the diagnostic kit according to the invention, the pharmaceutical composition according to the invention, the use according to the invention and/or the detecting agent according to the invention the cancer is lung cancer, most preferably adenocarcinoma of the lung, or pleural mesothelioma. In a most preferred embodiment the cancer is adenocarcinoma of the lung.

The inventors of the present invention further surprisingly found that inhibitors of CCR6 receptor activity can be used for the therapy of an interstitial lung disease or cancer.

Therefore in a further aspect the present invention relates to an isolated polypeptide comprising or consisting of an amino acid sequence selected from the group consisting of:
(a) an amino acid sequence which exhibits at least 80%, preferably at least 85%, more preferably at least 90%, even more preferably at least 95% and most preferably 100% identity to the sequence according to SEQ ID NO.: 9, 22 or 23; and
(b) a fragment of the amino acid sequence according to (a);
wherein said isolated polypeptide is capable of binding to and inhibiting the activity of the CCR6 receptor.

Preferably said CCR6 receptor is human CCR6 receptor. In one preferred embodiment said CCR6 receptor is a polypeptide encoded by the sequence according to SEQ ID NO.: 3 or SEQ ID NO.: 4. In another preferred embodiment said CCR6 receptor is a polypeptide according to SEQ ID NO.: 27.

In a preferred embodiment the amino acid sequence according to (a) exhibits at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.: 9, SEQ ID NO.:22 or SEQ ID NO.:23. In a most preferred embodiment the amino acid sequence according to (a) exhibits 100% identity to the sequence according to SEQ ID NO.:9, SEQ ID NO.:22 or SEQ ID NO.:23.

In another preferred embodiment, the amino acid sequence according to (a) exhibits at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.: 9. In a further preferred embodiment the amino acid sequence according to (a) is an amino acid sequence according to SEQ ID NO.: 9.

In a further preferred embodiment, the amino acid sequence according to (a) exhibits at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:22. In a further preferred embodiment the amino acid sequence according to (a) is an amino acid sequence according to SEQ ID NO.: 22.

In another preferred embodiment the amino acid sequence according to (a) exhibits at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.: 23. In a further preferred embodiment the amino acid sequence according to (a) is an amino acid sequence according to SEQ ID NO.: 23.

In some preferred embodiments the amino acid sequence according to (a) may exhibit at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% or even more preferably at least 99% identity to the sequence according to SEQ ID NO.:9 and SEQ ID NO.:22.

In another preferred embodiment in the amino acid sequence according to (a) not more than 1, 2, 3, 4, 5, 6, 7, 8, 9 or 10 amino acids of the sequence according to SEQ ID NO:9, SEQ ID NO.:22 or SEQ ID NO.:23 are changed (i.e. deleted, inserted, modified and/or substituted by other amino acids).

In a further preferred embodiment in the amino acid sequence according to (a) not more than 1, 2, 3, 4, 5, 6, 7, 8, 9 or 10 amino acids of the sequence according to SEQ ID NO:9 are changed (i.e. deleted, inserted, modified and/or substituted by other amino acids). In another preferred embodiment in the amino acid sequence according to (a) not more than 1, 2, 3, 4, 5, 6, 7, 8, 9 or 10 amino acids of the sequence according to SEQ ID NO:22 are changed (i.e. deleted, inserted, modified and/or substituted by other amino acids). In yet another preferred embodiment in the amino acid sequence according to (a) not more than 1, 2, 3, 4, 5, 6, 7, 8, 9 or 10 amino acids of the sequence according to SEQ ID NO:23 are changed (i.e. deleted, inserted, modified and/or substituted).

Amino acids of the aforementioned isolated polypeptide according to the invention may also be modified, e.g. chemically modified. For example, the side chain or a free amino or carboxy-terminus of an amino acid of the protein may be modified by e.g. glycosylation, amidation, phosphorylation, ubiquitination, etc.

In a preferred embodiment the amino acid sequence according to (a) comprises at least 8 consecutive amino acids of the sequence according to SEQ ID NO.:9, 22 or 23. Thus, in one preferred embodiment the amino acid sequence according to (a) exhibits at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, even more preferably at least 99% or most preferably 100% identity to the sequence according to SEQ ID NO.:9, 22 or 23 and comprises at least 8 consecutive amino acids of the sequence according to SEQ ID NO.:9, 22, or 23. In another preferred embodiment the amino acid sequence according to (a) exhibits at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, even more preferably at least 99% or most preferably 100% identity to the sequence according to SEQ ID NO.:9 and comprises at least 8 or at least 15 consecutive amino acids of the sequence according to SEQ ID NO.:9. In a further preferred embodiment the amino acid sequence according to (a) exhibits at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, even more preferably at least 99% or most preferably 100% identity to the sequence according to SEQ ID NO.: 22 and comprises at least 8 or at least 15 consecutive amino acids of the sequence according to SEQ ID NO.: 22. In another preferred embodiment the amino acid sequence according to (a) exhibits at least 80%, preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, even more preferably at least 99% or most preferably 100% identity to the sequence according to SEQ ID NO.:23 and comprises at least 8 or at least 15 consecutive amino acids of the sequence according to SEQ ID NO.:23. In another preferred embodiment the amino acid sequence according to (a) exhibits at least 95%, 98% or 100% identity to the sequence according to SEQ ID NO.:9, 22 or 23 and comprises at least 9, at least 10, at least 11, at least 12, at least 13, at least 14, at least 15, at least 16, at least 17, at least 18, at least 19 or at least 20 consecutive amino acids of the sequence according to SEQ ID NO.:9, 22 or 23. In a more preferred embodiment, the amino acid sequence according to (a) exhibits at least 95%, 98% or 100% identity to the sequence according to SEQ ID NO.:9, 22, or 23 and comprises at least 8 or at least 15 consecutive amino acids of the sequence according to SEQ ID NO.:9, SEQ ID NO.:22 or SEQ ID NO.:23.

In a further preferred embodiment the amino acid sequence according to (a) exhibits at least 95%, 98% or 100% identity to the sequence according to SEQ ID NO.:9 and comprises at least 9, at least 10, at least 11, at least 12, at least 13, at least 14, at least 15, at least 16, at least 17, at least 18, at least 19 or at least 20 consecutive amino acids of the sequence according to SEQ ID NO.:9.

In another preferred embodiment the amino acid sequence according to (a) exhibits at least 95%, 98% or 100% identity to the sequence according to SEQ ID NO.:22 and comprises at least 9, at least 10, at least 11, at least 12, at least 13, at least 14, at least 15, at least 16, at least 17, at least 18, at least 19 or at least 20 consecutive amino acids of the sequence according to SEQ ID NO.:22.

In a further preferred embodiment the amino acid sequence according to (a) exhibits at least 95%, 98% or 100% identity to the sequence according to SEQ ID NO.:23 and comprises at least 9, at least 10, at least 11, at least 12, at least 13, at least 14, at least 15, at least 16, at least 17, at least 18, at least 19 or at least 20 consecutive amino acids of the sequence according to SEQ ID NO.:23.

In a preferred embodiment, the isolated polypeptide according to the invention has a length of less than 3000 amino acids, preferably less than 2000 amino acids, more preferably less than 1000 amino acids, more preferably less than 500 amino acids, more preferably less 300 amino acids, more preferably less than 200 amino acids, more preferably less than 100 amino acids or most preferably less than 50 amino acids.

In a further preferred embodiment the isolated polypeptide according to the invention has a length of between at least 8 and at least 3000 amino acids, preferably between at least 8 and at least 2000 amino acids, more preferably between at least 8 and at least 1000 amino acids, more preferably between at least 8 and 500 amino acids, more preferably between at least 8 and 300 amino acids, more preferably between at least 8 and 200 amino acids, and even more preferably between at least 8 and 100 amino acids or between at least 8 and 50 amino acids.

Most preferably, the isolated polypeptide according to the invention has a length of at least 8, at least 29 or at least 31 amino acids.

In another preferred embodiment the isolated polypeptide according to (a) has a length of between at least 29 and 3000 amino acids, preferably between at least 29 and 2000 amino acids, more preferably between at least 29 and 1000 amino acids, between at least 29 and 500 amino acids, between at least 29 and 300 amino acids, between at least 29 and 200 amino acids, between at least 29 and 100 amino acids or between at least 29 and 50 amino acids.

In a further preferred embodiment the isolated polypeptide according to (a) has a length of between at least 31 and 3000 amino acids, preferably between at least 31 and 2000 amino acids, more preferably between at least 31 and 1000 amino acids, between at least 31 and 500 amino acids, between at least 31 and 300 amino acids, between at least 31 and 200 amino acids, between at least 31 and 100 amino acids or between at least 31 and 50 amino acids.

A fragment is typically a portion of the amino acid sequence it refers to.

In a preferred embodiment the fragment according to (b) is at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 or at least 28 amino acids in length. In a preferred embodiment the fragment according to (b) has a length of at least 10, at least 15 or at least or at least 20 amino acids. In a most preferred embodiment the fragment according to (b) has a length of 15 amino acids.

In another particularly preferred embodiment the isolated polypeptide according to the invention comprises or consists of an amino acid sequence according to SEQ ID NO.: 9, SEQ ID NO.:22 or SEQ ID NO.:23, wherein said polypeptide is capable of binding to and inhibiting the activity of the CCR6 receptor. Most preferably the aforementioned isolated polypeptide according to the invention comprises or consists of an amino acid sequence according to SEQ ID NO.:9, wherein said polypeptide is capable of binding to and inhibiting the activity of the CCR6 receptor.

Whether a polypeptide according to the invention is capable of binding to the CCR6 receptor may be determined by any suitable method known to the skilled person. For example, the skilled person my determine whether a polypeptide is capable of binding to the CCR6 receptor by using a yeast two-hybrid assay or a biochemical assay such as e.g. a pull-down assay, a co-immunoprecipitation assay, an enzyme-linked immunosorbent assay (ELISA), a quantitative radioligand binding assay, a fluorescence-activated cell sorting (FACS)-based assay, a Plasmon resonance assay or any other method known to the skilled person. When using pull-down or Plasmon resonance assays, it is useful to fuse at least one of the proteins to an affinity tag such as HIS-tag, GST-tag or other, as is well known in the art of biochemistry.

The term "inhibiting the activity of the CCR6 receptor" as used herein means that CCR6 receptor activity is downregulated or abolished and/or that the activation of CCR6 receptor is inhibited.

For example, in one embodiment an isolated polypeptide according to the invention or any other compound capable of inhibiting the activity and/or the expression of the CCR6 receptor described herein may sterically block the CCR6 receptor, such that a CCR6 receptor agonist (e.g. CCL18 or CCL20) cannot activate the receptor. Thus, an inhibition of CCR6 receptor activity may e.g. be due to an inhibition of the interaction of the CCR6 receptor with one of its ligands, i.e. CCL18 and/or CCL20, by a polypeptide or any other compound that binds to the CCR6 receptor but does not mediate a signaling event by itself.

In another embodiment an isolated polypeptide according to the invention or any other compound capable of inhibiting the activity and/or the expression of the CCR6 receptor may down regulate or abolish existing CCR6 receptor activity.

Whether an isolated polypeptide according to the invention or any other compound to be tested is capable of inhibiting the activity of the CCR6 receptor may e.g. be determined by measuring cell surface expression of CCR6 as described herein below in example 6 and FIGS. 13 and 14, wherein an inhibition of CCR6 receptor internalisation in presence of a CCR6 receptor agonist (such as e.g. CCL18) and the isolated polypeptide or other compound to be tested, in comparison to a control (e.g. presence of CCR6 receptor agonist only) indicates that the isolated polypeptide or other compound is capable of inhibiting the activity of the CCR6 receptor.

In another example, the skilled person may also determine the ability of an isolated polypeptide according to the invention or any other compound to be tested to inhibit CCR6 receptor activity by incubating CCR6 expressing cells in the presence of a CCR6 receptor agonist, such as e.g. CCL18 or CCL20, and in the presence or absence of the isolated polypeptide or other compound to be tested and subsequently lysing the cells and analysing phosphorylation of ERK, a downstream molecule of CCR6 signaling, by Western blot analysis. In this example a lower level of phosphorylation of ERK in the presence of the polypeptide or other compound to be tested versus the level of phosphorylation of ERK in the absence of the isolated polypeptide or other compound to be tested indicates that the polypeptide or other compound is capable of inhibiting the activity of the CCR6 receptor. One method for determining ERK phosphorylation by Western Blot analysis is e.g. described in Lin et al. J Proteome Res. 2010 January; 9(1):283-97. In an analogous example, the phosphorylation of other CCR6 downstream effectors such as e.g. Akt, SAPK/JNK kinases, phosphatidylinositol 3-kinase or phospholipase C may be analysed in order to determine whether an isolated polypeptide according to the invention or any other compound to be tested is capable of inhibiting CCR6 receptor activity.

Whether an isolated polypeptide according to the invention or any other compound to be tested is capable of inhibiting the activity of the CCR6 receptor may e.g. also be determined by measuring CCL18 stimulated FGF2 release or CCL18 mediated induction of collagen and/or α-SMA in the presence of said polypeptide or other compound as e.g. described herein below in example 4 and FIGS. 4 and 5. In this example an inhibition of CCL18 induced FGF2 up regulation and/or an inhibition of the CCL18 mediated induction of collagen and/or α-SMA expression in the presence of the polypeptide or other compound to be tested in comparison to a control, to which the polypeptide or other compound has not been added, indicates that the isolated polypeptide or other compound is capable of inhibiting the activity of the CCR6 receptor. Furthermore, in order to determine the ability of an isolated polypeptide according to the invention or any other compound to be tested to inhibit the activity of the CCR6 receptor, the skilled person may also determine whether the induction of Epithelial-Mesenchymal-Transition (EMT) by CCL18 is down regulated or abolished.

Alternatively or additionally any further methods which are suited to determine the activity of the CCR6 receptor and which are comprised in the art and known to the average skilled person may be used.

An isolated polypeptide according to the invention or any other compound which is capable of inhibiting the activity of the CCR6 receptor, may inhibit the activity of the CCR6 receptor by at least 10%, at least 20%, at least 30%, at least 40%, at least 50%, at least 60%, at least 70%, more preferably at least 80%, at least 90%, at least 91%, at least 92%, at least 93%, at least 94%, at least 95%, at least 96%, at least 97%, at least 98% or at least 99% when compared to a control. In some preferred embodiments a polypeptide according to the invention or any other compound described herein, which is capable of inhibiting the activity of the CCR6 receptor, may inhibit the activity of the CCR6 receptor by 100%.

In another aspect the present invention relates to an isolated polynucleotide encoding the isolated polypeptide according to the invention.

In a preferred embodiment, the isolated polynucleotide according to the invention has a length of less than 6000 nucleotides, less than 5000 nucleotides, less than 4000 nucleotides, less than 3000 nucleotides, less than 2000 nucleotides, less than 1000 nucleotides or less than 500 nucleotides.

In a further preferred embodiment the isolated polynucleotide according to the invention has a length of between at least 24 and 9000 nucleotides, preferably at least 24 and 8000 nucleotides, more preferably between at least 24 and 7000 nucleotides, more preferably between at least 24 and 6000 nucleotides, more preferably between at least 24 and 5000 nucleotides, more preferably between at least 24 and 4000 nucleotides, more preferably between at least 24 and 3000 nucleotides, more preferably between at least 24 and 2000 nucleotides, more preferably between at least 24 and 1000 nucleotides or even more preferably between at least 24 and 500 nucleotides. In another preferred embodiment an isolated polynucleotide according to the invention has a length of at least 24, at least 87 or at least 93 nucleotides.

In another preferred embodiment the isolated polynucleotide according to the invention has a length of between at least 87 and 9000 nucleotides, preferably at least 87 and 8000 nucleotides, more preferably between at least 87 and 7000 nucleotides, more preferably between at least 87 and 6000 nucleotides, more preferably between at least 87 and 5000 nucleotides, more preferably between at least 87 and 4000 nucleotides, more preferably between at least 87 and 3000 nucleotides, more preferably between at least 87 and 2000 nucleotides, more preferably between at least 87 and 1000 nucleotides or even more preferably between at least 87 and 500 nucleotides.

In another preferred embodiment an isolated polynucleotide according to the invention has a length of at least 87 nucleotides, at least 100 nucleotides, at least 200 nucleotides, at least 500 nucleotides, at least 800 nucleotides, at least 1000 nucleotides, at least 1500 nucleotides, at least 2000 nucleotides, at least 2500 nucleotides, at least 3000 nucleotides or at least 3500 nucleotides. In a particularly preferred embodiment an isolated polynucleotide according to the invention has a length of at least 87 nucleotides or at least 100 nucleotides.

In another preferred embodiment the isolated polynucleotide according to the invention has a length of between at least 93 and 9000 nucleotides, preferably at least 93 and 8000 nucleotides, more preferably between at least 93 and 7000 nucleotides, more preferably between at least 93 and 6000 nucleotides, more preferably between at least 93 and 5000 nucleotides, more preferably between at least 93 and 4000 nucleotides, more preferably between at least 93 and 3000 nucleotides, more preferably between at least 93 and 2000 nucleotides, more preferably between at least 93 and 1000 nucleotides or even more preferably between at least 93 and 500 nucleotides.

In another preferred embodiment an isolated polynucleotide according to the invention has a length of at least 24 nucleotides, at least 50 nucleotides, at least 87 nucleotides, at least 93 nucleotides, at least 100 nucleotides, at least 200 nucleotides, at least 500 nucleotides, at least 800 nucleotides, at least 1000 nucleotides, at least 1500 nucleotides, at least 2000 nucleotides, at least 2500 nucleotides, at least 3000 nucleotides or at least 3500 nucleotides. In a particularly preferred embodiment the isolated polynucleotide according to the invention has a length of at least 24, at least 87 or at least 93 nucleotides.

It will be apparent to the skilled person that due to the degeneracy of the genetic code a given polypeptide according to the invention may be encoded by different nucleotide sequences.

In a preferred embodiment the isolated polynucleotide according to the invention comprises or consists of a sequence which exhibits at least 80% identity to the sequence according to SEQ ID NO.:24, SEQ ID NO.:25 or SEQ ID NO.:26.

In a further preferred embodiment the polynucleotide according to the invention comprises or consists of a sequence which exhibits at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:24, SEQ ID NO.:25 or SEQ ID NO.:26. In a particularly preferred embodiment the polynucleotide according to the invention comprises or consists of a sequence which exhibits at least 85%, preferably at least 90%, more preferably at least 95% or even more preferably at least 98% identity to the sequence according to SEQ ID NO.:24, SEQ ID NO.:25 or SEQ ID NO.:26.

In another preferred embodiment the polynucleotide according to the invention comprises or consists of a sequence which exhibits at least 80%, at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:24. In another preferred embodiment the polynucleotide according to the invention comprises or consists of a sequence which exhibits at least 80%, at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:25. In a further preferred embodiment the polynucleotide according to the invention comprises or consists of a sequence which exhibits at least 80%, at least 85%, preferably at least 90%, more preferably at least 91%, even more preferably at least 92%, even more preferably at least 93%, even more preferably at least 94%, even more preferably at least 95%, even more preferably at least 96%, even more preferably at least 97%, even more preferably at least 98% or even more preferably at least 99% identity to the sequence according to SEQ ID NO.:26.

In a particularly preferred embodiment the isolated polynucleotide according to the invention comprises or consists of a sequence which exhibits 100% identity to the sequence according to SEQ ID NO.:24, SEQ ID NO.:25 or SEQ ID NO.:26. In another particularly preferred embodiment the isolated polynucleotide according to the invention comprises or consists of a sequence according to SEQ ID NO.:24, SEQ ID NO.:25 or SEQ ID NO.:26.

An isolated polynucleotide according to the invention may be a single or double stranded RNA or DNA molecule.

In some embodiments the isolated polynucleotide according to the invention may be inserted into an expression vector. The expression vector may be a prokaryotic or eukaryotic expression vector such as e.g. a plasmid, a minichromosome, a cosmid, a bacterial phage, a retroviral vector or any other vector known to the skilled person. The skilled person will be familiar with how to select an appropriate vector according to the specific need.

The present invention thus also relates to an expression vector comprising a polynucleotide according to the invention.

In a further aspect the present invention relates to a method for identifying a compound capable of inhibiting the activity of the CCR 6 receptor, wherein the method comprises the steps of:
(a) contacting a CCR6 receptor with a test compound;
(b) adding a CCR6 receptor agonist, wherein said agonist is a polypeptide comprising or consisting of an amino acid sequence which exhibits at least 80% identity to the sequence according to SEQ ID NO.:5 or SEQ ID NO.:18;
(c) determining the activity of said CCR 6 receptor; and
(d) selecting said test compound as the compound capable of inhibiting the activity of the CCR 6 receptor if the CCR6 receptor activity determined in (c) is lower than the CCR 6 receptor activity determined in a control.

In a preferred embodiment of the aforementioned method, the steps (a), (b), (c), (d) are carried out in that order.

In a preferred embodiment the CCR6 receptor in (a) is expressed by a cell, preferably on the surface of a cell. In another preferred embodiment the CCR6 receptor in (a) is recombinant CCR6 receptor, preferably purified recombinant CCR6 receptor. If the CCR6 receptor in (a) is expressed by a cell, preferably on the surface of a cell, said cell may e.g. be comprised in a cell-based reaction system. In a preferred embodiment said cell is selected from the group consisting of a fibroblast, an alveolar epithelial cell, a lymphocyte and a lung cell. In a further preferred embodiment said cell is selected from the group consisting of a fibroblast, an alveolar epithelial cell, a lymphocyte and a lung cell, wherein the cell is derived from a patient suffering from an interstitial lung disease or a cancer. In a preferred embodiment said interstitial lung disease is idiopathic pulmonary fibrosis and said cancer is an adenocarcinoma, preferably an adenocarcinoma of the lung.

If the CCR6 receptor in (a) is recombinant CCR6 receptor, preferably purified recombinant CCR6 receptor, the CCR6 receptor may be comprised in a cell-free reaction system. The CCR6 receptor agonist in (b) may then be added to the cell-based or cell-free reaction system.

The term "reaction system" in this context is meant to refer to an experimental set up in which the cells expressing the CCR6 receptor or the recombinant CCR6 receptor are placed into a cell culture tube, tissue culture tube, Eppendorf tube, reaction chamber or other containment device containing the necessary buffers and/or other reagents suitable to perform the aforementioned method and in which the method is performed in said cell culture tube, tissue culture tube, Eppendorf tube, reaction chamber or other containment device. The aforementioned method may in some embodiments thus further comprise the step of providing a cell-based or cell-free reaction system comprising the CCR 6 receptor. If the method comprises said step, it is preferred that said step is step (a), i.e., the first step, of the method.

Preferably, the CCR6 receptor is human CCR6 receptor. In one preferred embodiment said CCR6 receptor is a polypeptide encoded by the sequence according to SEQ ID NO.: 3 or SEQ ID NO.: 4. In another preferred embodiment said CCR6 receptor is a polypeptide according to SEQ ID NO.: 27.

In a preferred embodiment said test compound is an antibody, a small molecule or a peptide. Preferably, the antibody is a monoclonal or polyclonal antibody. In some embodiments the antibody may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments.

In another preferred embodiment the polypeptide according to (b) comprises or consists of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 5. In a particularly preferred embodiment the polypeptide according to (b) comprises or consists of an amino acid sequence which exhibits at least 95%, at least 98% or 100% identity to the sequence according to SEQ ID NO.: 5.

In a further preferred embodiment the polypeptide according to (b) comprises or consists of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18. In a particularly preferred embodiment the polypeptide according to (b)

comprises or consists of an amino acid sequence which exhibits at least 95%, at least 98% or 100% identity to the sequence according to SEQ ID NO.: 18.

In a further preferred embodiment the polypeptide according to (b) comprises or consists of an amino acid sequence which comprises at least 8, 9, 10, 11, 12, 13, 14, 15, 16, 20, 30, 50, or 60 contiguous amino acids of the sequence according to SEQ ID NO:5.

In a further preferred embodiment the polypeptide according to (b) comprises or consists of an amino acid sequence which comprises at least 8, 9, 10, 11, 12, 13, 14, 15, 16, 20, 30, 50, or 60 contiguous amino acids of the sequence according to SEQ ID NO:18.

In another preferred embodiment the polypeptide according to (b) comprises or consists of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 5 and which comprises at least 30 or at least 50 contiguous amino acids of the sequence according to SEQ ID NO:5.

In yet another preferred embodiment the polypeptide according to (b) comprises or consists of an amino acid sequence which exhibits at least 85%, at least 90%, at least 91%, at least 92%, at least 93%, at least 94%, at least 95%, at least 96%, at least 97%, at least 98%, at least 99% identity to the sequence according to SEQ ID NO.: 18 and which comprises at least 30 or at least 50 contiguous amino acids of the sequence according to SEQ ID NO:18. In a particularly preferred embodiment the polypeptide according to (b) is a polypeptide according to SEQ ID NO:18.

The activity of the CCR6 receptor may e.g. be determined by any of the methods for determining CCR6 receptor activity described herein above.

The choice of a suitable control depends on the method used for determining CCR6 receptor activity. The skilled person will know how to select a suitable control. Some suitable examples for determining CCR6 receptor activity and suitable controls are described herein below in the example section.

A control may e.g. be a sample in which the activity of the CCR 6 receptor has only been determined in the presence of the CCR6 receptor agonist and in the absence of the test compound.

In a preferred embodiment the CCR6 receptor activity determined in (c) is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% lower than the CCR6 receptor activity in the control.

In a particular preferred embodiment the CCR6 receptor activity determined in (c) is at least 60%, at least 70%, at least 80%, at least 90%, at least 95% or at least 98% lower than the CCR6 receptor activity in the control.

In another preferred embodiment the CCR6 receptor activity determined in (c) is 100% lower than the CCR6 receptor activity in the control.

In a further preferred embodiment the CCR6 receptor activity determined in (c) is at least 2 fold, at least 3 fold, at least 4 fold, at least 5 fold, at least 6 fold, at least 7 fold, at least 8 fold, at least 9 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or at least 10000 fold lower than the CCR6 receptor activity in the control.

The present invention also provides a method for detecting an interstitial lung disease or cancer in a subject comprising the step of determining the level of CCR6 gene expression in a sample from said subject.

Said method is preferably performed in vitro.

Preferably, the CCR6 receptor is human CCR6 receptor. In a preferred embodiment said CCR6 receptor is a polypeptide encoded by the sequence according to SEQ ID NO.: 3 or SEQ ID NO.: 4. In another preferred embodiment said CCR6 receptor is a polypeptide according to SEQ ID NO.: 27.

In one embodiment, determining the level of CCR6 expression may be achieved by contacting the sample from the subject with a detecting agent specific for CCR6. A detecting agent is specific for a CCR6, if it binds CCR6 with a higher affinity than any other compound in a sample (i.e. a non-target). Preferably, a detecting agent is specific for CCR6 if it binds to CCR6 only and does not bind at all to a non-target.

The present invention also provides a method for detecting or grading cancer in a subject comprising the step of determining the level of CCL18 gene expression in a sample from said subject.

The term "grading cancer" as used herein refers to classifying the cancer by determining certain features of the cancer, such as e.g. its aggressiveness and its prognosis. In one preferred embodiment "grading cancer", preferably adenocarcinoma, may be performed by correlating the amount of CCL18 determined in the sample from the subject to cancer grade, preferably the grade of adenocarcinoma, most preferably the grade of adenocarcinoma of the lung.

In one embodiment, determining the level of CCL18 expression may be achieved by contacting the sample from the subject with a detecting agent specific for CCL18. A detecting agent is specific for CCL18, if it binds CCL18 with a higher affinity than any other compound in a sample (i.e. a non-target). Preferably, a detecting agent is specific for CCL18 if it binds to CCL18 only and does not bind at all to a non-target.

"Determining the level of CCR6 gene expression" means that the level or amount of CCR6 mRNA and/or protein may be determined. In some embodiments the cell surface expression of CCR6 receptor may be determined. "Determining the level of CCL18 gene expression" means that the level or amount of CCL18 mRNA and/or protein may be determined. In a preferred embodiment said CCL18 is a polypeptide according to SEQ ID NO.: 18.

CCR6 mRNA expressions or CCL18 mRNA expression may e.g. be determined by in situ hybridization, northern blotting, RNAse protection assays or PCR-based methods, such as e.g. reverse transcription PCR or real time quantitative PCR. The skilled person will know how to perform these methods.

In some embodiments total RNA may be isolated from the sample from the subject prior to determining the amount of mRNA.

Suitable detecting agents that may be employed for determining the level of CCR6 mRNA expression are e.g. antisense oligonucleotide probes specific for CCR6 mRNA. Suitable detecting agents that may be employed for determining the level of CCL18 mRNA expression are e.g. antisense oligonucleotide probes specific for CCL18 mRNA. The antisense oligonucleotide probes may be RNA or DNA oligonucleotide probes. In a preferred embodiment, the oligonucleotide probe is a single stranded RNA molecule.

The oligonucleotide probe is specific for CCR6 mRNA if it is capable of hybridizing to CCR6 mRNA under highly stringent conditions. The oligonucleotide probe is specific for CCL18 mRNA if it is capable of hybridizing to CCL18 mRNA under highly stringent conditions.

As used herein the term "hybridize" or "hybridizes" refers to the hybridization of a first to a second polynucleotide. To determine, if two polynucleotides hybridize to each other, the skilled person will preferably conduct hybridization experiments in vitro under moderate or stringent hybridization conditions. Hybridization assays and conditions are known to those skilled in the art and can be found, for example, in Current Protocols in Molecular Biology, John Wiley & Sons, N. Y., 6.3.1-6.3.6, 1991. Stringent conditions may e.g. be conditions in which hybridization takes place in 6× sodium chloride/sodium citrate (SSC) at 45° C., followed by a wash in 0.2×SSC, 0.1% SDS at 65° C.

A preferred detecting agent for detecting CCR6 protein or CCL18 protein is an antibody or an aptamer. Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments. In one preferred embodiment commercially available antibodies specific for CCR6 or CCL18 may be used. One examples of a commercially available antibody is the anti-human CCR6 mAb described herein below in example 1.

In a preferred embodiment, a detecting agent as described herein above may comprise a detectable label. Any suitable label, which can be attached to the detecting agent may be used. In one preferred embodiment the detectable label is covalently or non-covalently attached to the detecting agent. Examples of labels that may be attached to the detecting agent include e.g. fluorescent dyes such as e.g. Cyanine dyes, e.g. Cyanine 3, Cyanine 5 or Cyanine 7, Alexa Fluor dyes, e.g. Alexa 594, Alexa 488 or Alexa 532, fluorescein family dyes, R-Phycoerythrin, Texas Red, rhodamine and Fluoresceinisothiocyanat (FITC). Detecting agents may also be labeled with enzymes such as e.g. horseradish peroxidase, alkaline phosphatase or beta-lactamase, radioisotopes such as e.g. $^3$H, $^{14}$C, $^{32}$P, $^{33}$P, $^{35}$S or $^{125}$I, metal such as e.g. gold or with biotin. In another preferred embodiment the detecting agent may also be detected by a secondary detecting agent comprising a label as described above.

Preferably a secondary detecting agent is capable of specifically binding to the above described detecting agent. In a particularly preferred embodiment a secondary detecting agent is an antibody.

In some embodiments the level of CCR6 expression or CCL18 expression may e.g. be detected in methods involving histological or cell-biological procedures. In some embodiments, visual techniques, such as light microscopy, immunofluoresence microscopy or electron microscopy, or flow cytometry or luminometry may be used. In a preferred embodiment the level of CCR6 expression or CCL18 expression is detected by immunohistochemistry.

The terms "detecting an interstitial lung disease" or "detecting cancer" as used herein means that the presence of an interstitial lung disease or a cancerous disease or disorder may be identified in a subject or in a sample from a subject. Preferably, said subject is previously not known to suffer from an interstitial lung disease or cancer respectively. In one preferred embodiment the subject is suspected to suffer from an interstitial lung disease or cancer.

In order to detect an interstitial lung disease or cancer in a subject, determining the level of CCR6 gene expression in the sample from the subject may in some embodiments be performed alongside measuring or determining the amount of other compounds or factors indicative of an interstitial lung disease or cancer respectively. For example, known markers for interstitial lung disease, such as e.g. serum markers surfactant protein (SP) A and D, or known cancer markers may be detected in the same sample or in a different sample from the subject. Further suitable markers are known to the skilled person. In some embodiments the skilled person may, in addition to determining the level of CCR6 gene expression in the sample from the subject, also examine the histological pattern of the sample to further examine whether the subject suffers from an interstitial lung disease or cancer.

In order to detect cancer in a subject, determining the level of CCL18 gene expression in the sample from the subject may in some embodiments be performed alongside measuring or determining the amount of other compounds or factors indicative of cancer. For example, known cancer markers may be detected in the same sample or in a different sample from the subject. Further suitable markers are known to the skilled person. In some embodiments the skilled person may, in addition to determining the level of CCL18 gene expression in the sample from the subject, also examine the histological pattern of the sample to further examine whether the subject suffers from cancer.

In a preferred embodiment the afore-described method further comprises the step of comparing the level of CCR6 gene expression determined in the sample from the subject to the level of CCR6 gene expression in a control, wherein a higher level of CCR6 gene expression determined in the sample from the subject in comparison to the control indicates the presence of an interstitial lung disease or a cancer in the subject.

In a another preferred embodiment the afore-described method further comprises the step of comparing the level of CCL18 gene expression determined in the sample from the subject to the level of CCL18 gene expression in a control, wherein a higher level of CCL18 gene expression determined in the sample from the subject in comparison to the control indicates the presence of cancer in the subject.

In one preferred embodiment the control is a sample from a healthy subject. In a preferred embodiment a higher level of CCR6 expression determined in the sample from the subject in comparison to the control indicates the presence of an interstitial lung disease or a cancer in the subject. In another preferred embodiment a higher level of CCL18 expression determined in the sample from the subject in comparison to the control indicates the presence of cancer in the subject. The term "higher level" means that the level of CCR6 expression or CCL18 expression determined in the sample from the subject is at least 2 fold, preferably at least 3 fold, at least 4 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or at least 10000 fold higher than in the control. Most preferably, the level of CCR6 expression or CCL18 expression determined in the sample from the subject is at least 2 fold, at least 3 fold, at least 10 fold, at least 50 fold, at least 100 fold or at least 1000 fold higher than in the control.

In another preferred embodiment the control may also be a sample derived from a subject known to suffer from an interstitial lung disease or cancer (control subject), i.e. a subject that has been independently diagnosed with an interstitial lung disease or cancer, wherein the cancer is preferably an adenocarcinoma, most preferably an adenocarcinoma of the lung. In such cases a higher level of CCR6 gene expression or CCL18 gene expression determined in the sample from the subject in comparison to the control indicates a further progression of the interstitial lung disease or the cancer in the subject from which the sample was derived in comparison to the control subject.

In a further preferred embodiment the control may also be healthy tissue derived from an affected organ of a subject known or suspected to suffer from an interstitial lung disease or cancer, wherein the cancer is preferably an adenocarcinoma, most preferably an adenocarcinoma of the lung. In such cases it is preferred that the sample to be tested (i.e. the sample from the subject) is derived from an affected (i.e. diseased) part of said organ or a part of said organ which is suspected to be affected and the control is derived from a healthy part of the same organ. The term "affected organ" in this context means an organ which is affected by the disease, i.e. by an interstitial lung disease or cancer.

In the context of the present invention, the control is preferably separated from the body of the subject it is derived from.

In some preferred embodiments the aforementioned method according to the invention may also be used to monitor the efficacy of treatment of an interstitial lung disease or cancer in vitro. The efficacy of treatment of an interstitial lung disease or cancer may e.g. be monitored by detecting the level of CCR6 expression in different samples from a subject that were provided over a given period of time while the subject from which the samples were derived was subjected to treatment of an interstitial lung disease or cancer. An increase or decrease in the level of CCR6 expression in samples provided from the subject over a given period of time may then indicate the efficacy of treatment.

The efficacy of treatment of cancer may e.g. also be monitored by detecting the level of CCL18 expression in different samples from a subject that were provided over a given period of time while the subject from which the samples were derived was subjected to treatment of cancer. An increase or decrease in the level of CCL18 expression in samples provided from the subject over a given period of time may then indicate the efficacy of treatment.

In one preferred embodiment the level of CCR6 expression in the control may be determined in parallel to the level of CCR6 expression in the sample from the subject. In a further preferred embodiment the level of CCL18 expression in the control may be determined in parallel to the level of CCL18 expression in the sample from the subject.

In another preferred embodiment the control may be a predetermined value. Such a value may e.g. be based on the results of previous experiments determining the amounts of CCR6 expression levels or CCL18 expression levels in one or more samples from a healthy subject or a subject known to suffer from an interstitial lung disease or cancer. In some embodiments a predetermined value may be derivable from a database.

In one preferred embodiment the level of CCR6 expression may be compared to more than one control, e.g. to 2, 3, 4, 5, 6, 7, 8, 9, 10, 20, 30, 40, 50, 60, 70, 80, 90, 100 or more than 100 controls. In another preferred embodiment the level of CCL18 expression may be compared to more than one control, e.g. to 2, 3, 4, 5, 6, 7, 8, 9, 10, 20, 30, 40, 50, 60, 70, 80, 90, 100 or more than 100 controls.

Preferably, the sample from the subject used in the methods according to the invention is separated from the body of the subject. The sample is preferably a solid sample. In a preferred embodiment the sample from the subject is a tissue sample, preferably a lung tissue sample. Tissue samples may e.g. be fresh or frozen tissue samples or fixed paraffin embedded samples. In one preferred embodiment the sample may be a biopsy or resection sample. In another preferred embodiment the sample is a fibroblast cell line established from surgical material or from material obtained from fibrotic lungs as e.g. described herein below in example 1. In a further preferred embodiment the sample is a bronchial brushing sample.

In some embodiments the sample from the subject is a liquid, preferably a body fluid.

In a preferred embodiment, the body fluid is selected from the group consisting of blood, plasma, bronchoalveolar lavage fluid, pleural effusion, sputum, saliva, serum or urine.

In some embodiments, a liquid sample may be enriched for cells of interest, e.g. circulating fibrocytes or T cells if the sample is used to examine whether the subject suffers from an interstitial lung disease or cancer cells if the sample is used to examine whether the subject suffers from cancer.

Enrichment may be performed by any method known to the skilled person.

Enrichment may e.g. be achieved by using a solid support, e.g. a column, coated with a specific antibody, such as e.g. an antibody specific for T cells if T cells are to be enriched or an antibody specific for a lung cancer antigen if lung cancer cells are to be enriched. Alternatively, enrichment may e.g. also be achieved by using filtration methods, such as e.g. filtration through mesh gauze, or by immobilizing specific aptamers on a microfluidic channel and pumping the liquid sample through the device.

In a further aspect the present invention also relates to a diagnostic kit for detecting an interstitial lung disease or cancer comprising a detecting agent specific for a CCR6 polynucleotide or a CCR6 polypeptide.

Preferably, said CCR6 polynucleotide is CCR6 mRNA.

In a preferred embodiment, said detecting agent is an antibody, an aptamer or an oligonucleotide probe.

Antibodies and oligonucleotide probes suitable for the detection of a CCR6 polynucleotide, in particular CCR6 mRNA, and a CCR6 polypeptide have been described herein above.

In a further aspect the present invention also relates to a diagnostic kit for detecting cancer comprising a detecting agent specific for a CCL18 polynucleotide or a CCL18 polypeptide.

Preferably, said CCL18 polynucleotide is CCL18 mRNA.

In a preferred embodiment, said detecting agent is an antibody, an aptamer or an oligonucleotide probe.

Antibodies and oligonucleotide probes suitable for the detection of a CCL18 polynucleotide, in particular CCL18 mRNA, and a CCL18 polypeptide have been described herein above.

In a preferred embodiment the diagnostic kit further comprises additional components or reagents that are suitable for performing the methods according to the invention, such as e.g. buffers or controls. In another preferred embodiment the components contained in the diagnostic kit are comprised in one or more containers. The diagnostic kit according to the present invention may also comprise an instruction leaflet, which indicates how to use the diagnostic kit and its components.

The present invention in a further aspect also relates to a pharmaceutical composition comprising a compound capable of inhibiting the activity and/or the expression of the CCR6 receptor.

A pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures.

In a preferred embodiment a pharmaceutical composition according to the invention is administered parenterally, e.g. in form of solutions for injection or infusion, orally, e.g. in the form of a tablet, pill, lozenge or capsule or via inhalation.

For the production of pills, tablets, sugar-coated tablets and hard gelatin capsules for example, lactose, starch, for example maize starch, or starch derivatives, talc, stearic acid or its salts, etc may be used. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc.

In some embodiments the pharmaceutical compositions also contains additives, such as for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Examples of suitable excipients for the various different forms of pharmaceutical compositions described herein may e.g. be found in the "Handbook of Pharmaceutical Excipients", 2nd Edition, (1994), Edited by A Wade and P J Weller.

In a preferred embodiment the compound capable of inhibiting the activity and/or the expression of the CCR6 receptor is selected from the group consisting of a polypeptide according to the invention, a small molecule capable of binding to the CCR6 receptor, the isolated polynucleotide according to the invention, an aptamer specific for CCR6 receptor, an antibody specific for CCR6 receptor, an antisense molecule suitable for reducing or inhibiting the expression of the CCR6 receptor and an siRNA molecule suitable for reducing or inhibiting the expression of the CCR6 receptor.

Small molecules capable of binding to the CCR6 receptor may e.g. be identified by screening small compound libraries.

Whether a small molecule is capable of binding to the CCR6 receptor may e.g. be determined by the same methods as described herein above. Analogous methods may e.g. also be used in order to determine whether a small molecule is capable of binding to CCL18 or CCL20.

The term "aptamer" as used herein refers to a DNA, RNA or peptide aptamer specific for the CCR6 receptor, for CCL18 or for CCL20 respectively.

A polynucleotide aptamer is preferably between about 10 to about 300 nucleotides in length. Preferably an aptamer is between about 30 to about 100 nucleotides in length. Most preferably an aptamer is between about 10 to 60 nucleotides in length.

Aptamers may be prepared by any known method, including synthetic, recombinant, and purification methods, and may be used alone or in combination with other aptamers specific for CCR6, for CCL18 or for CCL20.

An antibody specific for the CCR6 receptor may be a monoclonal or polyclonal antibody. In some embodiments the antibody may also be selected from antibody variants or fragments such as e.g. single chain antibodies, diabodies, minibodies, single chain Fv fragments (sc(Fv)), sc(Fv)$_2$ antibodies, Fab fragments or a F(ab')2 fragments, provided that said antibody variants or fragments are specific for the CCR6 receptor.

The term "antisense molecule suitable for reducing or inhibiting the expression of the CCR6 receptor" refers to a polynucleotide which is complementary to CCR6 mRNA. It is preferred that said antisense molecule is suitable for use in an antisense approach to inhibit translation of CCR6 mRNA in a cell. Said antisense molecule may be a DNA or RNA molecule and may be single stranded or double stranded. In a preferred embodiment, the antisense molecule is a single stranded DNA molecule or a double or single stranded RNA molecule.

An antisense molecule preferably has a length of about 10 to about 500 nucleotides, of about 11 to about 200 nucleotides, of about 12 to about 100 nucleotides, about 13 to about 75 nucleotides or of about 14 to about 50 nucleotides, of about 15 to about 40 nucleotides, of about 16 to about 30 nucleotides or of about 17 to about 25 nucleotides.

An siRNA molecule suitable for reducing or inhibiting the expression of the CCR6 receptor may be a single stranded or double stranded siRNA molecule that is capable of hybridizing to CCR6 mRNA, thereby inducing RNA interference or any other intracellular antisense mechanism that results in reduction or inhibition of the expression of CCR6 protein.

The siRNA molecule may be of any sequence that allows the siRNA molecule to induce RNA interference resulting in reduction or inhibition of the expression of CCR6 protein.

Preferably, the siRNA molecule has a length of between 10 and 100, between 12 and 80, between 14 and 60, between 16 and 50, between 17 and 40, more preferably between 18 and 30 nucleotides and most preferably between 18 and 26 nucleotides.

In another preferred embodiment, a pharmaceutical composition according to the invention comprises a further active compound suitable for the treatment or prevention of an interstitial lung disease and/or cancer.

Examples of further active compound suitable for the treatment of an interstitial lung disease are e.g. anti-inflammatory drugs such as e.g. prednisone or other corticosteroids, azathioprine, methotrexate, mycophenolate or cyclophosphamide, antioxidants, such as e.g. acetylcysteine antifibrotic agents, such as e.g. bosentan or pirfenidone, minocycline, sildenafil, thalidomide, anti-TNF antibodies, such as e.g. Infliximab; etanercept, interferon gamma, anti-IL-13 antibodies, endothelin inhibitors, Zileuton, anticoagulants, macrolides, phosphodiesterase (PDE) 4 inhibitors, such as e.g. roflumilast, Aviptadil, alpha-melanocyte-stimulating hormone (alpha-MSH), tyrosine kinase inhibitors, such as e.g. imatinib, dasatinib and nilotinib.

The further active compound suitable for the treatment of cancer is preferably a chemotherapeutic agent. Chemotherapeutic agents suitable for the treatment of cancer are well known to the skilled person. Examples of chemotherapeutic agents are e.g. temozolomide, adriamycin, doxorubicin, epirubicin, 5-fluorouracil, cytosine arabinoside ("Ara-C"), cyclophosphamide, thiotepa, busulfan, cytoxin, taxoids, e.g., paclitaxel, toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, melphalan and other related nitrogen mustards and hormonal agents that act to regulate or inhibit hormone action on tumors such as tamoxifen and onapristone.

The pharmaceutical composition according to the invention may comprise one or more than one further active compound suitable for the treatment or prevention of an interstitial lung disease and/or one or more than one further active compound suitable for the treatment or prevention of cancer. In a preferred embodiment the pharmaceutical composition according to the invention comprises 1, 2, 3, 4, 5, 6, 7, 8, 9, 10 or more than 10 further active compounds suitable for the treatment of prevention of an interstitial lung disease and/or 1, 2, 3, 4, 5, 6, 7, 8, 9, 10 or more than 10 further active compound suitable for the treatment of cancer.

In other preferred embodiments one or more separate compositions comprising an active compound suitable for the treatment or prevention of an interstitial lung disease and/or an active compound suitable for the treatment or prevention of cancer may be administered to a subject, preferably a human subject, in combination with a pharmaceutical composition according to the invention comprising a compound capable of inhibiting the activity and/or the expression of the CCR6 receptor.

In a further aspect the present invention relates to a pharmaceutical composition according to the invention for use in the treatment or prevention of an interstitial lung disease and/or cancer.

In another aspect the present invention relates to the use of a compound capable of inhibiting the activity and/or the expression of the CCR6 receptor or a pharmaceutical composition according to the invention for the manufacture of a medicament for the treatment or prevention of an interstitial lung disease and/or cancer.

In a preferred embodiment of the use according to the invention, the compound capable of inhibiting the activity and/or the expression of the CCR6 receptor is selected from the group consisting of the isolated polypeptide according to the invention, a small molecule capable of binding to the CCR6 receptor, an isolated polynucleotide encoding the isolated polypeptide according to the invention, an aptamer specific for CCR6 receptor, an antibody specific for CCR6 receptor, an antisense molecule suitable for reducing or inhibiting the expression of the CCR6 receptor and an siRNA molecule suitable for reducing or inhibiting the expression of the CCR6 receptor. Such compounds capable of inhibiting the activity and/or the expression of the CCR6 receptor have been described herein above. In a particularly preferred embodiment of the use according to the invention, the compound capable of inhibiting the activity and/or the expression of the CCR6 receptor is selected from the group consisting of the isolated polypeptide according to the invention and an isolated polynucleotide encoding the isolated polypeptide according to the invention.

The present invention also relates to the use of a compound capable of inhibiting the activity and/or the expression of CCL18 or CCL20 for the manufacture of a medicament for the treatment or prevention of an interstitial lung disease and/or cancer.

In a preferred embodiment of the aforementioned use according to the invention the compound capable of inhibiting the activity and/or the expression of the CCL18 or CCL20 is selected from the group consisting of a small molecule capable of binding to CCL18 or CCL20, an aptamer specific for CCL18 or CCL20, an antibody specific for CCL18 or CCL20, an antisense molecule suitable for reducing or inhibiting the expression of CCL18 or CCL20 and an siRNA molecule suitable for reducing or inhibiting the expression of CCL18 or CCL20.

The present invention also relates to the use of a detecting agent selected from the group consisting of:
(a) a detecting agent specific for a polynucleotide encoding CCR6 receptor;
(b) a detecting agent specific for CCR6 receptor;
(c) a detecting agent specific for a polynucleotide encoding CCL18;
(d) a detecting agent specific for CCL18 protein;
(e) a detecting agent specific for a polynucleotide encoding CCL20; and
(f) a detecting agent specific for CCL20 protein
for detecting an interstitial lung disease or cancer in a sample from a subject.

Preferably, said polynucleotide in (a), (c) and/or (e) is an mRNA. Suitable detecting agents for detecting CCR6 mRNA, CCL18 mRNA or CCL20 mRNA are e.g. antisense oligonucleotide probes specific for CCR6 mRNA, CCL18 mRNA or CCL20 mRNA. A preferred detecting agent for detecting CCR6 receptor, CCL18 protein or CCL20 protein is an antibody or an aptamer. Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')$_2$ fragments. One example of a commercially available antibody specific for CCR6 is the anti-human CCR6 mAb described herein below in example 1. The detecting agent preferably comprises a detectable label.

In one preferred embodiment of the method according to the invention, the diagnostic kit according to the invention, the pharmaceutical composition according to the invention and/or the use according to the invention the interstitial lung disease is selected from the group consisting of diffuse parenchymal lung disease of known cause (preferably collagen vascular disease or environmental or drug related diffuse parenchymal lung disease), granulomatous diffuse parenchymal lung disease (preferably sarcoidosis) and other forms of diffuse parenchymal lung disease (preferably lymphangioleiomyomatosis (LAM), pulmonary Langerhans' cell histiocytosis/histiocytosis X (HX) or eosinophilic pneumonia).

In a particularly preferred embodiment of the method according to the invention, the diagnostic kit according to the invention, the pharmaceutical composition according to the invention and/or the use according to the invention the interstitial lung disease is an idiopathic interstitial pneumonia.

In a further preferred embodiment of the method according to the invention, the diagnostic kit according to the invention, the pharmaceutical composition according to the invention and/or the use according to the invention the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia. In a particularly preferred embodiment of the method according to the invention, the diagnostic kit according to the invention, the pharmaceutical composition according to the invention and/or the use according to the invention the interstitial lung disease is idiopathic pulmonary fibrosis. For an overview on the classification of interstitial lung diseases the skilled person may e.g. refer to American Thoracic Society/European Respiratory Society International Multidisciplinary Consensus Classification of the Idiopathic Interstitial Pneumonias, American Thoracic Society; European Respiratory Society, Am J Respir Crit Care Med. 2002 Jan. 15; 165(2): 277-304.

In some embodiments interstitial lung disease may be caused by a condition selected from the group consisting of scleroderma lung disease, sarcoidosis, hypersensitivity pneumonitis, rheumatoid arthritis, lupus erythematosus and asbestosis.

In another preferred embodiment of the method according to the invention, the diagnostic kit according to the invention, the pharmaceutical composition according to the invention and/or the use according to the invention the cancer is selected from the group consisting of lung cancer, breast cancer, pancreatic cancer, prostate cancer, neuroblastoma, melanoma, brain cancer, kidney cancer, bladder cancer, ovarian cancer, blood cancer and colon cancer. In a further preferred embodiment of the method according to the invention, the diagnostic kit according to the invention, the pharmaceutical composition according to the invention and/or the use according to the invention the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma.

In a particularly preferred embodiment of the method according to the invention, the diagnostic kit according to the invention, the pharmaceutical composition according to the invention and/or the use according to the invention the cancer is lung cancer, most preferably adenocarcinoma of the lung, or pleural mesothelioma. In a most preferred embodiment the cancer is adenocarcinoma of the lung.

The Present Invention Also Relates to (1) A method for identifying a compound capable of inhibiting the activity of the CCR 6 receptor, wherein the method comprises the steps of:
  (a) contacting a CCR6 receptor with a test compound;
  (b) adding a CCR6 receptor agonist, wherein said agonist is a polypeptide comprising or consisting of an amino acid sequence which exhibits at least 80% identity to the sequence according to SEQ ID NO.: 5 or SEQ ID NO.: 18;
  (c) determining the activity of said CCR 6 receptor; and
  (d) selecting said test compound as the compound capable of inhibiting the activity of the CCR 6 receptor if the CCR6 receptor activity determined in (c) is lower than the CCR 6 receptor activity determined in a control.
(2) The method according to (1), wherein said test compound is an antibody, a small molecule or a peptide.
(3) A method for detecting an interstitial lung disease or cancer in a subject comprising the step of determining the level of CCR6 gene expression in a sample from said subject.
(4) The method according to (3), wherein the method further comprises the step of comparing the level of CCR6 gene expression determined in the sample from the subject to the level of CCR6 gene expression in a control, wherein a higher level of CCR6 gene expression determined in the sample from the subject in comparison to the control indicates the presence of an interstitial lung disease or cancer in the subject.
(5) The method according to (3) or (4), wherein the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia.
(6) The method according to (3) or (4), wherein the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma.
(7) A method for quantifying the concentration of a soluble CCR6 receptor polypeptide in a liquid sample from a subject, wherein the method comprises the steps of:
  (a) immobilizing a capture molecule specific for said soluble CCR6 receptor polypeptide on a solid support;
  (b) adding the liquid sample from the subject;
  (c) optionally adding a ligand of said soluble CCR6 receptor polypeptide, wherein said ligand is a polypeptide comprising or consisting of an amino acid sequence which exhibits at least 80% identity to the sequence according to SEQ ID NO.: 18, SEQ ID NO.: 19, SEQ ID NO.: 20 or SEQ ID NO.: 21;
  (d) adding a detecting agent specific for the ligand according to (c), wherein said detecting agent comprises a label;
  (e) quantifying the signal from the detecting agent according to (d).
(8) The method according to (7), wherein said soluble CCR6 receptor polypeptide is the isolated soluble CCR6 receptor polypeptide according to the invention.
(9) A method for detecting and/or prognosticating an interstitial lung disease or cancer in a subject, wherein the method comprises the step of determining the level of soluble CCR6 receptor polypeptide in a sample from said subject.
(10) The method according to (9), wherein the method further comprises the step of comparing the level of soluble CCR6 receptor polypeptide determined in the sample from the subject to the level of soluble CCR6 receptor polypeptide in a control, wherein a lower level of soluble CCR6 receptor polypeptide determined in the sample from the subject in comparison to the control indicates the presence of an interstitial lung disease or a cancer in the subject.
(11) A method according to (9) or (10), wherein the interstitial lung disease is selected from the group consisting of idiopathic pulmonary fibrosis, nonspecific interstitial pneumonia, cryptogenic organizing pneumonia, respiratory bronchiolitis-associated interstitial lung disease, desquamtive interstitial pneumonia, acute interstitial pneumonia and lymphocytic interstitial pneumonia.
(12) A method according to (9) or (10), wherein the cancer is selected from the group consisting of adenocarcinoma, preferably adenocarcinoma of the lung, pleuramesothelioma, colorectal carcinoma, prostate carcinoma, mamma carcinoma, renal cell carcinoma, hepatocellular carcinoma, Non-Hodgkin-Lymphoma and Hodgkin-Lymphoma.

The present invention will now be described with respect to some of its specific examples. These examples are however not to be construed in a limiting way.

EXAMPLES

Example 1—Materials and Methods

Phage Display Library

For the identification of a CCL18-binding motif an established phage-display library was used (1).

Cells and Cell Lines

Fibroblast lines were established either from surgical material from pneum-ectomies or lobe-ectomies from patients suffering from various tumours or from remaining material obtained from fibrotic lungs by video-assisted thoracoscopies (VATS). The patients suffered either from adenocarcinoma of the lung, non-small cell carcinoma or squamous carcinoma. Fibrosis resulted from idiopathic pulmonary fibrosis (UIP), non-specific interstitial pneumonia, sarcoidosis, hypersensitivity pneumonitis, pneumoconiosis or systemic scleroderma. The tissue was cut in small pieces (app. 0.5 cm edge length) and placed in 6-well plates containing 1 ml Quantum 333 (PAA, Pasching, Austria) with 1% penicillin/streptomycin. Outgrowing fibroblasts were harvested when they reached approximately 80% confluence by trypsinisation, cultured in 75 $cm^2$ cell culture flasks (NUNC Thermo Fisher, Roskilde, Denmark) in Quantum 333 and subsequently split (1:3 to 1:5). The established lines were enrolled in the studies from passages 3 to 8.

If not otherwise mentioned cells were stimulated with 10 ng/ml human recombinant CCL18, 2.5 ng/ml TGFβ with or without additional 1 ng/ml TNFα.

AECII were isolated as described previously (2). In brief, macroscopically tumor-free lung tissue was first sliced and slices were washed three times at 4° C. in phosphate-buffered saline (PBS) and then digested in sterile dispase solution (2.5 mg dispase II (Invitrogen GmbH, Karlsruhe, Germany) ml and 50 µg/ml DNase I (Roche Diagnostics, Mannheim, Germany)) at 37° C. for 60 minutes. After dispase digestion, the slices were thoroughly pipetted for several minutes using a 10 ml pipette with a wide inlet. Crude tissue and cell suspensions were filtered through nylon gauze with meshes of 50 and 20 µm. The cell suspension was then layered onto a density gradient solution (PAN Biotech GmbH, Aidenbach, Germany) and centrifuged at 800×g for 20 min.

The cells from interphase were washed and incubated in 100 mm Petri dishes (max. 6×107 cells/dish) in RPMI (Invitrogen, Karlsruhe, Germany) with 10% fetal calf serum (FCS) (PAA Laboratories GmbH, Colbe, Germany) and 1% penicillin/streptomycin (Biochrom AG, Berlin, Germany) at 37° C. in humidified incubator (5% CO2, 37° C.) for 15, 20 and if possible 30 minutes to remove adherent (mostly alveolar macrophages, monocytes and fibroblasts) from non-adherent cells.

Human lung adenocarcinoma cells and pleural mesothelioma cells were a generous gift from Prof. H H Fiebig, Oncotest, Freiburg. The cells were cultured in RPMI1640 containing 10% FCS and 100 U/ml streptomycin and penicillin. Cultures were splitted 1:3 when the cultures reached 90% confluence.

Flow Cytometry

Surface expression of CCR6 of fibroblast and tumor cell lines as well as of RLE-6TN was estimated using a FITC-labelled anti-human CCR6 antibody (R&D Systems, Minneapolis, Minn.) and counted using a FACScalibur (BD, Heidelberg, Germany). Trypsinated cells have to be incubated 3 h in medium at 37° C. to allow re-expression of surface molecules. To inhibit adherence of the cells, this incubation was performed in polypropylene tubes.

CCR6 expression of RLE-6TN was also analysed using a polyclonal goat anti-CCR6 antibody (CKR6/C20, Santa Cruz Biotechnology, Santa Cruz, Calif.) and a FITC labelled mouse-anti-goat antibody (DAKO, Glostrup, Denmark).

Surface expression of CCR6 of tumor cell lines was also estimated using a PE-labelled anti-human CCR6 antibody (R&D Systems, Minneapolis, Minn.) and measured with a FACS Calibur (Beckton Dickinson, Heidelberg, FRG).

Analysis of CCR6 Expression in Human Lung Carcinoma

Freshly isolated tumour tissue from adenocarcinoma of the lung was cut in pieces of not more than 1×1×0.5 cm edge length. The tissue was stabilised using HOPE stabilizing solution (DCS, Hamburg, FRG) at 4° C. and paraffin embedded. Tissue slices were deparaffinized and stained for CCR6 expression by peroxides technique (5) using a commercially available antibody (R&D Systems, Wiesbaden, FRG).

Immunohistochemistry

Immunohistochemistry was performed as described (3,4) using anti-human CCR6 mAb (clone 53103, isotype mouse IgG2b; R&D Systems Europe, UK) and a peroxidase-labeled streptavidin-biotin technique (DAKO LSAB2 System; DakoCytomation, Germany). Counterstain was performed with Mayer's hemalum. For negative control included in every staining series, sections were stained without primary antibody.

FGF2 ELISA

To estimate CCL18-induced FGF2 release fibroblasts were harvested, counted and seeded 300.000 cells per well in a 6-well cell culture plate in Quantum 333. Cells were allowed to attach over night and the medium was replaced with 1 ml of DMEM plus 10% FCS. Cells were either left un-stimulated or were stimulated with 10 ng/ml of human recombinant CCL18. To block CCR6/CCL18 interaction a blocking antibody against CCR6 (R&D systems, Wiesbaden, FRG) or an irrelevant antibody (mouse anti human IgG, R&D Systems) was added to a final concentration of 20 µg/ml in parallel cultures. After 24 h of culture the supernatant was harvested and stored at −80° C. until FGF2 determination.

FGF2 concentrations were measured using an ELISA development kit (R&D) and performed as suggested by the supplier.

Real-Time PCR

After the indicated culture period total RNA was extracted using TRIzol Reagent according to the manufacturer's protocol (Invitrogen, Karlsruhe, Germany). Total RNA was reverse-transcribed with StrataScript RT (Stratagene, Santa Clara, Calif.) using oligo (dT)12-18 primer to produce cDNA according to the manufacturer's protocol. Specific primers for human CCR6, collagen type I, alpha-smooth muscle actin and GAPDH were designed using Primer3 software (Whitehead Institute for Biomedical Research, Cambridge, USA; http://frodo.wi.mit.edu/cgi-bin/primer3/primer3_www.cgi), Amplify1.2 software (University of Wisconsin, USA; http://engels.genetics.wisc.edu/amplify) using LocusLink and GenBank databases (National Center for Biotechnology Information; http://www.ncbi.nlm.nih.gov/LocusLink/index.html). Accession code numbers for the nucleotide sequences used to generate the respective primers and the primer sequences are depicted in FIG. 17.

All primers were intron-spanning and synthesized by MWG-Biotech (MWG-Biotech AG, Germany). Real time PCR was performed with the iQ SYBR Green SuperMix, iCycler thermocycler, and iCycler iQ 3.0 software (Bio-Rad Laboratories GmbH, Germany) according to the manufacturer's protocol. To control for specificity of the amplification products, a melting curve analysis was performed. No amplification of nonspecific products was observed in any of the reactions. A threshold cycle value (Ct) was calculated and used to compute the relative level of specific mRNA by the following formula: "relative expression= $2^{(Ct\ GAPDH-Ct\ CCL18)} \times 10{,}000$" for each cDNA sample.

Western Blot

After the indicated culture period the cells were washed once in PBS and lysed in ice cold lysis buffer. Whole cell lysates were boiled at 93° C. for 5 minutes in equal volumes of loading buffer (0.5M Tris-HCl pH 6.8, 2% SDS, 0, 05% bromphenolblue, 20% 2-mercaptoethanol, 10% Glycerol).

All samples were subjected to 12% sodium dodecylsulfate-PAGE, separated by electrophoresis and transferred to a polyvinylidene difluoride membrane (PVDF). After blocking for 2 h in Tris-buffered saline (TBS) containing 5% non-fat dry milk, the membranes were incubated with primary antibody (rabbit-anti-collagen I (Rockland, Gilbertsville Pa.); anti αSMA (rabbit-anti-aSMA (Abcam, Cambridge, Mass.); anti vimentin (Santa Cruz); anti CCR6: CKR6/C20, Santa Cruz) diluted 1:700 with TBS at 4° C. overnight. Visualization was performed using appropriate secondary antibodies labeled with IRDye 800CW or IRDye 700CW (Li-COR Bioscience, Bad Homburg, Germany) diluted 1:10 000-1:20000 for 2 h and scanned using Odyssey system (Li-COR Biosience) according to the manufactures instructions.

Analysis of CCR6 Expression by PBMNCs in Presence or Absence of PHA

Human peripheral blood mononuclear cells were isolated from venous puncture blood by density centrifugation, washed and counted. Cells were adjusted to $1 \times 10^6$ cells per ml in complete culture medium (RPMI1640 with 10% foetal calf serum and 100 U penicillin/streptomycin) and cultured for 24 h either in the absence or presence of 10 µg/ml phytohemeagglutinin (PHA). The percentage of CCR6-positive cells was measured using FITC-labelled anti-CCR6 antibodies (R&D Systems, Wiesbaden FRG) and counted in an FACS calibur (Becton Dickinson, Heidelberg, FRG).

Inhibition of CCR6 Down-Regulation

Freshly isolated mononuclear cells were incubated for 20 minutes with 10 ng/ml of CCL18, 100 ng/ml of the inhibitor peptide PS-AU-105 (polypeptide according to SEQ ID NO.: 9), a combination of both or were left untreated. The incubation was performed in RPMI1640 with 10% fetal calf serum and 100 U/ml Streptomycin/Penicillin at 37° C. After the incubation, the cells were centrifugated and the supernatant was discarded. The cells were fixed with 4% paraformaldehyde for 5 minutes on ice and washed twice in PBS containing 1% FCS. After fixation the cells were stained using a fluorescein-conjugated antibody against CCR6 (R&D systems, Wiesbaden, FRG) and analyzed by flow cytometry (FACScalibur and Quantiquest; both Becton Dickinson, Franklin Lakes, USA).

Statistics (FIGS. 1 to 16)

All statistics were performed using nonparametric statistics. Pair wise analysis of increase or inhibition was carried out using Wilcoxon-signed rank analysis; unpaired groups were analysed using Mann-Whitney U Test. Values of p<0.05 were considered significant. Data are presented using Box-Plots. In this case median is given as line in a rectangular indicating the 25 and 75 percentile. The 5 and 95 percentile are indicated as lines beneath or above the rectangular, values beyond or above the 5 and 95 percentile are illustrated as dot.

Patients

Sera were collected from healthy volunteers (n=6), patients suffering from NSIP (n=6) and UIP (n=13) by venipuncture. After one hour of clotting, the blood was centrifuged for 15 minutes and the serum samples were aliquoted and stored at −80° C. before ELISA.

Western Blot Analysis of Sera (Example 8)

Serum was diluted 1:10 with Western Blot buffer and boiled at 93° C. for 5 minutes in equal volumes of loading buffer (0.5M Tris-HCl pH 6.8, 2% SDS, 0, 05% bromphenolblue, 20% 2-mercaptoethanol, 10% Glycerol).

The samples were subjected to 12% sodium dodecyl sulfate polyacrylamide gel electrophoresis (SDS-PAGE), separated by electrophoresis and transferred to a polyvinylidene difluoride membrane (PVDF). After blocking for 2 h in Tris-buffered saline (TBS) containing 5% non-fat dry milk, the membranes were incubated with primary anti-CCR6 antibody (CKR6/C20, Santa Cruz) diluted 1:700 with TBS at 4° C. overnight. Visualization was performed using a secondary antibody labeled with IRDye 800CW (Li-COR Bioscience, Bad Homburg, Germany) diluted 1:10 000-1:20000 for 2 h. The blots were then scanned and evaluated using Odyssey system and software (Li-COR Biosience) according to the manufactures instructions.

CCR6 ELISA

The Elisa was performed as suggested by the supplier (Uscn Life Science Inc. Wuhan, China).

Blocking of Free Soluble CCR6

Sera were diluted with an equal volume of PBS/BSA (1% bovine serum albumin, Sigma, Deisenhofen, Germany) either without any additives or containing CCL18 or CCL20 (both PeproTech, Hamburg, Germany; 100 ng/ml each). The diluted sera were then incubated for 1 h at 37° C. and subsequently measured by ELISA.

Bronchoalveolar Lavage

Bronchoscopy, Bronchoalveolar lavage and BAL-cell culture was performed using a standard technique as previously described (8, 9) At the end of the culture period supernatants were harvested and stored at −70° C. until assayed for CCL18 concentrations. The viability of the cells was determined by Trypan blue exclusion and always exceeded 95%.

BAL Cell Differential Count

Cells differential were determined by counting at least 200 cells at a cell smear stained by May-Grunwald Staining.

For immunoperoxidase staining, cells were fixed on poly-L-lysine-coated slides (Bio-Rad, Munich, Germany) and developed with a peroxidase-antiperoxidase (PAP) technique, using monoclonal antibodies against CD4, CD8, IL-2R (Ortho Diagnostic Systems; Neckargemünd, Germany) and human leukocyte antigen-DR (HLA-DR) (Becton Dickinson, Heidelberg, Germany). At least 200 cells were counted and positive cells are expressed as percentage of all lymphocytes.

Statistics (FIGS. 18 to 22)

Data are depicted in mean±SD. Comparisons of nominal data are performed using Chi-square test. Continuous data are analysed using non-parametrical Mann-Whitney U test. All statistics were performed using StatView.

Material and Methods Relating to Examples 11 to 17 and FIGS. 23 to 32:

Characteristics of NSCLC Patients and Healthy Controls:

One hundred and seventy patients diagnosed with NSCLC (UICC Stage I to Stage W, $6^{th}$ Edition) and a control group of 31 healthy volunteers are included in this study. Mean age of the patients was 64±10 years, 125 male and 45 female. Adenocarcinoma was diagnosed in 70 patients, 54 patients presented with squamous carcinoma and in 46 cases the examining pathologist described a mixed histology. According to the UICC staging classification ($6^{th}$ Edition)

we found 22 patients in stage IA, 19 in stage IB, 5 in stage IIB, 29 in IIIA, 25 in IIIB and 69 in stage IV. In one case the UICC stage was not determined because of insufficient data recordings, which described only the nodal state. The control group consisted of 10 female and 22 male subjects with a mean age of 32±11 years.

All procedures for informed consent, data collection and privacy protection were approved by the ethic boards of the University Medical Center Freiburg. Clinical data were extracted from the medical record databank of the University Medical Center Freiburg. Serum samples from each individual were obtained at the time of diagnosis during their clinical work-out before any therapeutic treatment was started. Sera were stored at −80° C. until analysis was performed. The diagnosis of NSCLC was confirmed by histology or cytology. Histological type was determined according to the World Health Organization classification. All tumors were classified according to the UICC 6th Edition.

Immunodetection of Serum CCL18

Venous blood was sampled using a routine procedure. Blood samples rested 20 minutes before centrifugation. After centrifugation, serum samples were frozen at −80° C. and stored. CCL18 was quantified using DuoSet ELISA Development System Kit (R&D Systems Europe, Wiesbaden, Germany). The detection limit for CCL18 ELISA was 7 pg/ml. All samples were measured in duplicate. For duplicate samples, intra-assay coefficients of variation of 10% and inter-assay coefficients of variation of 20% were accepted.

EMT Induction by CCL18

Cells of the adenocarcinoma cell line A549 were seeded in 6-well plates and allowed to adhere over night. After adherence the cells were stimulated with the indicated amount of CCL18. TGFβ was used as a positive control. The cells were harvested after 72 h and analyzed either by PCR or by western blot.

Isolation of Fibroblast Lines

Fibroblast lines were established from surgical material from pneum-ectomies or lobe-ectomies from patients suffering from various tumours. The tissue was cut in small pieces (app. 0.5 cm edge length) and placed in 6-well plates containing 1 ml Quantum 333 (PAA, Pasching, Austria) with 1% penicillin/streptomycin. Outgrowing fibroblasts were harvested when they reached approximately 80% confluence by trypsinisation, cultured in 75 cm$^2$ cell culture flasks (NUNC Thermo Fisher, Roskilde, Denmark) in Quantum 333 and subsequently split (1:3 to 1:5).

Flow Cytometry

Surface expression of CCR6 of fibroblast lines was estimated using an FITC-labelled anti-human CCR6 antibody (R&D Systems, Minneapolis, Minn.) and measured by cytometry (FACScalibur, Becton Dickinson, Franklin Lakes, USA).

Statistics

Concentrations are given as median (range). Statistical analysis was performed using StatView 5.0 software (SAS Institute, NC). Data are presented as mean with standard derivation and shown as box plots. Comparisons between patient groups were performed using ANOVA and Bonferroni-Dunn Test for multiple comparisons. Linked variables like cytokine production of identical cell-cultures after different stimulations were compared by Wilcoxon Signed Rank Test. ROC analysis and "plots versus criterion value" were performed using MedCalc (MedCalc Software bvba, Mariakerke, Belgium).

In single comparisons probability values were considered significant if they were less than 0.05. In multiple comparisons levels for p were adjusted for the number of comparisons (Bonferroni).

Example 2—Identification of a CCL18-Binding Peptide Using Phage Display

After 3 circles of binding of the phages of the phage library (as described in Example 1) to plate-bound human CCL18, phage-infected E. coli were plated on agar and 20 colonies were picked, expanded and DNA was isolated for sequencing. Some of the sequences were not informative or coded for non-human gene targets, however, one sequence with a clear relation to the CC-chemokine receptor 6 (CCR6) was identified.

Example 3—Analysis of CCR6 Expression on Primary Human Fibroblast Line

PCR

Expression studies using primers for CCR6 revealed a high variability of CCR6 mRNA expression. Highest expression was found in fibroblast lines derived from lung of patients suffering from usual interstial pneumonia (UIP). Lines derived from patients suffering from non-specific interstitial pneumonia (NSIP) or squamous carcinoma expressed only marginal levels of CCR6 mRNA (FIG. 1).

FACS

Flow-cytometric analyses of the established fibroblast lines revealed detectable CCR6 expression only on fibroblast lines derived from patients suffering from UIP. Lines generated from lungs of patients suffering from squamous carcinoma or NSIP do not express detectable CCR6 on their surface (FIG. 2). Increased CCR6 expression of fibroblasts from fibrotic lungs remained increased throughout all passages (data not shown).

Immunohistochemistry

Immunohistochemical studies on tissue sections taken from lungs of patients with IPF/UIP did not reveal CCR6 expression in normal lung tissue (FIG. 3A). In fibrotic lungs CCR6 expression was detected on the apical surface of alveolar epithelial cells (FIG. 3B) and on fibroblasts (FIG. 3C).

Example 4—Functional Analysis of CCR6

FGF2 Expression

Fibroblasts derived from non-fibrotic lungs released only marginal levels of FGF2. CCL18 stimulates FGF2 release in these cells only marginally. In contrast, non-stimulated fibroblasts derived from fibrotic lungs release increased levels of FGF2 ($p<0.005$ compared with controls) which is further up-regulated by CCL18 ($p<0.05$, FIG. 4).

Blockade of CCR6 by a blocking antibody exerts no effect on CCL18 stimulated FGF2 release by non-fibrotic fibroblast lines. In fibroblasts derived from fibrotic lungs blockade of CCR6 significantly diminished CCL18 induced FGF2 up-regulation ($p<0.05$).

Collagen Expression

CCL18 has been reported to induce the expression of collagen and αSMA (7, 18). It was thus determined whether the induction of these molecules is also CCR6 dependent. As shown in FIG. 5 (upper panel) CCL18 up-regulates collagen I expression in three of four cell lines analysed. This induction was inhibited in all three CCL18 reactive cell lines by the blockade of CCR6 using a blocking antibody. The same result was received for the CCL18 induced up-regulation of αSMA. The same cell line which failed to increase collagen I expression by CCL18 stimulation did also not react in case of αSMA (FIG. 5, lower panel).

Example 5—Induction of Epithelial-Mesenchymal-Transition (EMT) to Myo-Fibroblasts by CCL18 is CCR6-Dependent EMT of the Rat Alveolar Epithelial Cell Line RLE-6TN The rat alveolar epithelial cell line RLE-6TN discloses the typical cuboid cell form of epithelial cell (FIG. 6 top). Culture of these cells for six days in the presence of CCL18 induces a differentiation into spindle-shaped, fibroblast-like cells (FIG. 6 mid, see arrows) in some areas. This differentiation is more pronounced in the presence of TGFβ (FIG. 6 bottom, see arrows) as almost all cells disclose a spindle-shaped, fibroblast-like phenotype. This indicates that CCL18 induce at least partially EMT in RLE-6TN cells.

Western Blot analyses of RLE-6TN after EMT induced either by CCL18 or TGFβ revealed expression of vimentin after culture in the presence of CCL18 which is enhanced by TNFα (FIG. 7). Only a faint expression of αSMA was visible in both conditions. TGFβ induced a strong expression of αSMA but failed to induce the expression of vimentin.

Fluorescence microscopy demonstrated that stimulation with TGFβ indeed induces αSMA expression in RLE-6TN cells (FIG. 8B) whereas CCL18 or CCL18/TNFα did not (FIGS. 8C and D). In contrast, all stimulations induced the expression of CD90 (FIGS. 9B and C) although CD90 expression was more intense using CCL18. Quantitative real-time PCR of RLE-6TN revealed a faint expression of rat CCR6. However, CCR6 protein analysis using Western Blot or flow cytometry could not demonstrate the expression of CCR6 by RLE-6TN (data not shown). The cells were therefore transiently transfected with a commercially available plasmid containing a DNA sequence coding for human CCR6. After transfection, stimulation with CCL18 induced αSMA in CCR6 transfected cells, but not in mock transfected cells. In contrast, TGFβ induced αSMA expression in both cell types (FIG. 10).

EMT of Human Primary Alveolar Epithelial Cells

Stimulation of isolated human primary alveolar epithelial cells type II stimulated with either TGFβ+TNFα or CCL18 with or without TNFα also induces EMT as demonstrated by the induction of vimentin and αSMA expression and the reduced expression of cytokeratin (FIG. 11).

Example 6—Inhibition of CCL18-Induced Down Regulation of CCR6 Expression on PBMNCs Isolated human peripheral blood mononuclear cells (PB-MNC) were grouped according to their basal percentage of CCR6+ cells. Culture of PBMNC without any activation does not alter the percentage of CCR6+ cells. In contrast, activation with PHA increases CCR6+ percentage in preparations with low initial CCR6+ proportion (FIG. 12 shaded bars), but decreases it in preparations with high CCR6+ proportion (FIG. 12 white bars).

Incubation of isolated, CCR6+ rich PBMNCs with CCL18 for 20 minutes resulted in a decrease in the percentage of CCR6+ cells (FIG. 13) possibly due to internalization of the CCR6 receptor. This CCL18 induced reduction of CCR6 expression is diminished in the presence of the inhibitor peptide PS-AU-105 (polypeptide according to SEQ ID No.: 9). FIG. 14 demonstrates a clear sub-population of CCR6+ cells in non-stimulated (pos. control) culture. Stimulation with CCL18 diminishes this subpopulation as demonstrated by a lowered second peak (CCL18 only). CCL18 stimulation in the presences of the inhibitor peptide PS-AU-105 (polypeptide according to SEQ ID No.: 9) fails to down-regulate the CCR6+ sub-population. The inhibitor alone exhibits no effect (inhibitor only).

Example 7—Analysis of CCR6 Expression in Human Lung Carcinoma

Immunohistochemistry

Analysis of control lung revealed no CCR6 staining (FIG. 15A). In contrast, tumour cells disclosed a clear CCR6 expression (FIGS. 15 B and C, arrows). In addition, some fibroblast also disclosed a faint CCR6 expression (FIG. 15 C, arrow heads).

FACS

FACS analysis revealed a clear cut CCR6 expression in two out of three adenocarcinoma cell lines (FIG. 16 upper panel) and all pleural mesothelioma cell lines (FIG. 16 lower panel). The lung adenocarcinoma cell line LxFA 526L discloses marginal CCR6 expression.

Example 8—Detection of Soluble CCR6 (sCCR6) in Serum from Patients Suffering from Pulmonary Fibrosis and in Serum from Healthy Controls Western Blot Analysis Western Blot analysis revealed that sCCR6 is present in serum from healthy volunteers and UIP patients (FIG. 18A). Quantitative analysis of the western blots revealed slightly but nevertheless significantly reduced peak intensity for fibrotic patients compared with controls (FIG. 18B).

ELISA

In order to assess the differences observed in Western Blot analysis more precisely, the concentration of sCCR6 was measured using a commercially available CCR6 ELISA. In 15 out of 19 samples from fibrosis patients (NSIP: n=6, UIP: n=13) no sCCR6 could be detected, but only 2 out of 9 serum samples from healthy volunteers were found to be negative ($p<0.005$). Even in two samples which were shown to be positive by Western Blot (lanes 4 and 6 of FIG. 18 A) no sCCR6 was detectable by ELISA. In sera from patients suffering from pulmonary fibrosis concentrations of sCCR6 was significantly lower compared with controls (18±11 versus 216±95 pg/ml; $p<0.001$; FIG. 19). Further analysis of the underlying fibrotic diseases did not reveal differences between the sCCR6 concentrations in sera from UIP or NSIP patients.

Example 9—sCCR6 Molecules in Sera from Fibrotic Patients are Ligand-Bound

The sCCR6 ELISA described in Example 8 uses a monoclonal anti-CCR6 antibody as a capture antibody bound at the plate and a biotin-conjugated polyclonal anti-CCR6 antibody as a detection antibody. Most of the monoclonal anti CCR6 antibodies are directed against the N-terminal part of the receptor bearing the ligand binding site. In order to test whether the antibody recognition site of the sCCR6 molecule in sera from fibrotic patients might be covered with the ligand because of the high abundance of CCL18 in these sera [6, 7], sera from healthy volunteers were incubated with 100 ng/ml of CCL18 or CCL20, respectively and sCCR6 was measured in blocked and unblocked sera by ELISA. Addition of these CCR6 ligands leads to a marked reduction of the sCCR6 signal (FIG. 20). The addition of 100 ng of CCL18 or CCL20 nearly abolishes CCR6 detection in sera with low and medium sCCR6 concentrations. In a serum with a high sCCR6 concentration a reduction of only 36% was seen in case of CCL18 and 14% in case of CCL20.

Thus, sCCR6 bound to its ligands CCL18 and CCL20 is no longer detected by ELISA.

These results indicate that the sCCR6 molecules in sera from fibrotic patients are ligand-bound, such that lower concentrations of sCCR6 are detected in sera from said patients by ELISA (Example 8). The data also indicate that the CCL18-blocking capacity is exhausted in patients negative for ligand-free sCCR6 in serum.

Example 10—Fibrosis Patients Positive for sCCR6 in Serum Disclose a Higher Percentage of Lymphocytes in Bronchoalveolar Lavage Fluid (BAL) Compared with sCCR6 Negative Patients CCL18, which was identified by the inventors of the present invention as a ligand of the CCR6 receptor, has been reported to induce T cell chemotaxis. Therefore, a possible influence of sCCR6 on the cell population in bronchoalveolar lavage fluid (BAL) was tested. Indeed, fibrosis patients (NSIP: n=6, UIP: n=13) positive for ligand-free sCCR6 in serum disclose a significantly higher percentage of lymphocytes in BAL compared with patients negative for ligand-free sCCR6 in serum (35.5% versus 17.8%, p<0.05). This difference was not seen in controls (FIG. 21).

These data indicate that sCCR6 diminishes the bioavailability of CCL18 in the serum, thus increasing the CCL18 concentration gradient between lung and periphery and forcing the chemotaxis of immune cells into the alveoli of the lung. This function is exhausted in those patients found to be negative for ligand-free sCCR6 leading to an accumulation of CCL18 and decreasing a functional CCL18 concentration gradient.

In general, pulmonary fibrosis in patients with increased percentages of lymphocytes is less severe compared with patients with low percentages of lymphocytes in BAL. Analysing lymphocyte sub-populations revealed a slight but significant increase in $CD3^+$ T cells in patients positive for sCCR6 in serum (91.0±1.4% versus 95.7±1.2%; p<0.05). In contrast, the percentage of HLA-DR positive lymphocytes was lower in sCCR6 positive patients compared with sCCR6 negative patients (32.3±14.4% versus 7.0±7.8%; p<0.05). sCCR6 positive patients also disclosed increased percentages of NK cells ($CD57^+$) and CD1a positive cells (33.0±9.6% versus 14.5±5.6% and 1.0±1.0% versus 0.1±0.3%, respectively; p<0.05 in both cases) (FIG. 22).

Example 11—Serum Levels of CCL18 in the Patients with NSCLC and their Correlation with Clinicopathological Parameters There was a significant difference of all patient groups compared with controls (p<0.0001; FIG. 23). The CCL18 serum level in patients with squamous cell carcinoma was higher as in sera from patients with adenocarcinoma (172±95 ng/ml, 207±139 ng/ml; respectively; p<0.02). CCL18 serum levels increased gradually and significantly with the progress of the T stage (FIG. 24). Compared with controls CCL18 serum level was significantly higher in Stage I (134±74 ng/ml, n=39, p=0.0002) and more so in stage II patients (176±99 ng/ml, n=61 p<0.0001), III (215±106 ng/ml, n=26 p<0.0001) and IV (219±177 ng/ml, n=28 p<0.0001). Comparisons between the tumor patients revealed that levels in stage I were significantly lower as compared with stage III (215±106 ng/ml, n=26, p<0.005) and stage IV (219±177 ng/ml, n=28, p=0.002). CCL18 level in stage III and IV differed also significantly with controls (p<0.0001).

Example 12—Determination of CCL18 Serum Level Cut-Off Points

Receiver operating characteristic (ROC) analyses revealed a cutoff point of 83 ng/ml (area under the curve (AUC): 0.968; p<0.0001, FIG. 25 left) to discriminate between healthy controls and NSCLC patients. ROC analyses to discriminate between cancer related or non-cancer related death did not lead to a valid AUC. To stratify the tumor patients, a criterion value plot was performed using the criterion death within observation period. This analysis revealed a point of equal sensitivity and specificity (54%) of 162 ng/ml (FIG. 25 right).

Example 13—CCL18 Serum Level and Survival in NSCLC Patients

Patients with NSCLC and CCL18 serum level higher than 160 ng/ml had a mean survival time of 623 days, whereas patients with NSCLC and a serum level between 160 ng/ml and 80 ng/ml had a mean survival time of 984 days. In patients with CCL18 level below 80 ng/ml the mean survival time was 841 days (p<0.004, FIG. 26).

Example 14—CCL18 Serum Level and Survival by Histological Subgroups

In patients with an adenocarcinoma of the lung a mean survival time of 388 days was found in the group with the highest CCL18 level. In the group with a CCL18 level between 160 and 80 ng/ml the mean survival time was 788 days and in the group with the normal CCL18 level the mean survival time was 1152 days (p<0.002).

Example 15—CCL18 Serum Level and Tumor Stages in Histological Subgroups

Regarding the subgroup of adenocarcinoma patients the mean N-stages in the group with serum CCL18 concentrations above 160 ng/ml were significantly higher (1.7±1.1) as compared with the subgroup with normal serum CCL18 levels (0.5±1; p<0.005, FIG. 28). Regarding the patients with adenocarcinoma, there was also a trend to a higher frequency of metastases in the subgroup with serum CCL18 above 160 ng (58%) which was lower in the other groups (<160 ng/ml: 42%; normal: 25%).

Example 16—CCL18 Induces EMT in Adenocarcinoma Cells

Stimulation of adenocarcinoma cells with CCL18 for 72 h induces a marked and dose dependent up-regulation of mRNA expression of the fibroblast marker FSP1. The up-regulation induced by CCL18 was higher as the up-regulation induced by TGFβ (FIG. 29). In addition, CCL18 also induces dose-dependently the expression of the fibroblast-associated transcription factor snail. Again, stimulation with CCL18 was more effective as TGFβ (FIG. 30). In contrast to the markers named above, the epithelial marker E-cadherin was substantially down-regulated after 24 h of stimulation with CCL18 (FIG. 31).

Example 17—CCR6 Expression in Fibroblast Lines from Histological Subgroups

Fibroblasts isolated from lungs from patients suffering from adenocarcinoma disclose a higher percentage of CCR6 positive cells (30±22%, n=4; FIG. 32) as compared with fibroblast lines derived from squamous carcinoma or lungs with mixed histology (2±1%, n=8 and 2±2%, n=6, respectively).

The results described in Examples 11 to 17 represent the first study investigating CCL18 serum levels in patients with lung cancer. It was observed that the mean serum level of CCL18 in patients with lung cancer is more than four fold increased compared with healthy controls. The data obtained demonstrate that CCL18 serum level rises corresponding to the T-stage. In contrast, N- and M-stage did not correlate with CCL18 serum level. In addition, CCL18 serum levels differed according to the different histology of lung cancer.

Tumor associated macrophages (TAM) resemble alternatively activated macrophages including the release of CCL18.

The cut-off point to discriminate between healthy subjects and patients with NSCLC is 83 ng/ml and is in the same range as the cut-off point determined by the inventors used to discriminate between fibrosis and healthy control. Using ROC analysis it was not possible to predict the cancer related death according to the CCL18 serum level. Thus, to define a cut-off value to stratify the patients a criterion value plot for survival was performed. This CCL18 criterion value plot revealed a concentration of 160 ng/ml as cut-off point. This cut-off point 160 ng/ml predicted strongly the mean survival time in patients with NSCLC. Patients with a CCL18 serum concentration of 160 ng/ml or above had a one-third shorter mean survival time than patients with a CCL18 concentration less than 160 ng/ml. This effect is most distinctive in the subgroup of patients with adenocarcinoma. CCL18 is a typical product of alternatively activated macrophages and is a possible marker of TAMs. Because TAMs are located within the tumor, their number should increase with the tumor mass. The correlation between the CCL18 serum level and the T-stage as a surrogate marker for tumor size was thus analyzed. This applies in particular in the lower T-stages and indeed the CCL18 serum level increases with increasing T-stages from T1 to T3. The main difference between the T3 and T4 stage is the infiltration of important mediastinal structures but does not necessarily reflect an increase in size. No remarkable difference was found in CCL18 serum level of patients with T3 and T4 stage.

N- and M-stages are surrogate markers for hematogenous and lymphogenous metastasis. The increase in the N-stages and the trend towards a higher frequency of metastases in patients with high levels of serum CCL18 again indicates that CCL18 is a marker of an extended disease in adenocarcinoma.

In parallel to the results obtained with epithelial cells, CCL18 induces epithelial-mesenchymal transition also in adenocarcinoma cells. EMT is thought to be an important event in the metastatic processes. Cancer cells do have only a limited migratory capacity. During EMT cancer cells lose their contact to the surrounding tissue and gain functions which enables the cell to migrate. The up-regulation of the mesenchymal markers FSP1 and snail and the down-regulation of E-cadherin indicate that CCL18 induces EMT in adenocarcinoma cells. The loss of the adhesion molecule E-cadherin thereby enables the cell to escape from the tumor tissue. FSP1 is thought to be related to metastasis and tumor invasion. The transcription factor snail regulates the expression of collagen, some matrix metalloproteinases and α-smooth muscle actin, which is important for the motility of the cells.

Thus, CCL18 is a biomarker to stratify adenocarcinoma patients at high risk. The data also indicate that CCL18 promotes tumor metastasis by the induction of EMT.

LITERATURE

1. Trepel, M., Arap, W., and Pasqualini, R. 2002. In vivo phage display and vascular heterogeneity: implications for targeted medicine. *Curr Opin Chem Biol* 6:399-404.
2. Pechkovsky, D. V., Zissel, G., Ziegenhagen, M. W., Einhaus, M., Taube, C., Rabe, K. F., Magnussen, H., Papadopoulos, T., Schlaak, M., and Muller-Quernheim, J. 2000. Effect of proinflammatory cytokines on interleukin-8 mRNA expression and protein production by isolated human alveolar epithelial cells type II in primary culture. *Eur Cytokine Netw* 11:618-625.
3. Goldmann, T., Wiedorn, K. H., Kuhl, H., Olert, J., Branscheid, D., Pechkovsky, D., Zissel, G., Galle, J., Muller-Quernheim, J., and Vollmer, E. 2002. Assessment of transcriptional gene activity in situ by application of HOPE-fixed, paraffin-embedded tissues. *Pathol Res Pract* 198:91-95.
4. Pechkovsky, D. V., Zissel, G., Goldmann, T., Einhaus, M., Taube, C., Magnussen, H., Schlaak, M., and Muller-Quernheim, J. 2002. Pattern of NOS2 and NOS3 mRNA expression in human A549 cells and primary cultured AEC II. *Am J Physiol Lung Cell Mol Physiol* 282:L684-692.
5. Droemann, D., D. Albrecht, J. Gerdes, A. J. Ulmer, D. Branscheid, E. Vollmer, K. Dalhoff, P. Zabel, and T. Goldmann, *Human lung cancer cells express functionally active Toll-like receptor 9*. Respir Res, 2005. 6(1): p. 1.
6. Prasse, A., D. V. Pechkovsky, G. B. Toews, M. Schafer, S. Eggeling, C. Ludwig, M. Germann, F. Kollert, G. Zissel, and J. Muller-Quernheim, *CCL18 as an indicator of pulmonary fibrotic activity in idiopathic interstitial pneumonias and systemic sclerosis*. Arthritis Rheum, 2007. 56(5): p. 1685-93.
7. Prasse, A., C. Probst, E. Bargagli, G. Zissel, G. B. Toews, K. R. Flaherty, M. Olschewski, P. Rottoli, and J. Muller-Quernheim, Serum CC-Chemokine Ligand 18 Concentration Predicts Outcome in Idiopathic Pulmonary Fibrosis. Am J Respir Crit Care Med, 2009. 179(8): p. 717-723.
8. Ziegenhagen M W, Zabel P, Zissel G, Schlaak M, Müller-Quernheim J. Serum level of interleukin 8 is elevated in idiopathic pulmonary fibrosis and indicates disease activity. Am J Respir Crit Care Med 1998; 157:762-768.
9. Prasse A, Georges C G, Biller H, Hamm H, Matthys H, Luttmann W, Virchow J C Jr. Th1 cytokine pattern in sarcoidosis is expressed by bronchoalveolar CD4+ and CD8+ T cells. Clin Exp Immunol 2000; 122:241-8.

The invention claimed is:

1. A method of treating an interstitial lung disease in a subject, comprising administering to the subject an effective amount of an isolated soluble CCR6 receptor polypeptide comprising the amino acid sequence of SEQ ID NO: 1.

2. The method of claim 1, wherein the isolated soluble CCR6 receptor polypeptide consists of the amino acid sequence of SEQ ID NO: 1.

3. The method of claim 1, wherein the isolated soluble CCR6 receptor polypeptide binds to CCL18 and/or CCL20.

* * * * *

SEQUENCE LISTING

<160> NUMBER OF SEQ ID NOS: 27

<210> SEQ ID NO 1
<211> LENGTH: 48
<212> TYPE: PRT
<213> ORGANISM: Artificial Sequence
<220> FEATURE:
<223> OTHER INFORMATION: N-terminal domain of human CCR6 receptor

<400> SEQUENCE: 1

```
Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45
```

<210> SEQ ID NO 2
<211> LENGTH: 19
<212> TYPE: PRT
<213> ORGANISM: Artificial Sequence
<220> FEATURE:
<223> OTHER INFORMATION: first extracellular loop of human CCR6 receptor

<400> SEQUENCE: 2

```
Ser His Ala Thr Gly Ala Trp Val Phe Ser Asn Ala Thr Cys Lys Leu
1               5                   10                  15

Leu Lys Gly
```

<210> SEQ ID NO 3
<211> LENGTH: 3216
<212> TYPE: DNA
<213> ORGANISM: Homo sapiens

<400> SEQUENCE: 3

```
agtgtatggg tgaaggaggc agcagtgtgg ccggagagga gagctgggct gggagcacag      60
gaaggtcccc aggactctgt ggtcatcagt aagagagggc ccacgtgtat atgctggtga     120
acagaaatgt caacctttc aaagtctgac atttaagaga aaaaactgtg gctgttggtt      180
tgtggaacag acagctcctt ctttattgag tcacctctac tttcctgcta ccgctgcctg    240
tgagctgaag gggctgaacc atacactcct ttttctacaa ccagcttgca ttttttctgc    300
ccacaatgag cggggaatca atgaatttca gcgatgtttt cgactccagt gaagattatt    360
ttgtgtcagt caatacttca tattactcag ttgattctga gatgttactg tgctccttgc    420
aggaggtcag gcagttctcc aggctatttg taccgattgc ctactccttg atctgtgtct    480
ttggcctcct ggggaatatt ctggtggtga tcacctttgc tttttataag aaggccaggt    540
ctatgacaga cgtctatctc ttgaacatgg ccattgcaga catcctcttt gttcttactc    600
tcccattctg ggcagtgagt catgccaccg gtgcgtgggt tttcagcaat gccacgtgca    660
agttgctaaa aggcatctat gccatcaact ttaactgcgg gatgctgctc ctgacttgca    720
ttagcatgga ccgtacatc gccattgtac aggcgactaa gtcattccgg ctccgatcca    780
gaacactacc gcgcagcaaa atcatctgcc ttgttgtgtg gggctgtca gtcatcatct    840 ccagctcaac ttttgtcttc aaccaaaaat acaacaccca aggcagcgat gtctgtgaac    900
ccaagtacca gactgtctcg gagcccatca ggtggaagct gctgatgttg gggcttgagc    960
tactctttgg tttctttatc cctttgatgt tcatgatatt tgttacacg ttcattgtca    1020 aaaccttggt gcaagctcag aattctaaaa ggcacaaagc catccgtgta atcatagctg   1080
```

```
tggtgcttgt gtttctggct tgtcagattc ctcataacat ggtcctgctt gtgacggctg    1140
caaatttggg taaaatgaac cgatcctgcc agagcgaaaa gctaattggc tatacgaaaa    1200
ctgtcacaga agtcctggct ttcctgcact gctgcctgaa ccctgtgctc tacgctttta    1260
ttgggcagaa gttcagaaac tactttctga agatcttgaa ggacctgtgg tgtgtgagaa    1320
ggaagtacaa gtcctcaggc ttctcctgtg ccgggaggta ctcagaaaac atttctcggc    1380
agaccagtga gaccgcagat aacgacaatg cgtcgtcctt cactatgtga tagaaagctg    1440
agtctcccta aggcatgtgt gaaacatact catagatgtt atgcaaaaaa aagtctatgg    1500
ccaggtatgc atggaaaatg tgggaattaa gcaaaatcaa gcaagcctct ctcctgcggg    1560
acttaacgtg ctcatgggct gtgtgatctc ttcagggtgg ggtggtctct gataggtagc    1620
attttccagc actttgcaag gaatgttttg tagctctagg gtatatatcc gcctggcatt    1680
tcacaaaaca gcctttggga aatgctgaat taaagtgaat tgttgacaaa tgtaaacatt    1740
ttcagaaata ttcatgaagc ggtcacagat cacagtgtct tttggttaca gcacaaaatg    1800
atggcagtgg tttgaaaaac taaaacagaa aaaaaaatgg aagccaacac atcactcatt    1860
ttaggcaaat gtttaaacat ttttatctat cagaatgttt attgttgctg gttataagca    1920
gcaggattgg ccggctagtg tttcctctca tttcccttg atacagtcaa caagcctgac    1980
cctgtaaaat ggaggtggaa agacaagctc aagtgttcac aacctggaag tgcttcggga    2040
agaaggggac aatggcagaa caggtgttgg tgacaattgt caccaattgg ataaagcagc    2100
tcaggttgta gtgggccatt aggaaactgt cggtttgctt tgatttccct gggagctgtt    2160
ctctgtcgtg agtgtctctt gtctaaacgt ccattaagct gagagtgcta tgaagacagg    2220
atctagaata atcttgctca cagctgtgct ctgagtgcct agcggagttc cagcaaacaa    2280
aatggactca agagagattt gattaatgaa tcgtaatgaa gttggggttt attgtacagt    2340
ttaaaatgtt agatgttttt aatttttta ataaatggaa tacttttttt tttttttaa    2400 agaaagcaac tttactgaga caatgtagaa agaagttttg ttccgtttct ttaatgtggt    2460
tgaagagcaa tgtgtggctg aagacttttg ttatgaggag ctgcagatta gctaggggac    2520
agctggaatt atgctggctt ctgataatta ttttaaaggg gtctgaaatt tgtgatggaa    2580
tcagatttta acagctctct tcaatgacat agaaagttca tggaactcat gttttaaag    2640 ggctatgtaa atatatgaac attagaaaaa tagcaacttg tgttacaaaa atacaaacac    2700
atgttaggaa ggtactgtca tgggctaggc atggtggctc acacctgtaa tcccagcatt    2760 tgggaagct aagatgggtg gatcacttga ggtcaggagt tgagaccag cctgccaac    2820 atggcgaaac ccctctctac taaaaataca aaaatttgcc aggcgtggtg gcgggtgcct    2880
gtaatcccag ctacttggga ggctgaggca agagaatcgc ttgaaccag gaggcagagg    2940 ttgcagtgag ccgagatcgt gccattgcac tccagcctgg gtgacaaagc gagactccat    3000
ctcaaaaaaa aaaaaaaaaa aaaggaaag aactgtcatg taaacatacc aacatgttta    3060
aacctgacaa tggtgttatt tgaaacttta tattgttctt gtaagcttta actatatctc    3120
tctttaaaat gcaaataat gtcttaagat tcaaagtctg tattttaaa gcatggcttt    3180 ggctttgcaa aataaaaaat gtgttttgta catgaa                              3216
```

<210> SEQ ID NO 4
<211> LENGTH: 3479
<212> TYPE: DNA
<213> ORGANISM: Homo sapiens -continued

<400> SEQUENCE: 4

```
aactcacacg gcctcttgca aacgttccca aatcttccca gtcggcttgc agagactcct        60
tgctcccagg agataaccag gtaaaggagt atgaaagttt gggtacaaac tcattgctgc       120
aaattgaaaa ccatgcaaag gctgtcttcc tctggggagt tcaatgcctc tcttttcctt      180
atcactttac cattggttgg actttgattc cagggatcct acgattactc aatacccctac      240 aggatataca tggttaacca tttgcatttg ggcaaatagg cgttactttt caataggaag       300
tggcaatcca gaacttgctt tgggcaatt ctagtagctc accgcttttt tcttaatgac        360
tgctagaagc tgcatcttat tgacagatgg tcatcacatt ggtgagctgg agtcatcaga       420 ttgtgggggcc cggagtgagg ctgaagggag tggatcagag cactgcctga gagtcacctc      480
tactttcctg ctaccgctgc ctgtgagctg aaggggctga accatacact ccttttttcta     540 caaccagctt gcattttttc tgcccacaat gagcggggaa tcaatgaatt tcagcgatgt      600
tttcgactcc agtgaagatt atttttgtgtc agtcaatact tcatattact cagttgattc     660
tgagatgtta ctgtgctcct tgcaggaggt caggcagttc tccaggctat ttgtaccgat      720
tgcctactcc ttgatctgtg tcttttggcct cctggggaat attctggtgg tgatcacctt     780 tgcttttttat aagaaggcca ggtctatgac agacgtctat ctcttgaaca tggccattgc    840
agacatcctc tttgttctta ctctcccatt ctgggcagtg agtcatgcca ccggtgcgtg      900
ggttttcagc aatgccacgt gcaagttgct aaaaggcatc tatgccatca actttaactg      960
cgggatgctg ctcctgactt gcattagcat ggaccggtac atcgccattg tacaggcgac     1020
taagtcattc cggctccgat ccagaacact accgcgcagc aaaatcatct gccttgttgt     1080
gtgggggctg tcagtcatca tctccagctc aacttttgtc ttcaaccaaa aatacaacac      1140
ccaaggcagc gatgtctgtg aacccaagta ccagactgtc tcggagccca tcaggtggaa     1200
gctgctgatg ttgggggcttg agctactctt tggtttcttt atcccctttga tgttcatgat   1260 attttgttac acgttcattg tcaaaacctt ggtgcaagct cagaattcta aaaggcacaa      1320
agccatccgt gtaatcatag ctgtggtgct tgtgtttctg gcttgtcaga ttcctcataa      1380
catggtcctg cttgtgacgg ctgcaaattt gggtaaaatg aaccgatcct gccagagcga     1440
aaagctaatt ggctatacga aaactgtcac agaagtcctg gctttcctgc actgctgcct    1500
gaaccctgtg ctctacgctt ttattgggca gaagttcaga aactactttc tgaagatctt    1560
gaaggacctg tggtgtgtga aaggaagta caagtcctca ggcttctcct gtgccgggag      1620
gtactcagaa acatttctc ggcagaccag tgagaccgca gataacgaca atgcgtcgtc      1680
cttcactatg tgatagaaag ctgagtctcc ctaaggcatg tgtgaaacat actcatagat      1740
gttatgcaaa aaaagtcta tggccaggta tgcatggaaa atgtgggaat taagcaaaat     1800
caagcaagcc tctctcctgc gggacttaac gtgctcatgg gctgtgtgat ctcttcaggg    1860
tggggtggtc tctgataggt agcatttttcc agcactttgc aaggaatgtt ttgtagctct    1920
agggtatata tccgcctggc atttcacaaa acagcctttg ggaaatgctg aattaaagtg     1980
aattgttgac aaatgtaaac attttcagaa atattcatga agcggtcaca gatcacagtg     2040
tcttttggtt acagcacaaa atgatggcag tggtttgaaa aactaaaaca gaaaaaaaaa    2100
tggaagccaa cacatcactc attttaggca aatgtttaaa cattttttatc tatcagaatg    2160 tttattgttg ctggttataa gcagcaggat tggccggcta gtgtttcctc tcatttccct     2220
ttgatacagt caacaagcct gaccctgtaa aatggaggtg gaaagacaag ctcaagtgtt     2280
cacaacctgg aagtgcttcg ggaagaaggg gacaatggca gaacaggtgt tggtgacaat    2340
```

| | |
|---|---:|
| tgtcaccaat tggataaagc agctcaggtt gtagtgggcc attaggaaac tgtcggtttg | 2400 |
| ctttgatttc cctgggagct gttctctgtc gtgagtgtct cttgtctaaa cgtccattaa | 2460 |
| gctgagagtg ctatgaagac aggatctaga ataatcttgc tcacagctgt gctctgagtg | 2520 |
| cctagcggag ttccagcaaa caaaatggac tcaagagaga tttgattaat gaatcgtaat | 2580 |
| gaagttgggg tttattgtac agtttaaaat gttagatgtt tttaattttt taaataaatg | 2640 |
| gaatactttt tttttttttt taaagaaagc aactttactg agacaatgta gaagaagtt | 2700 |
| ttgttccgtt tctttaatgt ggttgaagag caatgtgtgg ctgaagactt tgttatgag | 2760 |
| gagctgcaga ttagctaggg gacagctgga attatgctgg cttctgataa ttattttaaa | 2820 |
| ggggtctgaa atttgtgatg gaatcagatt ttaacagctc tcttcaatga catagaaagt | 2880 |
| tcatggaact catgttttta aagggctatg taaatatatg aacattagaa aaatagcaac | 2940 |
| ttgtgttaca aaaatacaaa cacatgttag gaaggtactg tcatgggcta ggcatggtgg | 3000 |
| ctcacacctg taatcccagc attttgggaa gctaagatgg gtggatcact tgaggtcagg | 3060 |
| agtttgagac cagcctggcc aacatggcga accccctctc tactaaaaat acaaaaattt | 3120 |
| gccaggcgtg gtggcgggtg cctgtaatcc cagctacttg ggaggctgag gcaagagaat | 3180 |
| cgcttgaacc caggaggcag aggttgcagt gagccgagat cgtgccattg cactccagcc | 3240 |
| tgggtgacaa agcgagactc catctcaaaa aaaaaaaaa aaaaaaagga agaactgtc | 3300 |
| atgtaaacat accaacatgt ttaaacctga caatggtgtt atttgaaact ttatattgtt | 3360 |
| cttgtaagct ttaactatat ctctctttaa aatgcaaaat aatgtcttaa gattcaaagt | 3420 |
| ctgtattttt aaagcatggc tttggctttg caaaataaaa aatgtgtttt gtacatgaa | 3479 |

<210> SEQ ID NO 5
<211> LENGTH: 793
<212> TYPE: DNA
<213> ORGANISM: Homo sapiens

<400> SEQUENCE: 5

| | |
|---|---:|
| aggagttgtg agtttccaag ccccagctca ctctgaccac ttctctgcct gcccagcatc | 60 |
| atgaagggcc ttgcagctgc cctccttgtc ctcgtctgca ccatggccct ctgctcctgt | 120 |
| gcacaagttg gtaccaacaa agagctctgc tgcctcgtct atacctcctg gcagattcca | 180 |
| caaaagttca tagttgacta ttctgaaacc agccccagt gccccaagcc aggtgtcatc | 240 |
| ctcctaacca agagaggccg gcagatctgt gctgacccca ataagaagtg ggtccagaaa | 300 |
| tacatcagcg acctgaagct gaatgcctga ggggcctgga agctgcgagg gcccagtgaa | 360 |
| cttggtgggc ccaggaggga acaggagcct gagccagggc aatggccctg ccaccctgga | 420 |
| ggccacctct tctaagagtc ccatctgcta tgcccagcca cattaactaa ctttaatctt | 480 |
| agtttatgca tcatatttca ttttgaaatt gatttctatt gttgagctgc attatgaaat | 540 |
| tagtattttc tctgacatct catgacattg tctttatcat cctttcccct ttcccttcaa | 600 |
| ctcttcgtac attcaatgca tggatcaatc agtgtgatta gctttctcag cagacattgt | 660 |
| gccatatgta tcaaatgaca aatctttatt gaatggtttt gctcagcacc acctttaat | 720 |
| atattggcag tacttattat ataaaaggta aaccagcatt ctcactgtga aaaaaaaaa | 780 |
| aaaaaaaaaa aaa | 793 |

<210> SEQ ID NO 6
<211> LENGTH: 851
<212> TYPE: DNA

<213> ORGANISM: Homo sapiens

<400> SEQUENCE: 6

```
agaatataac agcactccca aagaactggg tactcaacac tgagcagatc tgttctttga    60
gctaaaaacc atgtgctgta ccaagagttt gctcctggct gctttgatgt cagtgctgct   120
actccacctc tgcggcgaat cagaagcagc aagcaacttt gactgctgtc ttggatacac   180
agaccgtatt cttcatccta aatttattgt gggcttcaca cggcagctgg ccaatgaagg   240
ctgtgacatc aatgctatca tctttcacac aaagaaaaag ttgtctgtgt gcgcaaatcc   300
aaaacagact tgggtgaaat atattgtgcg tctcctcagt aaaaaagtca agaacatgta   360
aaaactgtgg ctttctgga atggaattgg acatagccca agaacagaaa gaaccttgct   420
ggggttggag gtttcacttg cacatcatgg agggtttagt gcttatctaa tttgtgcctc   480
actggacttg tccaattaat gaagttgatt catattgcat catagtttgc tttgtttaag   540
catcacatta aagttaaact gtattttatg ttatttatag ctgtaggttt ctgtgtttta   600
gctatttaat actaattttc cataagctat tttggtttag tgcaaagtat aaaattatat   660
ttgggggga ataagattat atggactttc ttgcaagcaa caagctattt tttaaaaaaa   720
actatttaac attcttttgt ttatattgtt ttgtctccta aattgttgta attgcattat   780
aaaataagaa aaatattaat aagacaaata ttgaaaataa agaaacaaaa agttcttctg   840
ttaaaaaaaa a                                                         851
```

<210> SEQ ID NO 7
<211> LENGTH: 848
<212> TYPE: DNA
<213> ORGANISM: Homo sapiens

<400> SEQUENCE: 7

```
agaatataac agcactccca aagaactggg tactcaacac tgagcagatc tgttctttga    60
gctaaaaacc atgtgctgta ccaagagttt gctcctggct gctttgatgt cagtgctgct   120
actccacctc tgcggcgaat cagaagcaag caactttgac tgctgtcttg gatacacaga   180
ccgtattctt catcctaaat ttattgtggg cttcacacgg cagctggcca atgaaggctg   240
tgacatcaat gctatcatct ttcacacaaa gaaaaagttg tctgtgtgcg caaatccaaa   300
acagacttgg gtgaaatata ttgtgcgtct cctcagtaaa aaagtcaaga acatgtaaaa   360
actgtggctt ttctggaatg gaattggaca tagcccaaga acagaaagaa ccttgctggg   420
gttggaggtt tcacttgcac atcatggagg gtttagtgct tatctaattt gtgcctcact   480
ggacttgtcc aattaatgaa gttgattcat attgcatcat agtttgcttt gtttaagcat   540
cacattaaag ttaaactgta ttttatgtta tttatagctg taggttttct gtgtttagct   600
atttaatact aattttccat aagctatttt ggtttagtgc aaagtataaa attatatttg   660
gggggaata agattatatg gactttcttg caagcaacaa gctatttttt aaaaaaaact   720
atttaacatt cttttgttta tattgttttg tctcctaaat tgttgtaatt gcattataaa   780
ataagaaaaa tattaataag acaaatattg aaaataagaa aacaaaaagt tcttctgtta   840
aaaaaaaa                                                             848
```

<210> SEQ ID NO 8
<211> LENGTH: 144
<212> TYPE: DNA
<213> ORGANISM: Artificial Sequence
<220> FEATURE:
<223> OTHER INFORMATION: polynucleotide sequence encoding polypeptide according to SEQ ID NO.:1

<400> SEQUENCE: 8
atgagcgggg aatcaatgaa tttcagcgat gttttcgact ccagtgaaga ttattttgtg        60
tcagtcaata cttcatatta ctcagttgat tctgagatgt tactgtgctc cttgcaggag       120
gtcaggcagt tctccaggct attt                                              144

<210> SEQ ID NO 9
<211> LENGTH: 29
<212> TYPE: PRT
<213> ORGANISM: Artificial Sequence
<220> FEATURE:
<223> OTHER INFORMATION: peptide inhibitor of CCR6

<400> SEQUENCE: 9

Glu Asp Cys Cys Leu Val Tyr Thr Ser Trp Gln Ile His Pro Lys Phe
1               5                   10                  15

Ile Val Asp Tyr Ser Glu Thr Ser Pro Gln Cys Pro Lys
            20                  25

<210> SEQ ID NO 10
<211> LENGTH: 20
<212> TYPE: DNA
<213> ORGANISM: Artificial Sequence
<220> FEATURE:
<223> OTHER INFORMATION: forward primer GAPDH

<400> SEQUENCE: 10
caccagggct gcttttaact                                                    20

<210> SEQ ID NO 11
<211> LENGTH: 20
<212> TYPE: DNA
<213> ORGANISM: Artificial Sequence
<220> FEATURE:
<223> OTHER INFORMATION: reverse primer GAPDH

<400> SEQUENCE: 11
gatctcgctc ctggaagatg                                                    20

<210> SEQ ID NO 12
<211> LENGTH: 20
<212> TYPE: DNA
<213> ORGANISM: Artificial Sequence
<220> FEATURE:
<223> OTHER INFORMATION: forward primer CCR6

<400> SEQUENCE: 12
gcacaaaatg atggcagtgg                                                    20

<210> SEQ ID NO 13
<211> LENGTH: 20
<212> TYPE: DNA
<213> ORGANISM: Artificial Sequence
<220> FEATURE:
<223> OTHER INFORMATION: reverse primer CCR6

<400> SEQUENCE: 13
ccgaagcact tccaggttgt                                                    20

<210> SEQ ID NO 14
<211> LENGTH: 22
<212> TYPE: DNA
<213> ORGANISM: Artificial Sequence

```
<220> FEATURE:
<223> OTHER INFORMATION: forward primer collagen type I

<400> SEQUENCE: 14
ccctgtctgc ttcctgtaaa ct                                            22

<210> SEQ ID NO 15
<211> LENGTH: 22
<212> TYPE: DNA
<213> ORGANISM: Artificial Sequence
<220> FEATURE:
<223> OTHER INFORMATION: reverse primer collagen type I

<400> SEQUENCE: 15
catgttcggt tggtcaaaga ta                                            22

<210> SEQ ID NO 16
<211> LENGTH: 20
<212> TYPE: DNA
<213> ORGANISM: Artificial Sequence
<220> FEATURE:
<223> OTHER INFORMATION: forward primer alphaSMA

<400> SEQUENCE: 16
catcatgcgt ctggatctgg                                               20

<210> SEQ ID NO 17
<211> LENGTH: 20
<212> TYPE: DNA
<213> ORGANISM: Artificial Sequence
<220> FEATURE:
<223> OTHER INFORMATION: reverse primer alphaSMA

<400> SEQUENCE: 17
ggacaatctc acgctcagca                                               20

<210> SEQ ID NO 18
<211> LENGTH: 69
<212> TYPE: PRT
<213> ORGANISM: Homo sapiens

<400> SEQUENCE: 18

Ala Gln Val Gly Thr Asn Lys Glu Leu Cys Cys Leu Val Tyr Thr Ser
1               5                   10                  15

Trp Gln Ile Pro Gln Lys Phe Ile Val Asp Tyr Ser Glu Thr Ser Pro
            20                  25                  30

Gln Cys Pro Lys Pro Gly Val Ile Leu Leu Thr Lys Arg Gly Arg Gln
        35                  40                  45

Ile Cys Ala Asp Pro Asn Lys Lys Trp Val Gln Lys Tyr Ile Ser Asp
    50                  55                  60

Leu Lys Leu Asn Ala
65

<210> SEQ ID NO 19
<211> LENGTH: 70
<212> TYPE: PRT
<213> ORGANISM: Homo sapiens

<400> SEQUENCE: 19

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30
```

Asp Ile Asn Ala Ile Ile Phe His Thr Lys Lys Leu Ser Val Cys
            35                  40                  45

Ala Asn Pro Lys Gln Thr Trp Val Lys Tyr Ile Val Arg Leu Leu Ser
     50                  55                  60

Lys Lys Val Lys Asn Met
 65                 70

<210> SEQ ID NO 20
<211> LENGTH: 68
<212> TYPE: PRT
<213> ORGANISM: Homo sapiens

<400> SEQUENCE: 20

Met Arg Thr Ser Tyr Leu Leu Leu Phe Thr Leu Cys Leu Leu Leu Ser
 1               5                  10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
 65

<210> SEQ ID NO 21
<211> LENGTH: 64
<212> TYPE: PRT
<213> ORGANISM: Homo sapiens

<400> SEQUENCE: 21

Met Arg Val Leu Tyr Leu Leu Phe Ser Phe Leu Phe Ile Phe Leu Met
 1               5                  10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 22
<211> LENGTH: 29
<212> TYPE: PRT
<213> ORGANISM: Artificial Sequence
<220> FEATURE:
<223> OTHER INFORMATION: peptide inhibitor of CCR6

<400> SEQUENCE: 22

Glu Leu Cys Cys Leu Val Tyr Thr Ser Trp Gln Ile Pro Gln Lys Phe
 1               5                  10                  15

Ile Val Asp Tyr Ser Glu Thr Ser Pro Gln Cys Pro Lys
            20                  25

<210> SEQ ID NO 23
<211> LENGTH: 31
<212> TYPE: PRT
<213> ORGANISM: Artificial Sequence
<220> FEATURE:
<223> OTHER INFORMATION: peptide inhibitor of CCR6

<400> SEQUENCE: 23

Phe Asp Cys Cys Leu Gly Tyr Thr Asp Arg Ile Leu His Pro Lys Phe
1               5                   10                  15

Ile Val Gly Phe Thr Arg Gln Leu Ala Asn Glu Gly Cys Asp Ile
            20                  25                  30

<210> SEQ ID NO 24
<211> LENGTH: 87
<212> TYPE: DNA
<213> ORGANISM: Artificial Sequence
<220> FEATURE:
<223> OTHER INFORMATION: polynucleotide sequence encoding peptide
      according to SEQ ID NO.:9

<400> SEQUENCE: 24
gaggactgct gcctcgtcta tacctcctgg cagattcacc caaagttcat agttgactat        60
tctgaaacca gcccccagtg ccccaag                                            87

<210> SEQ ID NO 25
<211> LENGTH: 87
<212> TYPE: DNA
<213> ORGANISM: Artificial Sequence
<220> FEATURE:
<223> OTHER INFORMATION: polynucleotide sequence encoding polypeptide
      according to SEQ ID NO.:22

<400> SEQUENCE: 25
gagctctgct gcctcgtcta tacctcctgg cagattccac aaaagttcat agttgactat        60
tctgaaacca gcccccagtg ccccaag                                            87

<210> SEQ ID NO 26
<211> LENGTH: 93
<212> TYPE: DNA
<213> ORGANISM: Artificial Sequence
<220> FEATURE:
<223> OTHER INFORMATION: polynucleotide sequence encoding polypeptide
      according to SEQ ID NO.:23

<400> SEQUENCE: 26
tttgactgct gtcttggata cacagaccgt attcttcatc ctaaatttat tgtgggcttc        60
acacggcagc tggccaatga aggctgtgac atc                                     93

<210> SEQ ID NO 27
<211> LENGTH: 374
<212> TYPE: PRT
<213> ORGANISM: Homo sapiens

<400> SEQUENCE: 27

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

```
Phe Ser Asn Ala Thr Cys Lys Leu Leu Lys Gly Ile Tyr Ala Ile Asn
        115                 120                 125
Phe Asn Cys Gly Met Leu Leu Leu Thr Cys Ile Ser Met Asp Arg Tyr
        130                 135                 140
Ile Ala Ile Val Gln Ala Thr Lys Ser Phe Arg Leu Arg Ser Arg Thr
145                 150                 155                 160
Leu Pro Arg Ser Lys Ile Ile Cys Leu Val Val Trp Gly Leu Ser Val
                165                 170                 175
Ile Ile Ser Ser Ser Thr Phe Val Phe Asn Gln Lys Tyr Asn Thr Gln
                180                 185                 190
Gly Ser Asp Val Cys Glu Pro Lys Tyr Gln Thr Val Ser Glu Pro Ile
                195                 200                 205
Arg Trp Lys Leu Leu Met Leu Gly Leu Glu Leu Leu Phe Gly Phe Phe
        210                 215                 220
Ile Pro Leu Met Phe Met Ile Phe Cys Tyr Thr Phe Ile Val Lys Thr
225                 230                 235                 240
Leu Val Gln Ala Gln Asn Ser Lys Arg His Lys Ala Ile Arg Val Ile
                245                 250                 255
Ile Ala Val Val Leu Val Phe Leu Ala Cys Gln Ile Pro His Asn Met
                260                 265                 270
Val Leu Leu Val Thr Ala Ala Asn Leu Gly Lys Met Asn Arg Ser Cys
        275                 280                 285
Gln Ser Glu Lys Leu Ile Gly Tyr Thr Lys Thr Val Thr Glu Val Leu
        290                 295                 300
Ala Phe Leu His Cys Cys Leu Asn Pro Val Leu Tyr Ala Phe Ile Gly
305                 310                 315                 320
Gln Lys Phe Arg Asn Tyr Phe Leu Lys Ile Leu Lys Asp Leu Trp Cys
                325                 330                 335
Val Arg Arg Lys Tyr Lys Ser Ser Gly Phe Ser Cys Ala Gly Arg Tyr
                340                 345                 350
Ser Glu Asn Ile Ser Arg Gln Thr Ser Glu Thr Ala Asp Asn Asp Asn
        355                 360                 365
Ala Ser Ser Phe Thr Met
        370
```